United States Patent [19]

Nakamura et al.

[11] Patent Number: 5,767,289
[45] Date of Patent: Jun. 16, 1998

[54] AROMATIC CARBOXYLIC ACID BICYCLIC SULFUR COMPOUNDS

[75] Inventors: Kazufumi Nakamura; Masashi Sakamoto; Ichiro Nasuno. all of Sodegaura. Japan

[73] Assignee: Idemitsu Kosan Company, Limited. Tokyo. Japan

[21] Appl. No.: 727,915

[22] Filed: Oct. 9, 1996

Related U.S. Application Data

[62] Division of Ser. No. 595,359, Feb. 1, 1996, Pat. No. 5,607, 898 which is a continuation-in-part of PCT/JP94/01264, Aug. 1, 1994.

[30] Foreign Application Priority Data

Aug. 2, 1993 [JP] Japan .............. HEI 5-191428
Apr. 11, 1994 [JP] Japan .............. HEI 6-71788
Feb. 13, 1995 [JP] Japan .............. HEI 7-24102

[51] Int. Cl.$^6$ ............................................. C07D 335/06
[52] U.S. Cl. ......................................... 549/23; 549/28
[58] Field of Search ................................. 549/23, 28

[56] References Cited

U.S. PATENT DOCUMENTS 4,885,022  12/1989  Baba et al. .
5,468,722  11/1995  Shibata et al. .
5,587,484  12/1996  Shibata et al. .................. 549/23

FOREIGN PATENT DOCUMENTS 63-122673  5/1988  Japan .
63-170365  7/1988  Japan .
63-122672  5/1989  Japan .
2-173      1/1990  Japan .
4-257503   9/1992  Japan .

*Primary Examiner*—Robert W. Ramsuer
*Attorney, Agent, or Firm*—Frishauf, Holtz, Goodman, Langer & Chick, P.C.

[57] ABSTRACT

A bicyclic sulfur compound of the following formula:

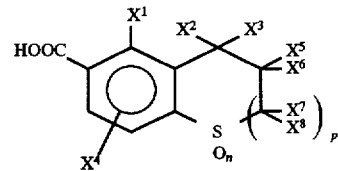

wherein $X^1$ is selected from the group consisting of $C_1$–$C_4$ alkyl, halogen, $C_1$–$C_4$ haloalkyl, $C_2$–$C_4$ alkoxyalkyl, $C_1$–$C_4$ alkoxy and $C_1$–$C_4$ haloalkoxy; each of $X^2$ and $X^3$ is independently selected from the group consisting of hydrogen, $C_1$–$C_4$ alkyl and $C_1$–$C_4$ haloalkyl; $X^4$ is selected from the group consisting of hydrogen, halogen, $C_1$–$C_4$ alkyl, $C_1$–$C_4$ haloalkyl and $C_1$–$C_4$ alkoxy; each of $X^5$, $X^6$, $X^7$ and $X^8$ is independently hydrogen or $C_1$–$C_4$ alkyl; or $X^2$ and $X^5$ can combine to form an unsaturated double bond; or $X^5$ and $X^7$ can combine to form an unsaturated bond; p is an integer of 0 or 1; and n is an integer of 0, 1 or 2; or a salt thereof.

10 Claims, No Drawings

AROMATIC CARBOXYLIC ACID BICYCLIC SULFUR COMPOUNDS

This application is a division of application Ser. No. 08/595,359, filed Feb. 1, 1996, now U.S. Pat. No. 5,607,898 which is continuation-in-part application of International Application PCT/JP94/01264 filed Aug. 1, 1994.

TECHNICAL FIELD

The present invention relates to novel pyrazole derivatives, herbicides containing the pyrazole derivatives as active ingredients, and intermediates suitable for the production of the pyrazole derivatives.

TECHNICAL BACKGROUND AND PROBLEMS WHICH THE INVENTION SEEKS TO SOLVE

Herbicides are very important chemicals for saving weed-controlling labors and improving the yield of agricultural and horticultural crops and have been therefore aggressively studied and developed for many years, and a diversity of herbicides have now been put to practical use. Today, however, it is still desired to develop novel chemicals having excellent herbicidal efficacy, particularly chemicals which can selectively control target weeds alone at a low dosage without causing phytotoxicity on crops.

During the time of planting corn, etc., a triazine-based herbicide such as atrazine and acid anilide-based herbicides such as alachlor and metolachlor have been conventionally used. However, atrazine shows low efficacy to gramineous weeds, and on the other hand, alachlor and metolachlor show low efficacy to broad-leaved weeds. It is therefore difficult at present to control gramineous weeds and broad-leaved weeds together simultaneously with a single herbicide. Further, the above herbicides are undesirable in view of an environmental problem due to their high dosage requirement.

It is known that in paddy land, a variety of weeds, annual gramineous weeds such as barnyardgrass, annual cyperaceous weeds such as umbrella plant, annual broad-leaved weeds such as monochoria and toothcup and perennial weeds such as sagitaria pygmaea, pondweed, oriental water plantain, bulrush, needle spikerush, serotinus, water chestnut, arrowhead and dropwort grow together with paddy rice, and in rice cultivation, it is very important to effectively control these weeds at a low dosage in view of environmental pollution without causing phytotoxicity on paddy rice. Generally, it is known that chemicals having high herbicidal efficacy on barnyardgrass are liable to cause phytotoxicity on paddy rice, and it is a particularly important subject to develop a chemical which has high herbicidal efficacy on barnyardgrass as a gramineous weed and has excellent inter-genus selectivity between paddy rice and barnyardgrass.

Meanwhile, it is known that specific 4-benzoylpyrazoles have herbicidal efficacy (JP-A-63-122672, JP-A-63-122673, JP-A-63-170365, JP-A-1-52759, JP-A-2-173 and JP-A-2-288866), and pyrazolate of the following chemical formula is among herbicides commercially available at present.

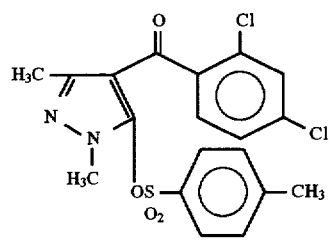

Further, a compound (A), the typical example of 4-benzoylpyrazole derivatives disclosed in the above publications, has the following chemical formula (Compound No. 35 in JP-A-2-173).

Compound (A): Compound No. 35 disclosed in JP-A-2-173

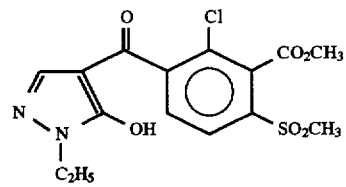

The above 4-benzoylpyrazole derivatives have herbicidal activity, while their herbicidal activity is practically insufficient. In particular, their herbicidal activity to gramineous weeds such as barnyardgrass and green foxtail is very poor. When they are used as a herbicide for controlling weeds in paddy land, they may cause phytotoxicity on paddy rice since they have poor selectivity between paddy rice and gramineous weeds.

The present inventors have therefore proposed pyrazole derivatives having a thiochroman ring and have filed patent applications directed thereto (JP-A-4-185526 and International Laid-open Patent Publication WO93/18031). Typical examples (B) and (C) of the compounds disclosed in the specifications of the above prior applications are as follows.

Compound (B): Compound No. 66 disclosed in International Laid-open Patent Publication WO93/18031

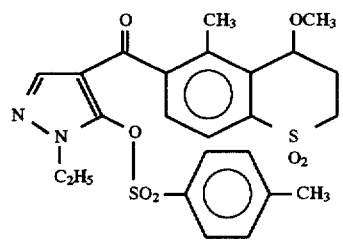

Compound (C): Compound No. b-3 disclosed in JP-A-4-185526

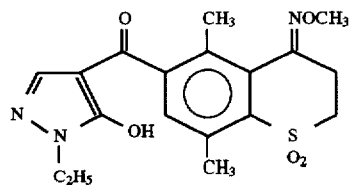

The above compounds have high herbicidal activity, while they still have room for improvement in view of safety to paddy rice.

The present invention has been made in view of the above circumstances, and the object thereof is to provide a pyrazole derivative which can control a broad range of upland weeds and paddy land weeds, particularly barnyardgrass in paddy land, at a low dosage without causing phytotoxicity on crops such as corn, paddy rice, etc., a herbicide containing the same, and an intermediate for obtaining the pyrazole derivative.

DISCLOSURE OF THE INVENTION

The first aspect of the present invention is directed to a pyrazole derivative of the general formula (I).

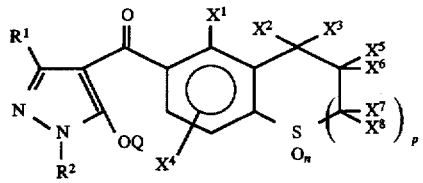

wherein:

$R^1$ is one member selected from the group consisting of hydrogen, a $C_1$–$C_4$ alkyl group, a $C_1$–$C_4$ haloalkyl group and a $C_2$–$C_4$ alkoxyalkyl group;

$R^2$ is one member selected from the group consisting of a $C_1$–$C_4$ alkyl group, a $C_2$–$C_4$ alkenyl group and a $C_2$–$C_4$ haloalkenyl group;

$X^1$ is one member selected from hydrogen atom, halogen atom, a $C_1$–$C_4$ alkyl group, a $C_1$–$C_4$ haloalkyl group, a $C_2$–$C_4$ alkoxyalkyl group, a $C_1$–$C_4$ alkoxy group and a $C_1$–$C_4$ haloalkoxy group;

each of $X^2$ and $X^3$ is independently one member selected from the group consisting of hydrogen atom, a $C_1$–$C_4$ alkyl group and a $C_1$–$C_4$ haloalkyl group;

$X^4$ is one member selected from the group consisting of hydrogen atom, halogen atom, a $C_1$–$C_4$ alkyl group, a $C_1$–$C_4$ haloalkyl group and $C_1$–$C_4$ alkoxy group;

each of $X^5$, $X^6$, $X^7$ and $X^8$ is independently hydrogen atom or a $C_1$–$C_4$ alkyl group;

further, a combination of $X^2$ and $X^5$ or a combination of $X^5$ and $X^7$ may be an unsaturated bond;

n is an integer of 0, 1 or 2;

p is an integer of 0 or 1; and

Q is hydrogen atom or any one of the following groups (a) to (h).

$-SO_2-R^3$,  (a)

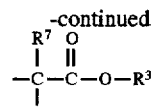 (b)

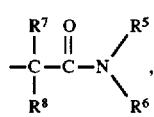 (c)

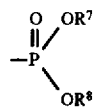 (d)

 (e)

-continued (f)

(g)

(h)

In the groups (a) to (h), $R^3$ is one member selected from the group consisting of a $C_1$–$C_8$ alkyl group, a $C_3$–$C_8$ cycloalkyl group and a group of the general formula (V), (V)

in which Y is halogen atom, nitro group, a $C_1$–$C_4$ alkyl group, a $C_1$–$C_4$ alkoxy group or a $C_1$–$C_4$ haloalkyl group, and m is and integer of 0, 1 or 2

$R^4$ is one member selected from the group consisting of a $C_1$–$C_8$ alkyl group, a $C_3$–$C_8$ cycloalkyl group, pyridyl group and a group of the general formula (V), $R^5$ is hydrogen atom or a $C_1$–$C_4$ alkyl group, $R^6$ is one member selected from the group consisting of hydrogen atom, a $C_1$–$C_4$ alkyl group and a group of the general formula (V), and each of $R^7$ and $R^8$ is independently hydrogen atom or a $C_1$–$C_4$ alkyl group, and a salt thereof.

The second aspect of the present invention is directed to a herbicide containing the pyrazole derivative of the above general formula (I) and/or a salt thereof as active ingredient.

Further, the third aspect of the present invention is directed to an aromatic carboxylic acid derivative of the general formula (II) or a salt thereof, useful for the production of the pyrazole derivative of the general formula (I),

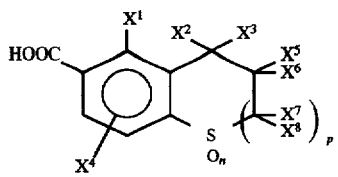

wherein:

$X^1$ is one member selected from the group consisting of a $C_1$–$C_4$ alkyl group, halogen atom, a $C_1$–$C_4$ haloalkyl group, a $C_2$–$C_4$ alkoxyalkyl, a $C_1$–$C_4$ alkoxy group and a $C_1$–$C_4$ haloalkoxy group;

each of $X^2$ and $X^3$ is independently one member selected from the group consisting of hydrogen atom, a $C_1$–$C_4$ alkyl group and a $C_1$–$C_4$ haloalkyl group;

$X^4$ is one member selected from the group consisting of hydrogen atom, halogen atom, a $C_1$–$C_4$ alkyl group, a $C_1$–$C_4$ haloalkyl group and a $C_1$–$C_4$ alkoxy group;

each of $X^5$, $X^6$, $X^7$ and $X^8$ is independently one member selected from the group consisting of hydrogen atom and a $C_1$–$C_4$ alkyl group;

further, a combination of $X^2$ and $X^5$ or a combination of $X^5$ and $X^7$ may be an unsaturated bond;

p is an integer of 0 or 1; and n is an integer of 0, 1 or 2.

PREFERRED EMBODIMENTS OF THE INVENTION

The novel pyrazole derivative of the present invention has the following general formula (I).

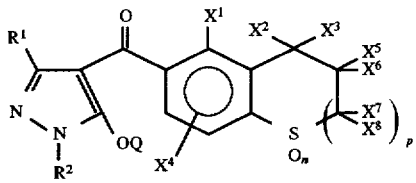

In the general formula (I), $R^1$ is hydrogen atom, a $C_1$-$C_4$ alkyl group, a $C_1$-$C_4$ haloalkyl group or a $C_2$-$C_4$ alkoxyalkyl group, preferably hydrogen atom or a $C_1$-$C_4$ alkyl group. Specific examples of the $C_1$-$C_4$ alkyl group include methyl, ethyl, a propyl group such as n-propyl, and a butyl group such as n-butyl and i-butyl. The propyl group and the butyl group may be linear, cyclic or branched. Methyl is preferred. The $C_1$-$C_4$ haloalkyl group is the same as the $C_1$-$C_4$ alkyl group except that at least one hydrogen atom of the $C_1$-$C_4$ alkyl group is replaced with a halogen atom (e.g., chlorine, fluorine, bromine or iodine), and the $C_1$-$C_4$ haloalkyl group includes —$CF_3$, —$C_2F_5$, —$C_2H_4F$, —$CH_2Cl$, —$CHF_2$, —$CCl_3$, —$C_2H_3Cl_2$ and —$C_2H_3F_2$. Specific examples of the $C_2$-$C_4$ alkoxyalkyl group include —$CH_2$—$OCH_3$, —$CH_2$—$OC_2H_5$, —$CH_2$—$OC_3H_7$, —$CH(CH_3)OCH_3$, —$CH(CH_3)OC_2H_5$, —$CH_2CH_2OCH_3$ and —$CH_2CH_2OC_2H_5$.

In the general formula (I), $R^2$ is a $C_1$-$C_4$ alkyl group, a $C_2$-$C_4$ alkenyl group or a $C_2$-$C_4$ haloalkenyl group, preferably a $C_1$-$C_4$ alkyl group. Specific examples of the $C_1$-$C_4$ alkyl group include methyl, ethyl, propyl and butyl. The propyl and the butyl may be linear, cyclic or branched. Preferred are methyl and ethyl. Specific examples of the $C_2$-$C_4$ alkenyl group include —$CH$=$CH_2$, —$CH_2$—$CH$=$CH_2$ and —$CH$=$CH$—$CH$=$CH_2$. The $C_2$-$C_4$ haloalkenyl group is the same as the above $C_2$-$C_4$ alkenyl group except that at least one hydrogen atom of the $C_2$-$C_4$ alkenyl group is replaced with a halogen atom (e.g., chlorine, fluorine, bromine or iodine).

In the general formula (I), $X^1$ is hydrogen atom, a $C_1$-$C_4$ alkyl group, a $C_1$-$C_4$ haloalkyl group, a $C_2$-$C_4$ alkoxyalkyl group, halogen atom, a $C_1$-$C_4$ alkoxy group or a $C_1$-$C_4$ haloalkoxy group, preferably a $C_1$-$C_4$ alkyl group or halogen atom. Specific examples of the $C_1$-$C_4$ alkyl group, the $C_1$-$C_4$ haloalkyl group and the $C_2$-$C_4$ alkoxyalkyl group include those described concerning $R^1$ or $R^2$. The $C_1$-$C_4$ alkyl group is preferably methyl or ethyl, more preferably methyl. Specific examples of the halogen include chlorine, fluorine, bromine and iodine, and the halogen is preferably chlorine. Specific examples of the $C_1$-$C_4$ alkoxy group include methoxy, ethoxy, propoxy and butoxy, and the propoxy and the butoxy may be linear, cyclic or branched. The $C_1$-$C_4$ haloalkoxy group is the same as the $C_1$-$C_4$ alkoxy group except that at least one hydrogen atom of the $C_1$-$C_4$ alkoxy group is replaced with a halogen atom (e.g., chlorine, fluorine, bromine or iodine). Examples of the $C_1$-$C_4$ haloalkoxy group include —$OCF_3$, —$OC_2F_5$, —$OC_2H_4F$, —$OC_2H_4Cl$, —$OCHF_2$, —$OCH_2F$, —$OCCl_3$, —$OC_2H_3Cl_2$ and —$OC_2H_3F_2$.

Each of $X^2$ and $X^3$ is independently hydrogen atom, a $C_1$-$C_4$ alkyl group or a $C_1$-$C_4$ haloalkyl group. Specific examples of the $C_1$-$C_4$ alkyl group and the $C_1$-$C_4$ haloalkyl group include those described concerning $R^1$. Specific examples of a combination of $X^2$ and $X^3$ are as follows.

When $X^2$ is hydrogen atom, $X^3$ is hydrogen atom or a $C_1$-$C_4$ alkyl group. Another specific preferred combination is that each of $X^2$ and $X^3$ is independently a $C_1$-$C_4$ alkyl group.

$X^4$ is hydrogen atom, halogen atom, a $C_1$-$C_4$ alkyl group, a $C_1$-$C_4$ haloalkyl group or a $C_1$-$C_4$ alkoxy group. Specific examples of the halogen atom, the $C_1$-$C_4$ alkyl group, the $C_1$-$C_4$ haloalkyl group and the $C_1$-$C_4$ alkoxy group include those described concerning $X^1$. $X^4$ is preferably hydrogen atom, halogen atom or a $C_1$-$C_4$ alkyl group, more preferably hydrogen atom, chlorine atom or methyl group. When p=0, the position of $X^4$ is the 6- or 7-position, preferably the 7-position, on the benzo[b]thiophene ring. When p=1, the position of $X^4$ is the 7- or 8-position, preferably the 8-position, on the thiochroman ring.

Each of $X^5$, $X^6$, $X^7$ and $X^8$ is independently hydrogen atom or a $C_1$-$C_4$ alkyl group. Specific examples of the $C_1$-$C_4$ alkyl group include those described concerning $R^1$. Preferred is hydrogen atom or methyl group.

A combination of $X^2$ and $X^5$ or a combination of $X^5$ and $X^7$ may form an unsaturated bond.

Q is hydrogen or one of the following groups (a) to (h).

 (a)

 (b)

 (c)

 (d)

 (e)

 (f)

 (g)

 (h)

In the above groups (a) to (h), $R^3$ is one member selected from the group consisting of a $C_1$-$C_8$ alkyl group, a $C_3$-$C_8$ cycloalkyl group and a group of the general formula (V).

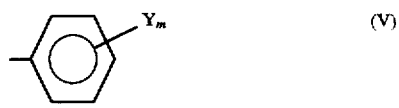 (V)

Examples of the above $C_1$-$C_8$ alkyl group include methyl, ethyl, propyl, butyl, pentyl, hexyl, heptyl and octyl groups. When the number of carbon atoms is 3 or greater, the alkyl group may be linear or branched. Examples of the $C_3$-$C_8$ cycloalkyl group include cyclopropyl, cyclobutyl, cyclopentyl, cyclohexyl, cycloheptyl and cyclooctyl groups.

In the general formula (V), Y is halogen atom, nitro group, a $C_1$–$C_4$ alkyl group, a $C_1$–$C_4$ alkoxy group or a $C_1$–$C_4$ haloalkyl group. The halogen atom includes those described concerning $X^1$. Examples of the $C_1$–$C_4$ alkyl group include those described concerning $R^1$. Examples of the $C_1$–$C_4$ alkoxy group include those described concerning $X^1$. The $C_1$–$C_4$ haloalkyl group is the same as the $C_1$–$C_4$ alkyl group described concerning $R^1$ except that a hydrogen atom of the $C_1$–$C_4$ alkyl group is replaced with a halogen atom, and specific examples of the $C_1$–$C_4$ haloalkyl group include —$CH_2F$, —$CHF_2$, —$CF_3$, —$CF_2CF_3$, —$CCl_3$ and —$CH_2CF_3$.

m representing the number of Y is an integer of 0, 1 or 2.

$R^4$ is one member selected from the group consisting of a $C_1$–$C_8$ alkyl group, a $C_3$–$C_8$ cycloalkyl group, pyridyl group and a group of the general formula (V). Specific examples of the $C_1$–$C_8$ alkyl group and the $C_3$–$C_8$ cycloalkyl group include those described concerning $R^3$.

$R^5$ is hydrogen atom or a $C_1$–$C_4$ alkyl group, and examples of the $C_1$–$C_4$ alkyl group include those described concerning $R^1$.

$R^6$ is hydrogen atom, a $C_1$–$C_4$ alkyl group or a group of the general formula (V), and specific examples of the $C_1$–$C_4$ alkyl group include those described concerning $R^1$.

Each of $R^7$ and $R^8$ is independently hydrogen atom or a $C_1$–$C_4$ alkyl group, and specific examples of the $C_1$–$C_4$ alkyl group include those described concerning $R^1$.

The substituent Q is preferably hydrogen atom or the following group.

As —$SO_2$—$R^3$:

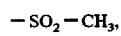
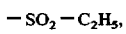
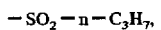
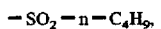
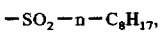
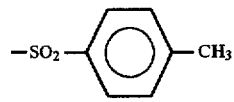
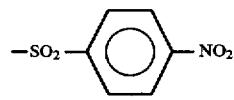
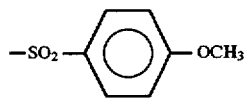
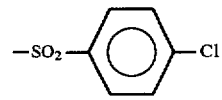
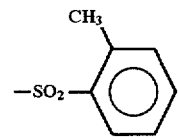

-continued
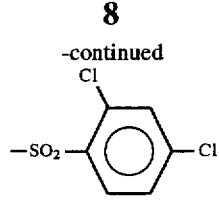

As —$\overset{O}{\underset{\|}{C}}$—$R^4$:

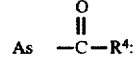
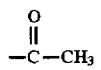
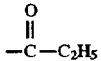
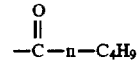
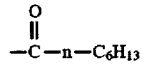
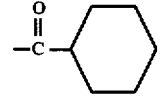
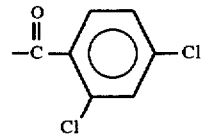
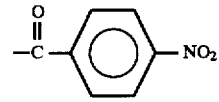
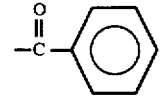

As —$\overset{R^7}{\underset{R^8}{\overset{|}{\underset{|}{C}}}}$—$\overset{O}{\underset{\|}{C}}$—$R^3$:

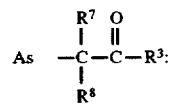
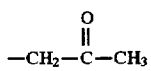

As —$\overset{O}{\underset{\|}{C}}$—O—$R^3$:

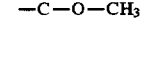

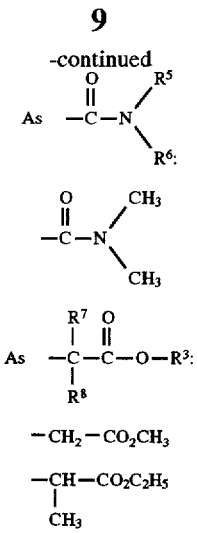

-continued $$As \quad -\overset{O}{\underset{\|}{C}}-N\overset{R^5}{\underset{R^6}{\diagup}}:$$

$$-\overset{O}{\underset{\|}{C}}-N\overset{CH_3}{\underset{CH_3}{\diagup}}$$

$$As \quad -\overset{R^7}{\underset{R^8}{\overset{|}{C}}}-\overset{O}{\underset{\|}{C}}-O-R^3:$$

$-CH_2-CO_2CH_3$ $-\underset{CH_3}{\overset{|}{C}H}-CO_2C_2H_5$ p is an integer of 0 or 1. When p is 1, the pyrazole derivative of the general formula (I) represents a pyrazole derivative of the general formula (Ix).

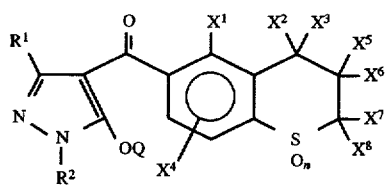

(Ix)

When p is 0, the pyrazole derivative of the general formula (I) represents a pyrazole derivative of the general formula (Iy).

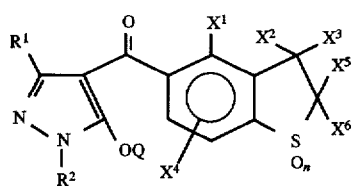

(Iy)

In the general formula (I), n which is the number of oxygen is an integer of 0, 1 or 2. That is, the compound (I) is sulfide when n is 0, sulfoxide when n is 1, and sulfone when n is 2.

The pyrazole derivative of the general formula (I) in which Q is hydrogen, i.e., a compound of the formula (Ia)

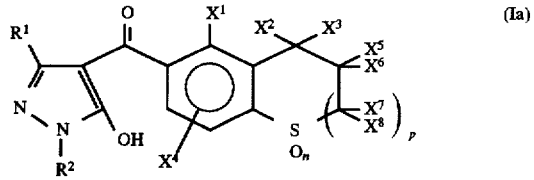

(Ia)

can have the following three structures due to tautomerism, and the pyrazole derivative of the present invention includes all of the above structures.

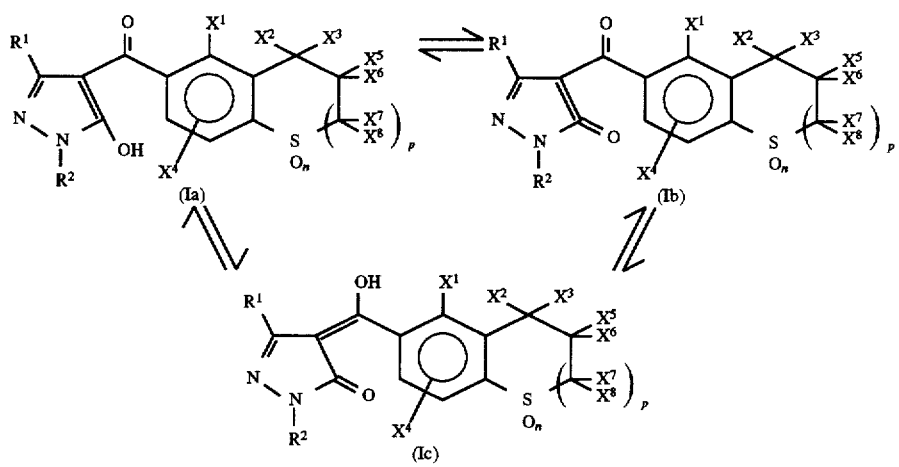

Further, the pyrazole derivative of the formula (Ia) is an acidic substance, and can be easily converted to a salt by treating it with a base. The pyrazole derivative of the present invention also includes the salt. The base can be selected from known bases without any problem, while examples of the base include organic bases such as amines and anilines and inorganic bases such as sodium compounds and potassium compounds. The amines include monoalkylamine, dialkylamine and trialkylamine. The alkyl group of the alkylamines is generally a $C_1$-$C_4$ alkyl group. The anilines include aniline, monoalkylaniline and dialkylaniline. The alkyl group of the alkylanilines is generally a $C_1$-$C_4$ alkyl group. The sodium compounds include sodium hydroxide and sodium carbonate, and the potassium compounds include potassium hydroxide and potassium carbonate.

The herbicide of the present invention contains the novel pyrazole derivative of the formula (I) and/or a salt thereof as an active ingredient. The herbicide can be prepared by mixing these compounds with a liquid carrier such as a solvent or a solid carrier such as a mineral fine powder, forming the mixture into the preparation form of a wettable powder, an emulsifiable concentrate, a dust or granules. The herbicide can be imparted with emulsifiability, dispersibility and spreadability by adding a surfactant when the herbicide is prepared.

When the herbicide of the present invention is used in the form of a wettable powder, generally, a composition prepared by mixing 10 to 55% by weight of the pyrazole derivative and/or its salt of the present invention, 40 to 88% by weight of a solid carrier and 2 to 5% by weight of a surfactant can be used as a wettable powder. Further, when it is used in the form of an emulsifiable concentrate, generally, it can be prepared by mixing 20 to 50% by weight of the pyrazole derivative and/or its salt of the present invention, 35 to 75% by weight of a solvent and 5 to 15% by weight of a surfactant.

On the other hand, when it is used in the form of a dust, generally, it can be prepared by mixing 1 to 15% by weight of the pyrazole derivative and/or its salt of the present invention, 80 to 97% by weight of a solid carrier and 2 to 5% by weight of a surfactant. Further, when it is used in the form of granules, the granules can be prepared by mixing 1 to 15% by weight of the pyrazole derivative and/or its salt of the present invention, 80 to 97% by weight of a solid carrier and 2 to 5% by weight of a surfactant.

The above solid carrier can be selected from mineral fine powders, and the mineral fine powders include oxides such as diatomaceous earth and slaked lime, phosphates such as apatite, sulfates such as gypsum, and silicates such as talc, pyroferrite, clay, kaolin, bentonite, acid clay, white carbon, powdered quartz and powdered silica.

The solvent is selected from organic solvents, and specific examples of the organic solvents include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

Further, the surfactant can be selected from anionic, nonionic, cationic and amphoteric ones (amino acid and betaine).

In combination with the pyrazole derivative of the above general formula (I) and/or the salt thereof, the herbicide of the present invention may contain, as active ingredients, other herbicidally active component as required. The "other" herbicidally active component can be selected from known herbicides such as phenoxy-, diphenyl ether-, triazine-, urea-, carbamate-, thiocarbamate-, acid anilide-, pyrazole-, phosphoric acid-, sulfonylurea- and oxadiazone-based herbicides. The other herbicidally active component can be properly selected from the above herbicides.

Further, the herbicide of the present invention may contain an insecticide, a fungicide, a plant growth regulator and a fertilizer as required.

The pyrazole derivative of the formula (I), provided by the present invention, is produced by the following methods (1) and (2).

First, the method (1) of producing the pyrazole derivative of the present invention will be explained in detail.

Method (1) of producing pyrazole derivative

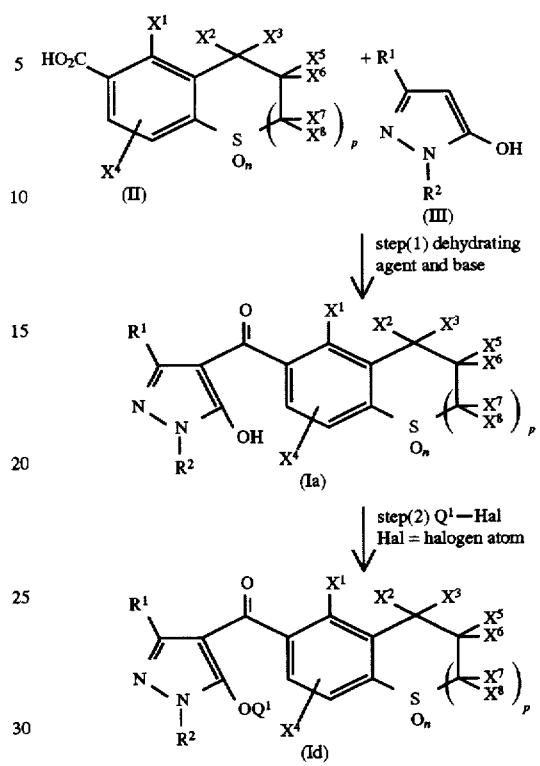

In the above reaction scheme, $Q^1$ is any one of the following groups (a) to (h).

  (a)

  (b)

  (c)

  (d)

  (e)

  (f)

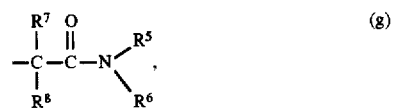  (g)

  (h)

In the above groups (a) to (h), $R^3$, $R^4$, $R^5$, $R^6$, $R^7$ and $R^8$ are as defined already.

In the above reaction scheme, Hal bonding to $Q^1$ is a halogen atom.

In the above reaction scheme, $R^1$, $R^2$, $X^1$, $X^2$, $X^3$, $X^4$, $X^5$, $X^6$, $X^7$, $X^8$, p and n are as defined already.

The above production method will be explained step by step hereinafter.

(Step 1)

A compound of the formula (II) and a compound of the formula (III) are reacted with each other in an inert solvent in the presence of a dehydrating agent such as DCC (N,N'-dicyclohexylcarbodiimide), CDI (1,1-carbonyldiimidazole) or EDC (1-(3-dimethylaminopropyl)-3-ethylcarbodiimide) and a base, to produce a pyrazole derivative of the formula (Ia).

The amount of the compound of the formula (III) is preferably 1.0–3.0 mol per mole of the compound of the formula (II). Further, the amount of the dehydrating agent is preferably 1.0–1.5 mol per mole of the compound of the formula (II). The base is not specially limited in kind, while potassium carbonate or sodium carbonate is preferred. The amount of the base is preferably 0.5 to 2.0 mol per mole of the compound of the formula (II). The solvent for the reaction is not specially limited if it is inert to the reaction. The solvent is preferably selected from acetonitrile, 1,4-dioxane, t-amyl alcohol, t-butyl alcohol and i-propyl alcohol. The reaction temperature can be selected from the range of from 0° C. to the boiling point of the solvent, while it is preferably about 80° C. The reaction time is 1–48 hours, while it is generally about 8 hours.

An ester is formed as a reaction intermediate, and this ester intermediate can be isolated by means such as silica gel column chromatography, while the reaction is generally proceeded with without isolating the ester intermediate. When the ester intermediate is isolated, a base is added to the ester intermediate to further proceed with the reaction, whereby the intended pyrazole derivative (Ia) can be obtained. The amount of the base used in this case is 0.5 to 3.0 equivalents, preferably 0.5 to 1.5 equivalents, based on the ester intermediate. The reaction temperature is generally 80°–150° C., preferably 100°–120° C. The reaction time is generally 0.5 to 8 hours, preferably approximately 1 to 2 hours.

After the completion of the reaction, according to a conventional method, the solvent is distilled off, the residue is liquid-separated with an organic solvent and water, the aqueous layer is neutralized with an acid such as hydrochloric acid and extracted with ethyl acetate, the organic layer is dried over a dehydrating agent such as anhydrous sodium sulfate, and the solvent is distilled off, whereby the intended pyrazole derivative (Ia) can be obtained.

(Step 2)

The compound (Ia) obtained in step 1 is reacted with $Q^1$-Hal (IV) (in which $Q^1$ and Hal are as defined already) in an inert solvent in the presence of a base, to produce a compound (Id).

In this step, the compound (Ia) :compound (IV) molar ratio is preferably 1:1–1:3. For collecting hydrogen halide byproducted by the reaction, preferably, a base such as sodium carbonate, potassium carbonate, triethylamine or pyridine is used in at least an equimolar amount based on the starting material of the formula (Ia). The reaction temperature is preferably set in the range of from room temperature to the boiling point of the solvent. The solvent used in the reaction includes aromatic hydrocarbons such as benzene and toluene, ethers such as diethyl ether, ketones such as methyl ethyl ketone and halogenated hydrocarbons such as methylene chloride and chloroform. A two-phase solvent consisting of the above solvent and water may be also used. In this case, a more desirable result can be obtained by adding a phase-transfer catalyst such as crown ether or benzyltriethylammonium chloride to the reaction system.

After the completion of the reaction, according to a conventional method, the reaction mixture is liquid-separated, the end product is extracted from the aqueous layer by means of an organic solvent such as dichloromethane, the organic layer is dehydrated and then solvent is distilled off, whereby the intended pyrazole derivative (Id) can be isolated.

In the reaction above, the pyrazole compound represented by the formula (II) which is used as the reaction reagent can be synthesized by the method disclosed in JP-A-61-257974.

In the above method, the compound of the general formula (III) is reacted with the aromatic carboxylic acid of the general formula (II),

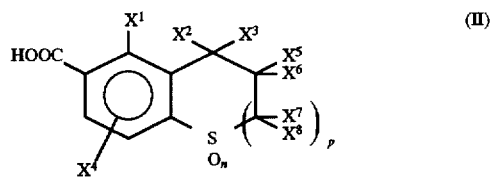

(II)

wherein $X^1$ is one member selected from the group consisting of a $C_1$–$C_4$ alkyl group, halogen atom, a $C_1$–$C_4$ haloalkyl group, a $C_2$–$C_4$ alkoxyalkyl group, a $C_1$–$C_4$ alkoxy group and a $C_1$–$C_4$ haloalkoxy group, each of $X^2$ and $X^3$ is independently one member selected from the group consisting of hydrogen atom, a $C_1$–$C_4$ alkyl group and a $C_1$–$C_4$ haloalkyl group, $X^4$ is one member selected from the group consisting of hydrogen atom, halogen atom, a $C_1$–$C_4$ alkyl group, a $C_1$–$C_4$ haloalkyl group and a $C_1$–$C_4$ alkoxy group, each of $X^5$, $X^6$, $X^7$ and $X^8$ is independently hydrogen atom or a $C_1$–$C_4$ alkyl group, a combination of $X^2$ and $X^5$ or a combination of $X^5$ and $X^7$ may form an unsaturated bond, p is an integer of 0 or 1, and n is an integer of 0, 1 or 2.

The above aromatic carboxylic acid of the general formula (II) is a novel compound disclosed in no literature, and it is useful as an intermediate for the production of the pyrazole derivative of the present invention.

Specific examples of $X^1$, $X^2$, $X^3$, $X^4$, $X^5$, $X^6$, $X^7$ and $X^8$ in the formula (II) include those described concerning the pyrazole derivative of the above formula (I).

The aromatic carboxylic acid derivative of the formula (II) is an acidic substance, and can be easily converted to a salt by treating it with a base. This salt is also included in the aromatic carboxylic acid derivative of the present invention. The base can be selected from known bases without any limitation. For example, the base includes organic bases such as amines and anilines and inorganic bases such as sodium compounds and potassium compounds. The amines include monoalkylamine, dialkylamine and trialkylamine. The alkyl group of the alkylamines is generally a $C_1$–$C_4$ alkyl group. The anilines include aniline, monoalkylaniline and dialkylaniline. The alkyl group of the alkylalines is generally a $C_1$–$C_4$ alkyl group. The sodium compounds include sodium hydroxide and sodium carbonate, and the potassium compounds include potassium hydroxide and potassium carbonate.

The aromatic carboxylic acid derivative of the general formula (II) in which p is 1 (wherein $X^2$ and $X^5$ do not bond to each other, nor do $X^5$ and $X^7$ bond to each other) can be produced by methods shown in the following reaction schemes 1–5.

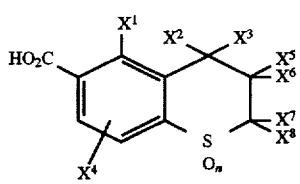

Production Scheme 1

Production scheme 1 shows a method of producing an aromatic carboxylic acid derivative of the general formula (IIx) in which $X^6$ is hydrogen.

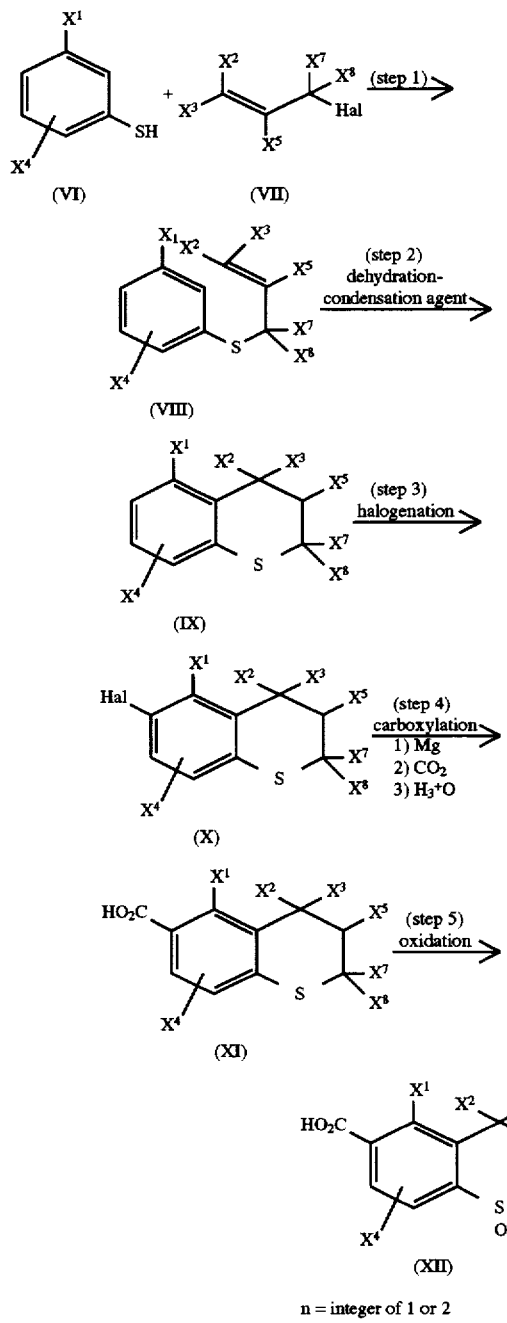

n = integer of 1 or 2

In the above production scheme, $X^1$, $X^2$, $X^3$, $X^4$, $X^5$, $X^6$, $X^7$, $X^8$ and Hal are as defined above.

Thiophenol of the formula (VI) as a starting material can be obtained by a known method (e.g., "Shin-Jikken Kagaku Koza 14, Syntheses and Reactions of Organic Compounds, III, page 1,704, chap. 8.1, Thiols, f. Synthesis through dithiocarbonate ester", Maruzen, issued Feb. 22, 1986).

(Step 1)

The starting material of the formula (VI) and a compound of the formula (VII) are reacted with each other in an inert solvent such as acetone, diethyl ether or dimethylformamide in the presence of a base such as anhydrous potassium carbonate, sodium hydroxide, potassium hydroxide, anhydrous sodium carbonate or triethylamine, to obtain a compound of the formula (VIII). The compound of the formula (VII) and the base are used in amounts of 1.0–1.5 mol equivalent and 1.0–1.5 mol equivalent, respectively, based on the starting material of the formula (VI). Generally, the reaction temperature is preferably approximately 0°–80° C., and the reaction time is preferably approximately 1–8 hours.

(Step 2)

The compound of the formula (VIII) is ring-closed or cyclized by adding a dehydration-condensation agent such as a polyphosphoric acid, sulfuric acid or phosphorus pentoxide to obtain a compound of the formula (IX) (thiochroman compound). The amount of the dehydration-condensation agent is 1–10 mol equivalent based on the compound of the formula (VIII). Generally, the reaction temperature is preferably approximately 0°–100° C., and the reaction time is preferably approximately 1–8 hours.

(Step 3)

A halogenation reagent such as bromine, sulfuryl chloride or chlorine is reacted with the compound of the formula (IX) in the presence of a solvent such as methylene chloride, chloroform or carbon tetrachloride, to obtain a compound of the formula (X) in which a halogen is substituted on the 6-position. Generally, the reaction temperature is preferably approximately 0°–80° C., and the reaction time is preferably approximately 1–80 hours.

(Step 4)

The compound of the formula (X) is reacted with magnesium (Mg) to form a Grignard reagent, and carbon dioxide ($CO_2$) is reacted therewith to obtain a compound (XI) (n=0, sulfide compound) which is an aromatic carboxylic acid derivative of the formula (IIx) in which a carboxyl group is introduced onto the 6-position, provided by the present invention. The solvent is preferably selected from ethers such as diethyl ether and tetrahydrofuran. The reaction temperature is preferably 0°–70° C., particularly preferably 20°–60° C. The reaction time is generally approximately 1–7 hours.

The amount of magnesium (Mg) for obtaining the Grignard reagent is preferably 1.1–3.5 mol equivalent based on the compound of the formula (X). The Grignard reaction is preferably carried out in the copresence of alkyl iodide such as methyl iodide or alkyl bromide such as ethyl bromide, since the reaction proceeds smoothly. The amount of the halogenated alkyl used in this case is preferably 0.1–2.5 mol equivalent based on the compound of the formula (X).

The reaction between the Grignard reagent and carbon dioxide ($CO_2$) is carried out by introducing carbon dioxide from a gas container into the Grignard reagent or by introducing carbon dioxide generated from dry ice (solid carbon dioxide) into the Grignard reagent. Dry ice may be directly added to the Grignard reagent for the reaction.

(Step 5)

An oxidizing agent (e.g., hydrogen peroxide, peracetic acid or sodium metaperiodate) is reacted with the compound of the formula (XI) (a compound of the formula (IIx) in which n=0, sulfide compound) in a solvent (e.g., acetic acid, water or methanol), to obtain a compound (XII) (n=1, sulfoxide compound/n=2, sulfone compound) which is an aromatic carboxylic acid derivative of the formula (IIx) provided by the present invention. When the compound (XI) is reacted with 1 equivalent of the oxidizing agent, a sulfoxide (a compound (XII) in which n=1) is obtained. When the compound (XI) is reacted with 2 equivalents of the oxidizing agent, a sulfone (a compound (XII) in which n=2) is obtained.

Production Scheme 2

Production scheme 2 also shows a method of producing an aromatic carboxylic acid derivative of the general formula (IIx) in which $X^6$ is hydrogen.

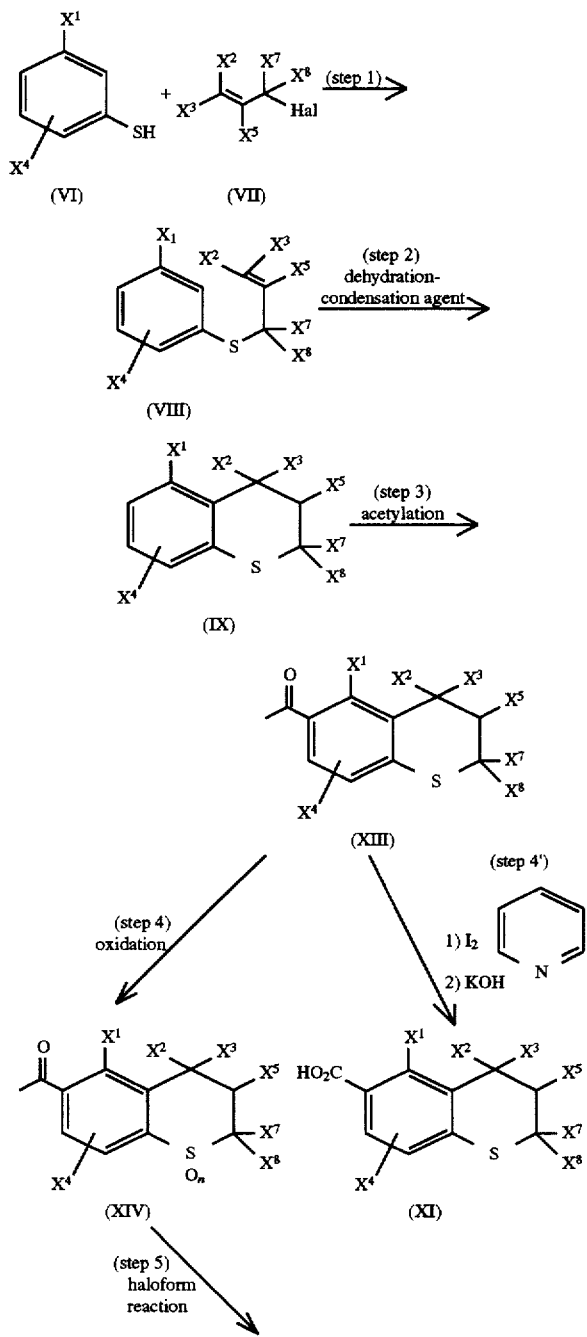

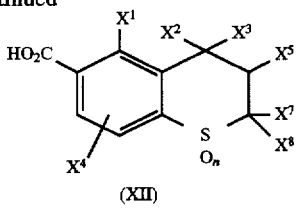

(Steps 1 and 2)

The steps 1 and 2 of producing a compound (IX) from a starting material (VI) through a compound (VIII) are the same as those in the production of the compound (IX) from the compound (VI) in the scheme 1.

(Step 3)

A Lewis acid such as aluminum chloride, zinc chloride or iron chloride or a proton acid such as hydrogen fluoride, sulfuric acid or phosphoric acid, and acetyl chloride, are reacted with the compound of the formula (IX) in the presence of a solvent such as dichloromethane, nitromethane, acetonitrile or benzene, to obtain a compound (XIII) having an acetyl group introduced onto its 6-position. The amount of the Lewis acid or the proton acid is 1.0–1.5 mol equivalent based on the compound of the formula (IX), and the amount of the acetyl chloride is 1.0–1.5 mol equivalent based on the compound of the formula (IX). Generally, the reaction temperature is preferably approximately 0°–80° C., and the reaction time is preferably approximately 1–8 hours.

(Step 4)

An oxidizing agent (e.g., hydrogen peroxide, peracetic acid or sodium metaperiodate) is reacted with the compound (XIII) (sulfide) in a solvent (e.g., acetic acid, water or methanol), to obtain a compound (XIV) (n=1, sulfoxide compound/n=2, sulfone compound). When the compound (XIII) is reacted with 1 equivalent of the oxidizing agent, a sulfoxide compound (a compound (XIV) in which n=1) is obtained. When the compound (XIII) is reacted with 2 equivalents of the oxidizing agent, a sulfone compound (a compound (XIV) in which n=2) is obtained.

(Step 4')

The method of converting a methyl ketone group (acetyl group) on the 6-position to a carboxyl group without oxidizing the sulfur atom S of a thiochroman ring is disclosed in J. Am. Chem. Soc. 66, page 1,612 (1944). That is, the methyl ketone compound of the formula (XIII) is reacted with iodine in pyridine and then decomposed with an alkali, whereby a compound (XI) (n=0, sulfide compound) which is an aromatic carboxylic acid derivative of the formula (IIX) provided by the present invention is obtained.

(Step 5)

The methyl ketone compound (XIV) is converted to a compound (XII) (n=1, sulfoxide compound/n=2, sulfone compound) which is an aromatic carboxylic acid derivative (IIx) of the present invention, by reacting the methyl ketone compound (XIV) in a haloform reaction in the presence of an oxidizing agent (e.g., permanganate, chromic acid, halogen, oxygen or sulfuric acid).

The aromatic carboxylic acid derivative of the general formula (IIx) can be generally produced by the following production scheme 3.

Production Scheme 3

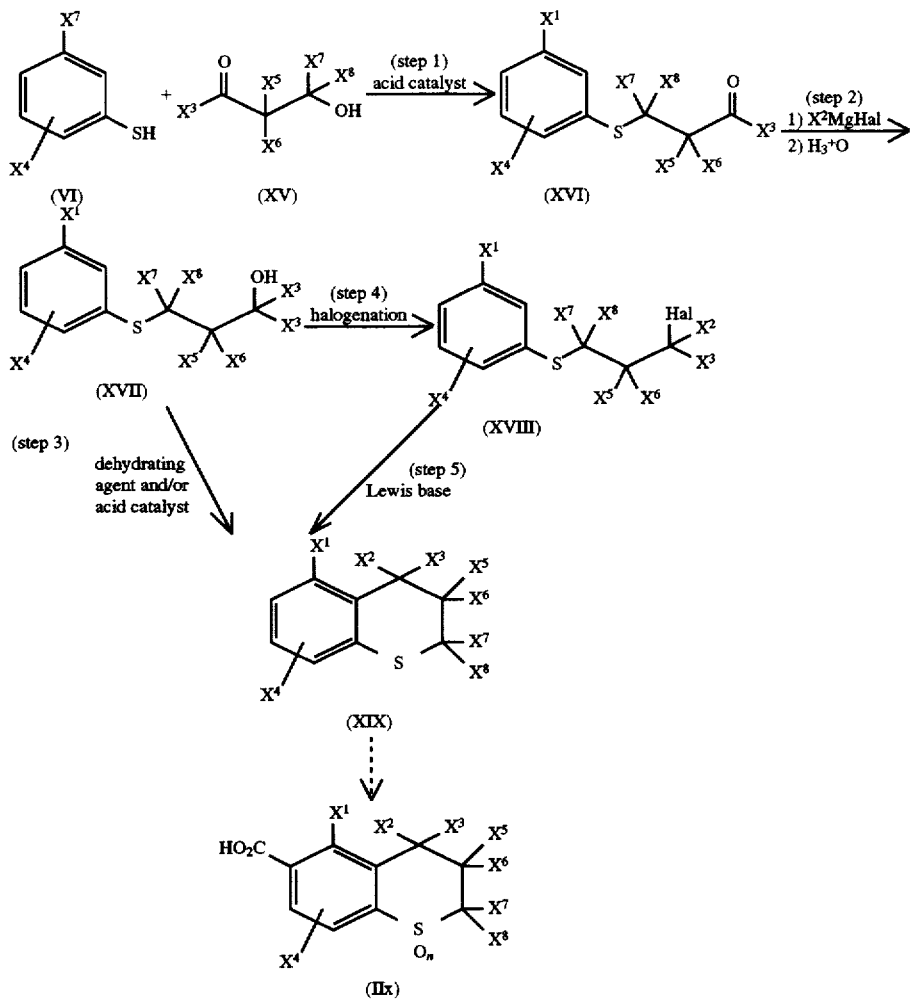

(Step 1)

Thiophenol of the formula (VI) is reacted with an alcohol of the formula (XV) in an aromatic solvent such as benzene or toluene or a halogenated hydrocarbon solvent such as dichloroethane or tetrachloroethane in the presence of an acid catalyst such as sulfuric acid, p-toluenesulfonic acid, methanesulfonic acid, formic acid or acetic acid, to obtain a compound of the formula (XVI). The amount of the alcohol of the formula (XV) is 1.0–3.0 mol equivalent based on the thiophenol of the formula (VI). The amount of the acid catalyst is 0.01 to 1.0 mol equivalent based on the thiophenol. Acetic acid or formic acid may be used as a solvent as well. The reaction temperature can be set in the range of from room temperature to the boiling point of the solvent, while it is generally from 50° C. to 100° C.

(Step 2)

A Grignard reagent is reacted with the compound of the formula (XVI) to obtain an alcohol of the formula (XVII). The reaction in this step is a well-known Grignard reaction, and its details are omitted.

(Step 3)

This is a step in which a dehydrating agent such as polyphosphoric acid, diphosphorus pentoxide or sulfuric acid or an acid catalyst such as methanesulfonic acid or p-toluenesulfonic acid is reacted with the alcohol of the formula (XVII) to produce a compound of the formula (XIX). As a solvent, there may be used as an aromatic hydrocarbon such as benzene or toluene or a halogen-containing hydrocarbon solvent such as dichloroethane or tetrachloroethane. Polyphosphoric acid or sulfuric acid may be also used as a solvent as well. The reaction temperature can be set in the range of from room temperature to the boiling point of the solvent, while it is generally from 50° C. to 100° C.

(Step 4)

This is a step in which a halogenating agent such as thionyl chloride, phosphorus oxychloride or phosphorus pentachloride is reacted with the alcohol of the formula (XVII), to obtain a halogen compound of the formula (XVIII). The amount of the halogenating agent is 1.0–1.5 mol equivalent based on the alcohol of the formula (XVII). The solvent is not specially limited if it is inert to the reaction, while it is selected from those described in step 3. Thionyl chloride or phosphorus oxychloride may be used as a solvent. The reaction temperature can be set in the range of from room temperature to the boiling point of the solvent, while it is generally from 60° C. to 80° C.

(Step 5)

This is a step in which a Lewis acid such as aluminum chloride, zinc chloride or iron chloride is reacted with the halogen compound of the formula (XVIII), to produce a compound of the formula (XIX). Aluminum chloride is preferred. The amount of the Lewis acid is 1.0–1.5 mol equivalent based on the compound of the formula (XIX). As a solvent, preferred is a halogenated hydrocarbon solvent such as methylene chloride or dichloroethane. The reaction temperature can be set in the range of from 0° C. to the boiling point of the solvent, while the reaction generally proceeds smoothly around room temperature.

The compound of the formula (XIX) is produced by the above steps, and the procedures thereafter are carried out in the same manner as in Production scheme 1 or 2, to obtain an aromatic carboxylic acid of the general formula (IIx).

Production scheme 4

Production scheme 4 shows a method of producing an aromatic carboxylic acid derivative of the general formula (IIx) in which both $X^3$ and $X^5$ are hydrogen.

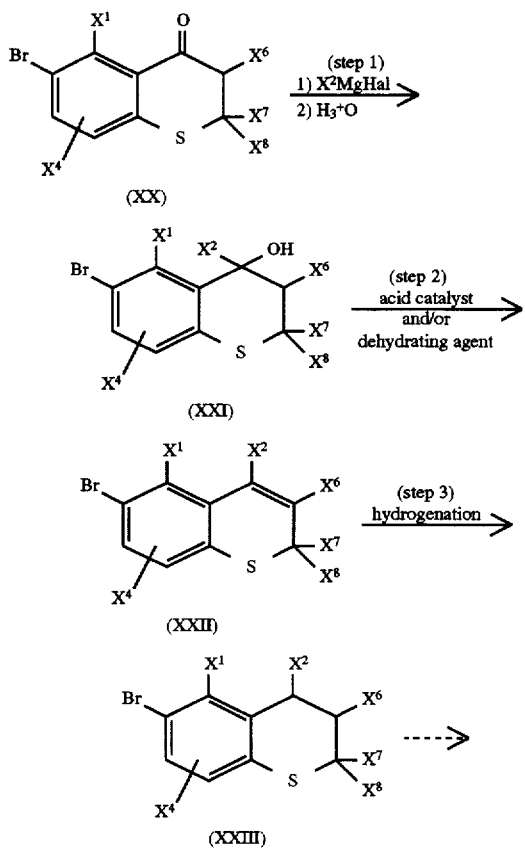

(Step 1)

A brominated thiochroman-4-one compound (XX) as a starting material can be produced by a known method, for example, a method disclosed in JP-A-58-198483 and International Laid-open Patent Publication W088/06155. A Grignard reagent is reacted with the brominated thiochroman-4-one compound of the formula (XX) to convert it into a thiochromanol derivative of the formula (XXI). The reaction in this step is a typical Grignard reaction and its details are omitted.

(Step 2)

This is a step in which the thiochromanol derivative of the formula (XXI) is dehydrated in an organic solvent in the presence of an acid catalyst, to form 3,4-dehydrothiochroman derivative of the formula (XXII). The acid catalyst is selected from sulfuric acid, p-toluenesulfonic acid, methanesulfonic acid and trifluoromethanesulfonic acid. The amount of the acid catalyst is 0.001–1.0 mol equivalent, preferably 0.01–0.1 mol equivalent, based on the thiochromanol derivative (XXI). The solvent includes aromatic hydrocarbon solvents such as benzene and toluene and halogenated hydrocarbon solvents such as 1,2-dichloroethane, 1,1,1-trichloroethane or carbon tetrachloride. The reaction temperature is generally 60°–120° C., preferably 80°–100° C.

(Step 3)

This is a step in which the 3,4-dehydrothiochroman derivative of the formula (XXII) is reduced to form a thiochroman derivative of the formula (XXIII). The reduction method is not specially limited, while the reduction is preferably carried out with hydrogen in the presence of a catalyst such as palladium or platinum under the conditions of atmospheric pressure or elevated pressure.

Thereafter, the same carboxylation and oxidation as those in the above Production scheme 1 are carried out to obtain an aromatic carboxylic acid of the general formula (IIx).

Production scheme 5

Production scheme 5 shows a method of producing an aromatic carboxylic acid derivative of the general formula (IIx) in which $X^5$ is hydrogen.

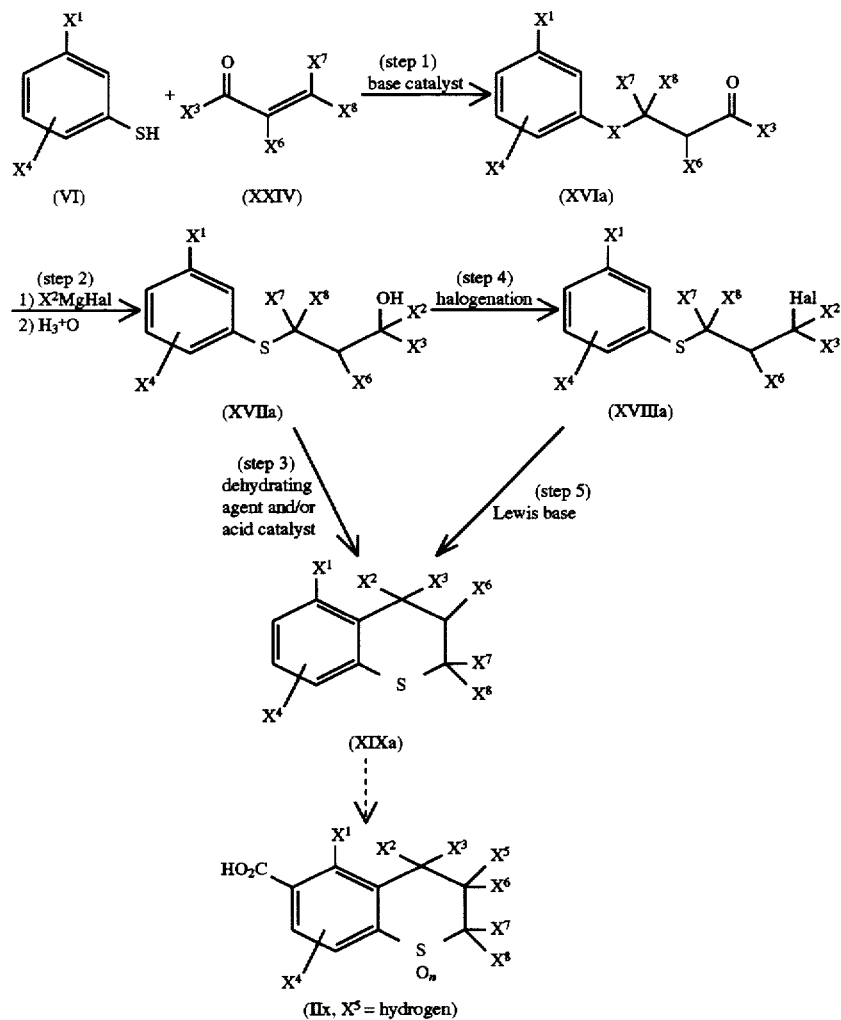

(Step 1)

The step is a step wherein a thiophenol of the formula (VI) and α,β-unsaturated ketone of the formula (XXIV) are reacted with each other in the presence of a basic catalyst such as pyridine, piperidine or triethylamine to form a sulfide of the formula (XVIa). The solvent used for the reaction is not specially limited if it is inert to the reaction. Preferred is a halogenated hydrocarbon solvent such as 1,2-dichloroethane, 1,1,1-trichloroethane or 1,1,2,2-tetrachloroethane. The reaction temperature can be set in the range of from room temperature to the boiling point of the solvent, while the reaction generally proceeds smoothly around room temperature. The amount of the α,β-unsaturated ketone of the formula (XXIV) is 1–5 mol, preferably 1.0–1.5 mol per mole of the thiophenol of the formula (VI).

Steps 2–5 hereinafter can be carried out in the same manner as in Scheme 3, and their details are omitted. Then, a compound (XIXa) obtained in the step 3 or 5 is reacted in the same manner as in the above Production scheme 1 or 2, to obtain an aromatic carboxylic acid derivative of the formula (IIx).

Production scheme 6

Production scheme 6 shows a method of producing an aromatic carboxylic acid derivative of the general formula (IIx) in which both $X^2$ and $X^5$ are hydrogen.

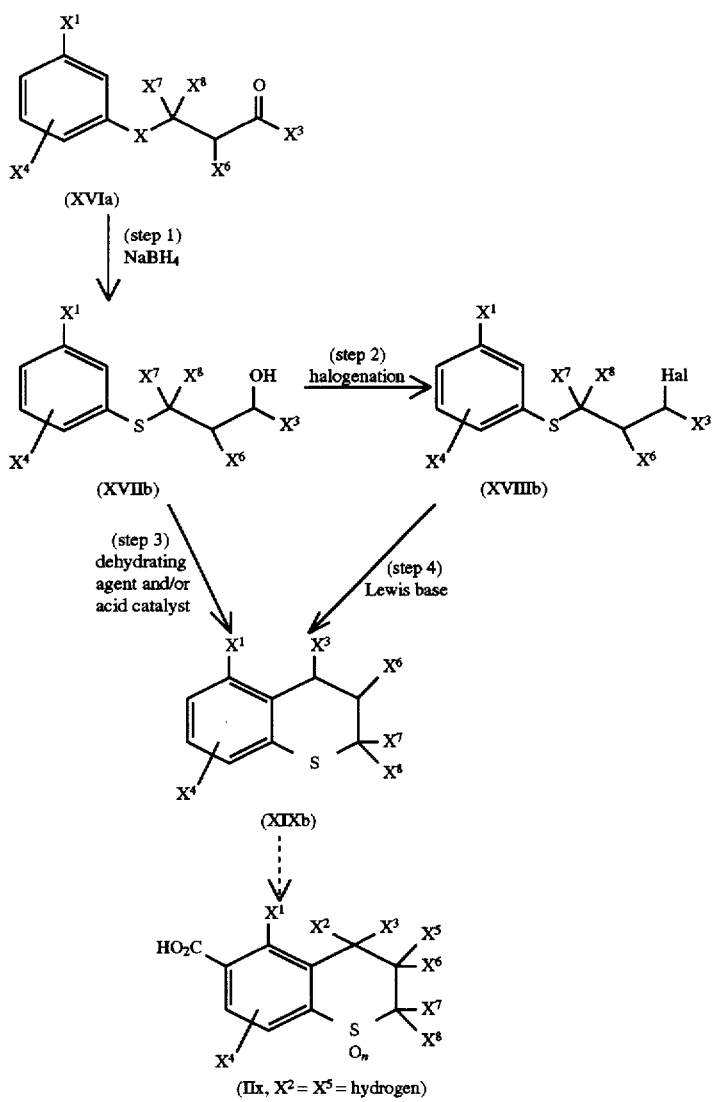

(Step 1)

The step is a step wherein the sulfide of the formula (XVIa), obtained in step 1 in the production scheme 5, is reduced to form an alcohol of the formula (XVIIb). The reducing agent for use is not much limited, while sodium borohydride is preferably used. The amount of the sodium borohydride is 0.25–1 mol equivalent based on the sulfide of the formula (XVIa). The solvent is preferably selected from alcohol solvents such as methanol and ethanol. Generally, the reaction proceeds smoothly when the reaction temperature is in the range of from 0° C. to room temperature, and no heating is particularly required.

The steps 2, 3 and 4 thereafter can be carried out in the same manner as in the steps 3, 4 and 5 in Production scheme 3, and their details are therefore omitted. Then, a compound (XIXb) obtained in the step 3 or 4 is reacted in the same manner as in Production scheme 1 or 2, to obtain an aromatic carboxylic acid derivative of the formula (IIx).

An aromatic carboxylic acid derivative of the general formula (II) in which p is 0 (provided that $X^2$ and $X^5$ do not bond to each other), i.e, an aromatic carboxylic acid derivative of the general formula (IIy), is produced by any one of methods in the following Production scheme 7–10.

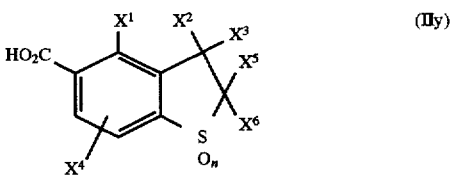

Production scheme 7

Production scheme 7 shows a method of producing an aromatic carboxylic acid derivative of the general formula (IIy) in which $X^2$ is methyl.

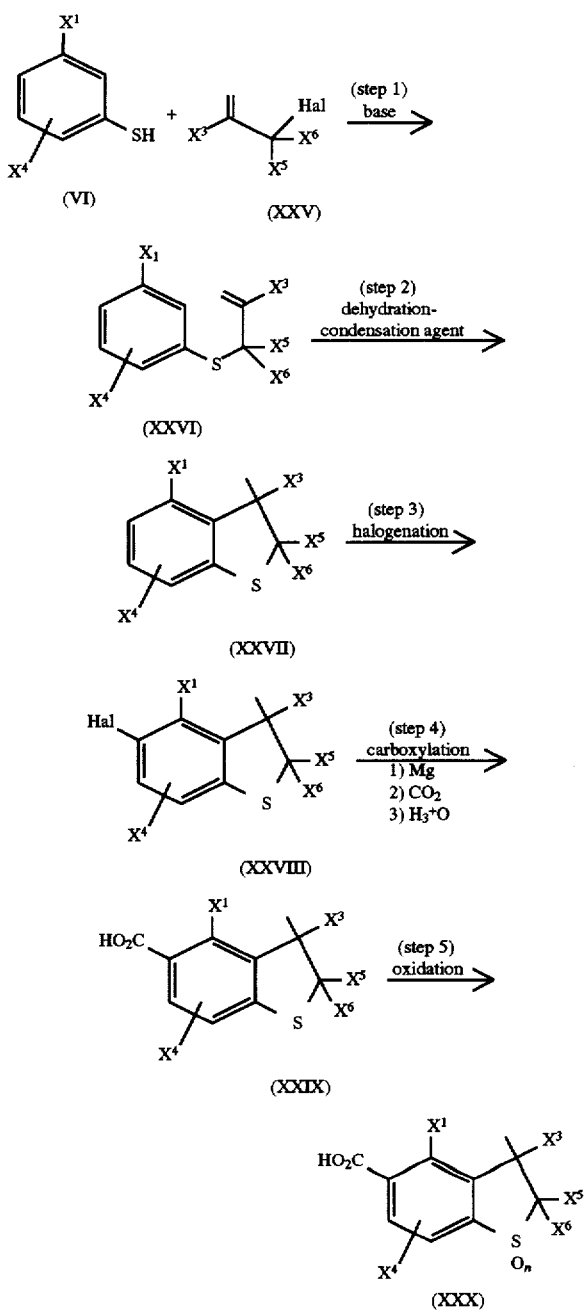

(Step 1)

Step 1 is directed to a reaction in which a substituted thiphenol (VI) is reacted with a halogenated olefin (XXV) as an alkylating agent in the presence of a base, to obtain an alkyl-substituted thiophenol (XXVI).

The base used in the above reaction is selected from inorganic bases such as anhydrous potassium carbonate, sodium hydroxide and potassium hydroxide and organic bases such as triethylamine, while preferred is anhydrous potassium carbonate. The amount of the base is generally 0.5–3.0 equivalents, preferably 1.0–1.2 equivalents, based on the substituted thiophenol (VI).

The amount of the halogenated olefin (XXV) used as an alkylating agent in the above reaction is generally 1.0–2.0 equivalents, preferably 1.0–1.2 equivalents, based on the substituted thiophenol (VI).

Any solvent is used for the reaction without any special limitation if it is inert to the reaction, while acetone or dimethylformamide (DMF) is preferred. The reaction time is 10 minutes–8 hours, while it is generally completed in about 2 hours. The reaction temperature can be set in the range of 0° C.—the reflux temperature, while the range of from room temperature to 60° C. is preferred.

After the completion of the reaction, the reaction mixture is cooled, insolubles are removed, and the solvent is distilled off. The residue is re-dispersed in an organic solvent such as hexane, washed and dried, and the solvent is distilled off, whereby the alkyl-substituted thiophenol (XXVI) can be isolated.

(Step 2)

The step 2 is directed to a reaction for cyclizing the alkyl-substituted thiophenol (XVII) by an intra-molecular Friedel-Crafts reaction in the presence of a dehydration-condensation agent, to form a hydrobenzo[b]thiophene compound (XXVII).

The dehydration-condensation agent used in the above reaction is selected, for example, from sulfuric acid, phosphoric acid, phosphorus pentoxide and polyphosphoric acid, and polyphosphoric acid is preferred. The amount of the dehydration-condensation agent is generally 1–10 mol equivalent based on the alkyl-substituted thiophenol (XXVI).

The reaction temperature is in the range of from room temperature to 200° C., while it is generally preferably 100° to 150° C. The reaction time is 30 minutes to 16 hours, while it is generally preferably 2 to 8 hours.

After the completion of the reaction, the reaction mixture is poured into ice water, a solvent such as hexane is added, and the mixture is liquid-separated. The resultant organic layer is washed and dehydrated, and then the solvent is distilled off. The resultant residue is purified by means such as column chromatography using a developer solvent such as hexane, whereby the hydrobenzo[b]thiophene compound (XXVII) can be isolated.

(Step 3)

The step 3 is directed to a reaction for obtaining a halogenated benzo[b]thiophene compound (XXVIII) in which a halogen is substituted on the 5-position of the benzo[b]thiophene ring, by reacting the hydrobenzo[b]thiophene compound (XXVII) with a halogenating reagent such as bromine, sulfuryl chloride or chlorine in the presence of a solvent such as methylene chloride, chloroform or carbon tetrachloride.

The amount of the halogenating reagent used for the above reaction is generally 1.0–3.0 equivalents, preferably 1.0–1.5 equivalents, based on the hydrobenzo[b]thiophene compound (XXVIII). Preferably, the reaction temperature is generally 0°–80° C., and the reaction time is generally approximately 1–80 hours.

After the completion of the reaction, excessive halogenating reagent is removed with a sodium hydrogensulfite aqueous solution and the residue is worked up according to a conventional method, whereby the intended halogenated benzo[b]thiophene compound (XXVIII) can be isolated.

(Step 4)

The step 4 is directed to a reaction for obtaining an aromatic carboxylic acid derivative of the formula (IIy) in which a carboxyl group is introduced onto the 5-position of a hydrobenzo[b]thiophene ring, a compound (XXIX) (n=0, sulfide compound), by reacting the halogenated benzo[b]thiophene (XXVIII) with magnesium (Mg) to form a Grignard reagent and reacting the Grignard reagent with carbon dioxide ($CO_2$). It is preferred to use an ether such as diethyl ether or tetrahydrofuran as a solvent. The reaction temperature is 0°–70° C., particularly preferably 20°–60° C. The reaction time is generally approximately 1–7 hours.

The amount of magnesium (Mg) for obtaining the Grignard reagent is preferably 1.1–3.5 mol equivalent based on the halogenated hydrobenzo[b]thiophene compound (XXVIII). The Grignard reaction is preferably carried out in the co-presence of alkyl iodide such as methyl iodide or alkyl bromide such as ethyl bromide, since the reaction proceeds smoothly. The amount of the alkyl halide used in this case is preferably 0.1–2.5 mol equivalent based on the halogenated hydrobenzo[b]thiophene compound (XXVIII).

The reaction between the Grignard reagent and carbon dioxide ($CO_2$) is carried out by introducing carbon dioxide gas from a gas container into the Grignard reagent in a solvent or by introducing carbon dioxide gas generated from dry ice (solid carbon dioxide). The reaction may be carried out by adding dry ice directly to the Grignard reagent.

After the reaction, an acid such as hydrochloric acid is added to the reaction mixture to terminate the reaction, the reaction mixture is liquid-separated by adding an organic solvent such as ethyl acetate, the resultant organic layer is liquid-separated by adding an alkali such as a potassium carbonate aqueous solution, and the resultant aqueous layer is neutralized with an acid such as hydrochloric acid and extracted with an organic solvent such as ethyl acetate. The resultant organic layer is washed and dried and then the solvent is distilled off, whereby the aromatic carboxylic acid derivative of the formula (IIy), a compound (XXIX) (n=0, sulfide), can be isolated.

(Step 5)

The step 5 is directed to a reaction for obtaining an aromatic carboxylic acid derivative of the formula (IIy), a compound (XXX) (n=1, sulfoxide, n=2, sulfone), by reacting an oxidizing agent (e.g., hydrogen peroxide, peracetic acid or sodium metaperiodate) with the compound of the formula (XXIX) in a solvent (e.g., acetic acid, water or methanol).

When the oxidizing agent in an amount of 1 equivalent based on the compound (XXIX) is reacted, a sulfoxide (a compound of the formula (IIy) in which n=1) is obtained. When the oxidizing agent in an amount of at least 2 equivalents based on the compound (XXIX) is reacted, a sulfone (a compound of the formula (IIy) in which n=2) is obtained.

In the above reaction, the reaction temperature is generally 25°–110° C., preferably 60°–100° C. The reaction time is generally 30 minutes–8 hours, preferably 1–3 hours.

After the completion of the reaction, the reaction mixture is poured into a sodium hydrogensulfite aqueous solution and the mixture is liquid-separated by adding an organic solvent such as ethyl acetate. The resultant organic layer is washed and dried, and then the solvent is distilled off, whereby the intended compound of the formula (XXX) can be isolated.

Production scheme 8

The production scheme 8 also shows a method of producing an aromatic carboxylic acid derivative of the general formula (IIy) in which $X^2$ is methyl.

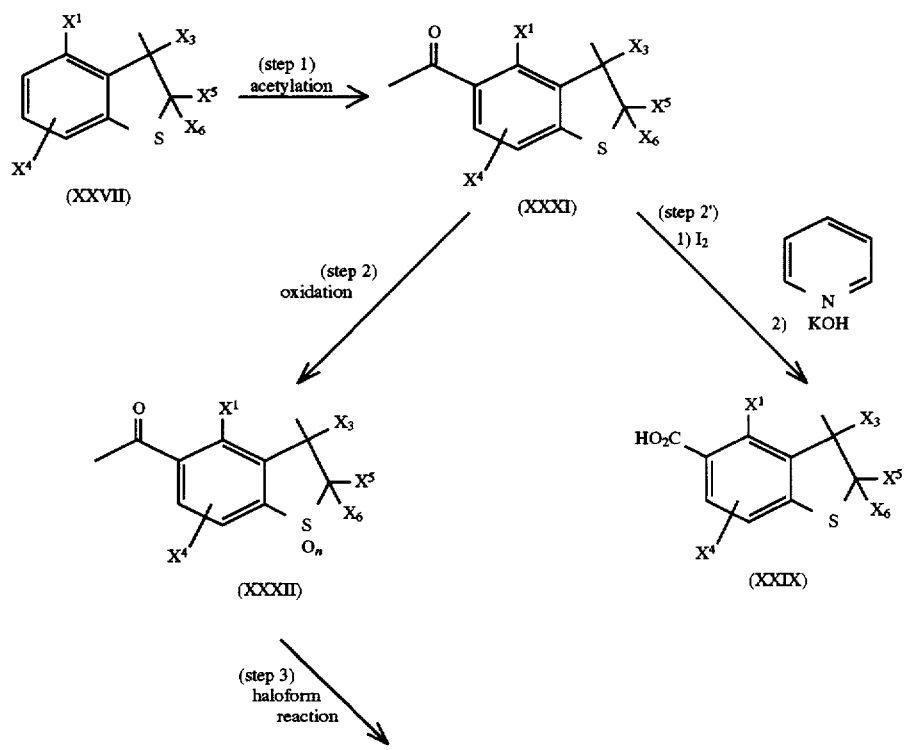

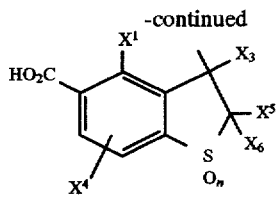

(XXX)

A hydrobenzo[b]thiophene compound of the formula (XXVII) as a starting material is obtained by steps 1 and 2 in Production scheme 7. Reactions in steps 1, 2, 2' and 3 are essentially the same as those in steps 3, 4, 4' and 5 in Production scheme 2, and their details are therefore omitted.

Production scheme 9

Production scheme 9 shows a method of producing an aromatic carboxylic acid derivative of the general formula (IIy) in which both $X^2$ and $X^6$ are hydrogen.

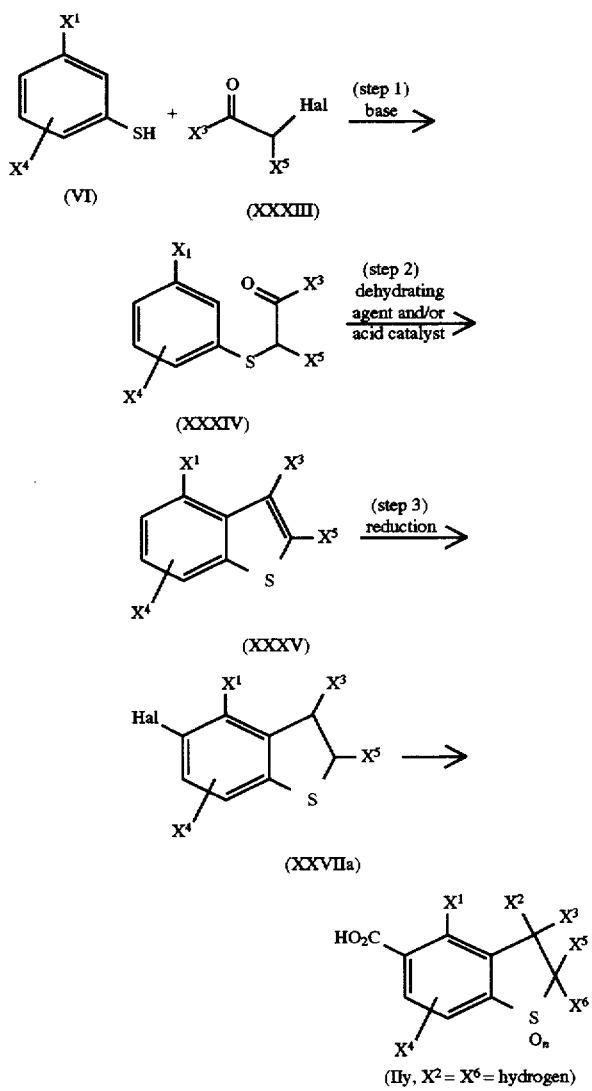

(Step 1)

The step 1 is directed to a reaction for obtaining a compound of the formula (XXXIV) by condensing the substituted thiophenol (VI) and an a-halo-carbonyl compound (XXXIII) in the presence of a base.

The base used in the above reaction is selected from inorganic bases such as anhydrous potassium carbonate, sodium hydroxide and potassium hydroxide and organic bases such as triethylamine. Anhydrous potassium carbonate is preferred. The amount of the base is generally 0.5–3.0 mol equivalent, preferably 1.0–1.2 mol equivalent, based on the substituted thiophenol.

The amount of the α-halo-carbonyl compound (XXXIII) is generally 1.0–2.0 mol equivalent, properly 1.0–1.2 mol equivalent, based on the substituted thiophenol (VI).

Any solvent can be used without any special limitation if it is inert to the reaction, while it is proper to use acetone or dimethylformamide (DMF).

The reaction temperature can be set in the range of from 0° C. to the reflux temperature of the solvent, while the range of from room temperature to 60° C. is preferred. The reaction time is 10 minutes to 8 hours, while the reaction is generally completed in about 2 hours.

After the completion of the reaction, the reaction mixture is cooled, insolubles are removed and the solvent is distilled off. The resultant residue is re-dispersed in a solvent such as hexane, washed and dried, and the solvent is distilled of, whereby the compound (XXXIV) can be isolated.

(Step 2)

The step 2 is directed to a reaction for forming a benzo[b]thiophene compound (XXXV) by subjecting the compound (XXXIV) obtained in step 1 to an intra-molecular dehydration-condensation reaction in the presence of a dehydrating agent and/or an acid catalyst.

The dehydrating agent used in the above reaction includes sulfuric acid, phosphoric acid, phosphorus pentoxide and polyphosphoric acid, and polyphosphoric acid is preferred. The acid catalyst includes p-toluenesulfonic acid, methanesulfonic acid and trifluoromethanesulfonic acid, and trifluoromethanesulfonic acid is preferred. The amount of the dehydrating agent and/or the acid catalyst is generally 1–10 mol equivalent, preferably 1.0–3.0 mol equivalent, based on the compound (XXXIV).

The reaction temperature can be set in the range of from 0° C. to the reflux temperature of the solvent, while the range of from room temperature to 60° C. is generally preferred. The reaction time is 10 minutes to 8 hours, while the reaction is generally completed in about 2 hours.

After the completion of the reaction, according to a conventional method, the reaction mixture is poured into ice water, a precipitated white crystal is re-dispersed in an organic solvent such as n-hexane, the dispersion is washed and the then solvent is distilled off, whereby the benzo[b]thiophene compound (XXXV) can be isolated.

(Step 3)

The step 3 is directed to a reaction for obtaining a hydrobenzo[b]thiophene compound (XXVIIa) in which a double bond between the 2- and 3-positions of the thiophene ring is reduced, by reducing the benzo[b]thiophene compound (XXXV) obtained in step 2.

The method of the above reduction is not specially limited, while a method of the reduction with hydrogen in the presence of a catalyst such as palladium or platinum oxide under atmospheric pressure or elevated pressure is facile and preferred.

After the completion of the reaction, according to a conventional method, the catalyst is removed, and the solvent is distilled off, whereby the intended hydrobenzo[b]thiophene compound (XXVIIa) can be isolated.

A halogenation, a Grignard reaction and an oxidation thereafter can be accomplished in the same manner as in the steps 3, 4 and 5 in Production scheme 7, whereby the intended aromatic carboxylic acid derivative (IIy) can be obtained.

The aromatic carboxylic acid derivative of the general formula (IIy) can be generally produced by the method in the following Production scheme 10.

(Step 2)

This is a step in which a Grignard reagent is reacted with the sulfide of the formula (XXXIVa) obtained in step 1, to form an alcohol of the formula (XXXVI). The reaction in this step is a typical Grignard reaction, and its details are therefore omitted.

Steps 3, 4 and 5 thereafter can be carried out in the same manner as in the steps 3, 4 and 5 in Production scheme 4, and their details are therefore omitted. The procedures thereafter are carried out in the same manner as in the above Production scheme 7, to obtain the aromatic carboxylic acid derivative of the formula (IIy).

The aromatic carboxylic acid derivative of the general formula (II) in which $X^4$ is hydrogen can be produced by the following Production scheme 11.

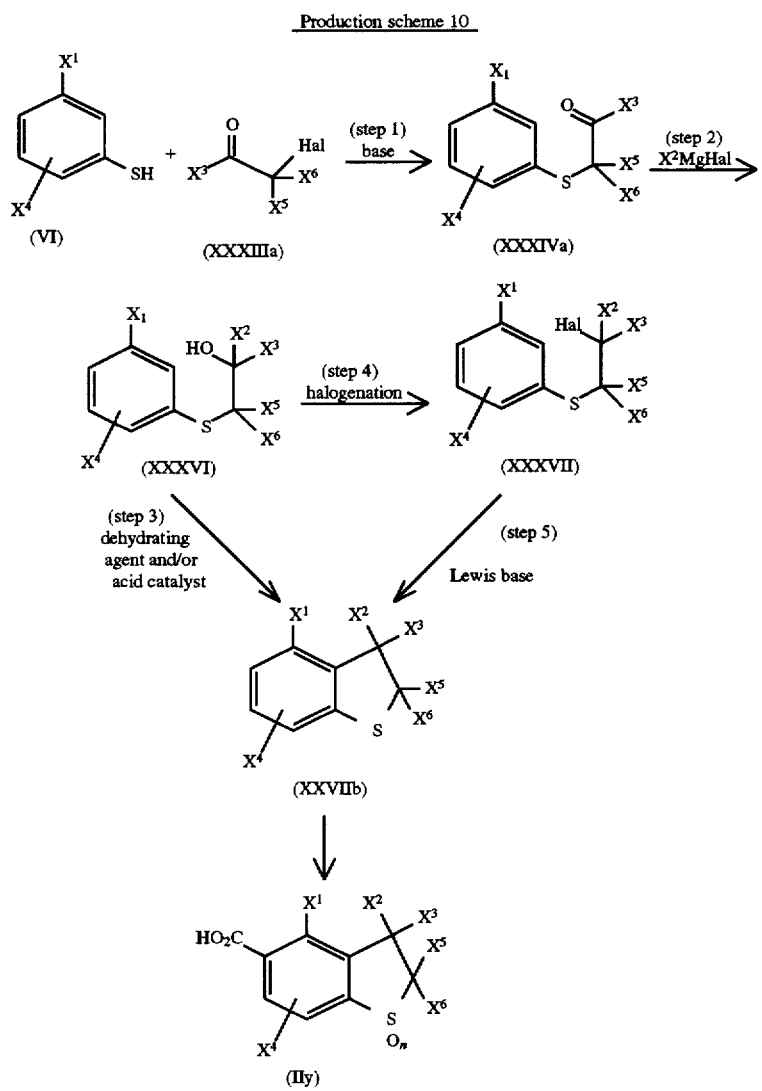

Production scheme 10

(Step 1)

A thiophenol of the formula (VI) and a ketone of the formula (XXXIIIa) are reacted with each other in the same manner as in the above Production scheme 9, to produce a sulfide of the formula (XXXIVa).

Production scheme 11

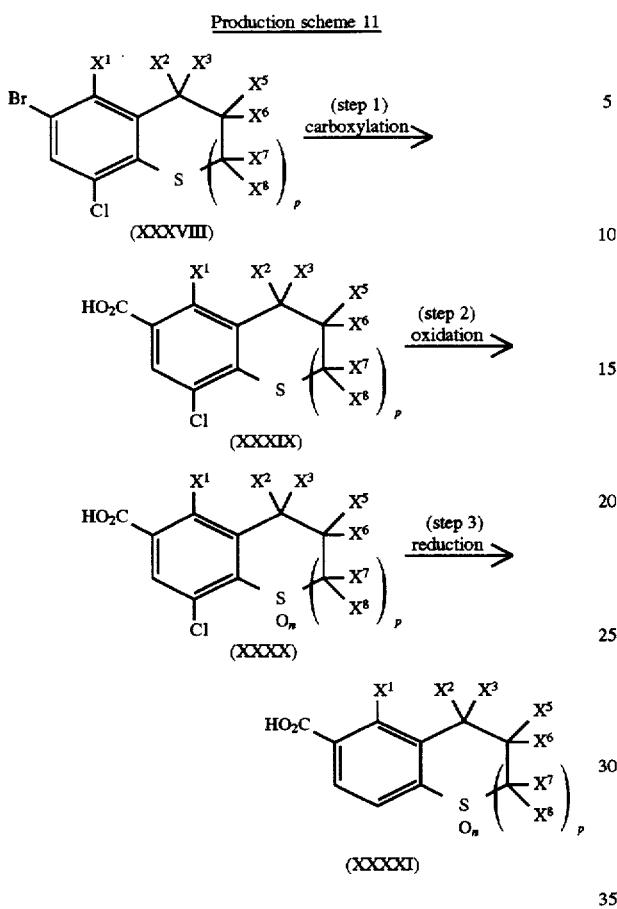

(Steps 1 and 2)

These are steps in which the starting material of the formula (XXXVIII) obtained in the steps 1-3 in Production scheme 1 or in the steps 1-3 in Production scheme 4 or 7 are treated in the same manner as in the steps 4 and 5 in Production scheme 1 through an aromatic carboxylic acid derivative of the formula (XXXIX) (n=0, sulfide compound), to form an aromatic carboxylic acid derivative of the formula (XXXX) (n=1, sulfone compound/n=2, sulfoxide compound). For details of these reactions, see the explanation of Production scheme 1.

(Step 3)

This is a step in which the compound of the formula (XXXX) is reduced to form an aromatic carboxylic acid derivative of the formula (XXXXI) (n=1 or 2). The reduction method is not specially limited. For example, there is a method in which the reduction is carried out with hydrogen having atmospheric pressure or elevated pressure in the presence of a catalyst such as palladium or platinum oxide, or it is directly carried out in the presence of zinc powder without using a catalyst. For accepting hydrogen chloride formed in the reaction, a base such as triethylamine, pyridine, sodium hydroxide or potassium hydroxide is allowed to be co-present in an amount equal to or greater than the equivalent weight based on the compound of the formula (XXXX). As a solvent, it is preferred to use an alcohol solvent such as methanol or ethanol. For fully dissolving the starting material, it is preferred to use ethanol having a water content of about 60%. The reaction temperature is generally 20°-120° C., and the reaction time is generally approximately 1-12 hours.

An aromatic carboxylic acid derivative of the formula (II) in which p is 1 and $X^2$ and $X^5$ together form a bond, i.e., a compound of the formula (IIza), is produced by the following Production scheme 12 or 13.

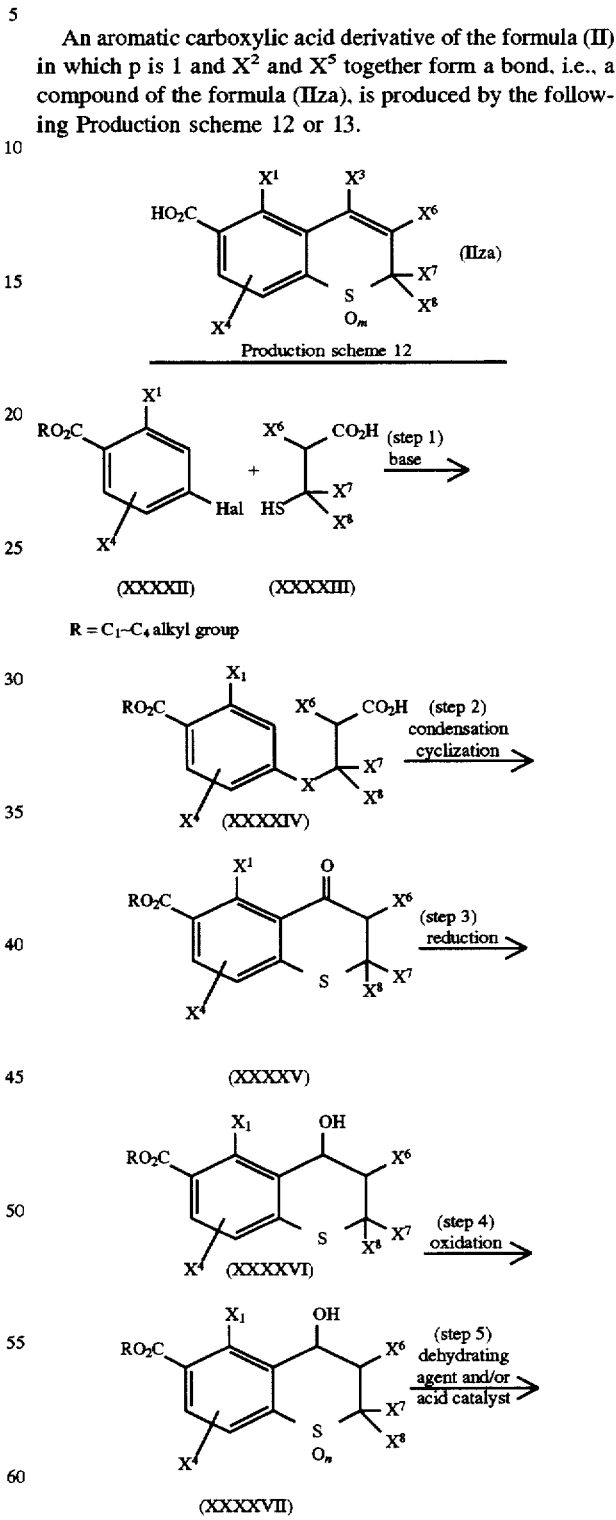

R = $C_1$-$C_4$ alkyl group

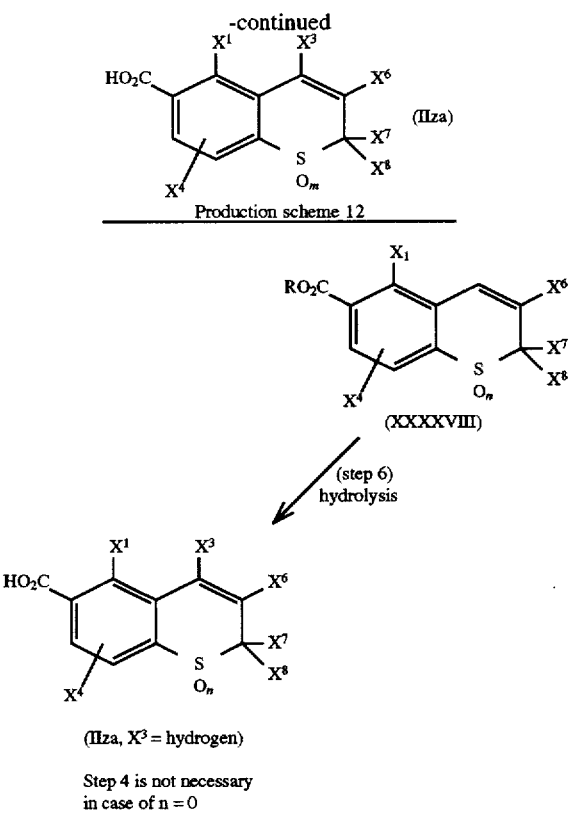

Production scheme 12

(IIza, X³ = hydrogen)

Step 4 is not necessary
in case of n = 0

(Step 1)

This is a step in which a benzoic acid ester of the formula (XXXXII) and a mercaptopropionic acid derivative of the formula (XXXXIII) are subjected to a condensation reaction to form a phenythiopropionic acid derivative of the formula (XXXXIV). This step is preferably carried out in an aprotic polar solvent such as N-methylpyrrolidone or N,N-dimethylformamide in the presence of a base. The base includes potassium carbonate and sodium carbonate. The amount of the base is 1.0–3.0 mol equivalent based on the benzoic acid ester. The reaction temperature can be set in the range of from room temperature to the boiling point of the solvent, while it is preferably 80° C. to 130° C. The reaction time is generally 1–8 hours.

(Step 2)

This is a step in which the phenylthiopropionic acid derivative (XXXXIV) obtained in step 1 is condensed and cyclized to form a thiochroman-4-one derivative of the formula (XXXXV).

The condensation method includes (i) a method in which the phenylthiopropionic acid derivative (XXXXIV) is dehydrated and cyclized in the presence of an acid catalyst such as hydrogen fluoride, sulfuric acid, phosphorus pentachloride, phosphoric acid, polyphosphoric acid, tin chloride, zinc chloride, aluminum chloride or Amberlite (trade name of an ion-exchange resin) and (ii) a method in which the phenylthiopropionic acid derivative (XXXXIV) is reacted with a chlorinating agent such as thionyl chloride to form an acid chloride and the acid chloride is cyclized in the presence of an acid catalyst similar to those used in the above method (i). The solvent used for the reaction is not specially limited if it is inert under reaction conditions, and it is preferably selected from hydrocarbon solvents such as pentane and hexane and halogen-containing solvents such as dichloromethane and 1,2-dichloroethane. It is also preferred to use polyphosphoric acid as both a solvent and an acid catalyst. In the above condensation cyclization method (i), the amount of the acid catalyst is 0.01–20 mol equivalent, preferably 1.0–10 mol equivalent, based on the phenylthiopropionic acid derivative (XXXXIV). The reaction temperature is generally in the range of from room temperature to 120° C., while it is preferably 50°–100° C. The reaction time is generally 30 minutes–8 hours, while it is preferably 30 minutes to 2 hours. In the above condensation cyclization method (ii), the amount of the chlorinating agent is 1.0–3.0 mol equivalent, preferably 1.1–1.5 mol equivalent, based on the phenylthiopropionic acid derivative (XXXXIV). The reaction temperature for the chlorination is generally in the range of from 0° to 120° C., preferably 30 minutes to 2 hours. The amount of the acid catalyst used in the cyclization method (ii) is 0.01–1.0 mol equivalent, preferably 0.1–1.0 mol equivalent, based on the acid chloride. The temperature for the reaction in the presence of the acid catalyst is generally room temperature to 120° C., preferably room temperature to 80° C. The reaction time is generally 30 minutes to 8 hours, preferably 2 to 4 hours.

(Step 3)

This is a step in which the thiochroman-4-one derivative (XXXXV) obtained in step 2 is reduced to obtain a hydroxythiochroman derivative of the formula (XXXXVI).

The reduction method is not specially limited, and for example, the reduction is carried out (i) by a method using a reducing agent such as sodium borohydride in a solvent inert to the reaction such as an alcohol or dichloromethane or (ii) by a method of hydrogenation under atmospheric pressure or elevated pressure in the presence of a reducing catalyst such as palladium or nickel. In the above reduction method (i), the amount of the reducing agent is 1.0–5.0 mol equivalent, preferably 1.1–2.0 mol equivalent, based on the thiochroman-4-one derivative (XXXXV). The reaction temperature is generally −20°–50° C., preferably 0°–20° C. The reaction time is generally 30 minutes to 8 hours, preferably 30 minutes to 2 hours. In the above reduction method (ii), the amount of the reducing catalyst is 1–50% by weight, preferably 10–20% by weight, based on the thiochroman-4-one derivative (XXXXV). The pressure of the hydrogen is generally atmospheric pressure—100 kg/cm², preferably 10–50 kg/cm². The reaction temperature is room temperature to 100° C., and the reaction time is 1 to 8 hours.

In a preferred embodiment of the step 3, the reduction is carried out in a solvent such as ethanol or dichloroethane in the presence of sodium borohydride. In this preferred embodiment, preferably, the reaction temperature is 0° C. to room temperature and the reaction time is 30 minutes to 2 hours.

When the reduction is carried out in the presence of sodium borohydride, the reaction mixture after the completion of the reaction is poured into ice water, and dichloromethane is added for extraction. The resultant organic layer is washed with a saturated sodium chloride aqueous solution and dried over anhydrous sodium sulfate and the solvent is distilled off, to give a crude product. The crude product is can be directly fed to the subsequent reaction without its purification.

(Step 4)

The step 4 is a step in which the hydroxythiochroman derivative (XXXXVI) obtained in step 3 is oxidized to obtain hydroxythiochroman oxide (XXXXVII), while this oxidation is basically the same as the oxidation in the step 5 in the Production scheme 1 and can be carried out according thereto. Details of this oxidation are therefore omitted.

(Step 5)

The step 5 is a step in which the hydroxythiochroman oxide (XXXXVII) obtained in step 4 is dehydrated to obtain a 3,4-dehydrothiochroman (XXXXVIII), while this dehydration is basically the same as the dehydration in the step 2 in the Production scheme 4 and can be carried out according thereto. Details of this dehydration are therefore omitted.

(Step 6)

The step 6 is a step in which the 3,4-dehydrothiochroman (XXXXVIII) obtained instep 5 is hydrolyzed to obtain the intended aromatic carboxylic acid (IIza, $X^3$=hydrogen). This hydrolysis is well known hydrolysis of an ester, and its details are therefore omitted. This step 6 may be carried out prior to step 4 or step 5.

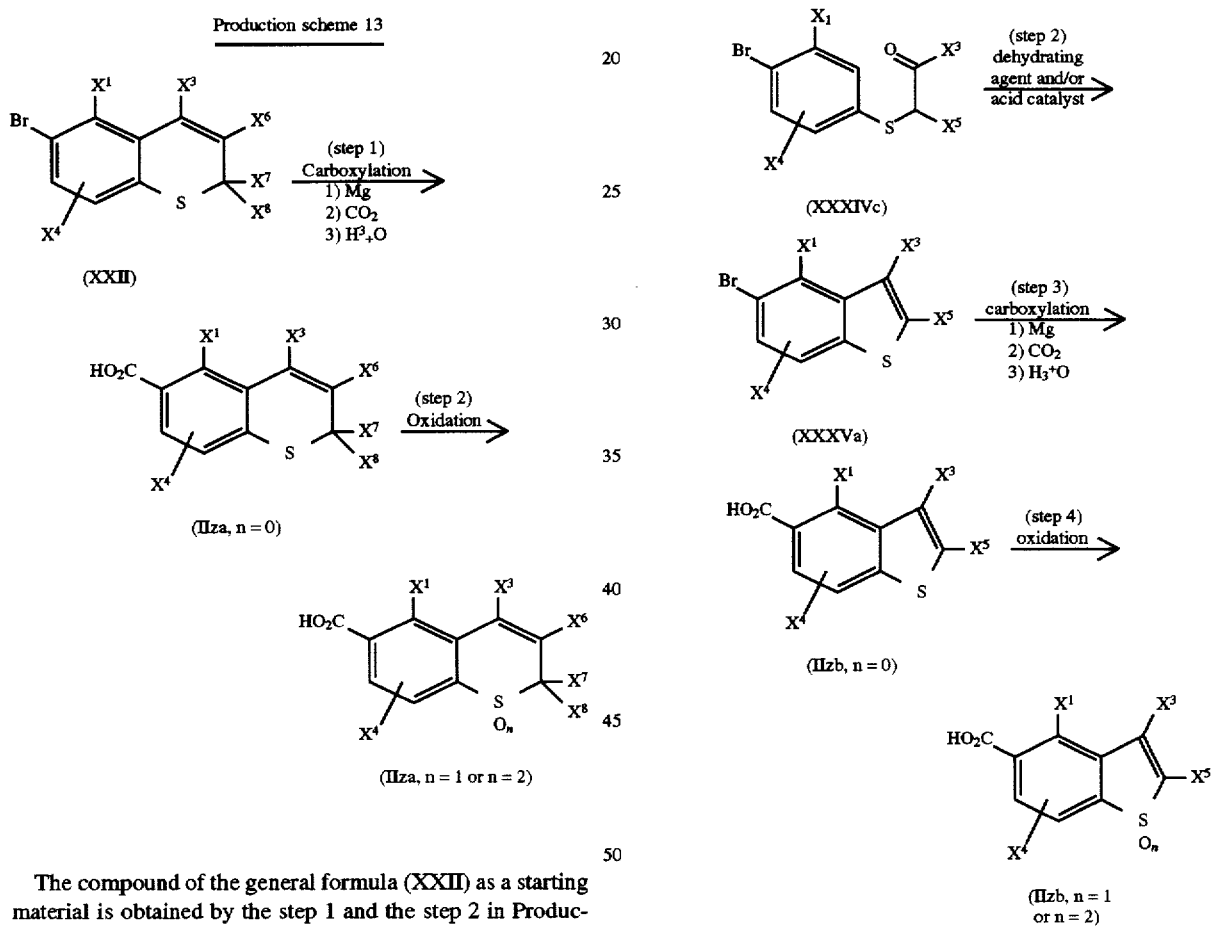

The compound of the general formula (XXII) as a starting material is obtained by the step 1 and the step 2 in Production scheme 4. The steps 1 and 2 thereafter are essentially the same as step 4 or 5 in Production scheme 1 and the detailed explanation thereof is omitted.

An aromatic carboxylic acid derivative of the formula (II) in which p is 0 and $X^2$ and $X^5$ together form a bond, i.e., a compound of the formula (IIzb), is produced by the following Production scheme 14.

As a starting material, a bromine-substituted thiophenol derivative of the formula (VI-Br) is used in place of the substituted thiophenol of the formula (VI) in Production scheme 9. The bromine-substituted thiophenol derivative is also obtained by a known method similar to the method of producing the substituted thiophenol.

The subsequent steps 1 and 2 are essentially the same as the steps 1 and 2 in Production scheme 9, and the steps 3 and 4 are the same as the step 4 or 5 in Production scheme 7. Their details are therefore omitted.

The novel pyrazole derivative of the formula (I) in which p is 1 and both $X^2$ and $X^5$ are hydrogen, provided by the present invention, i.e., a pyrazole derivative of the general formula (If) or (Ig), is also obtained by the following method.

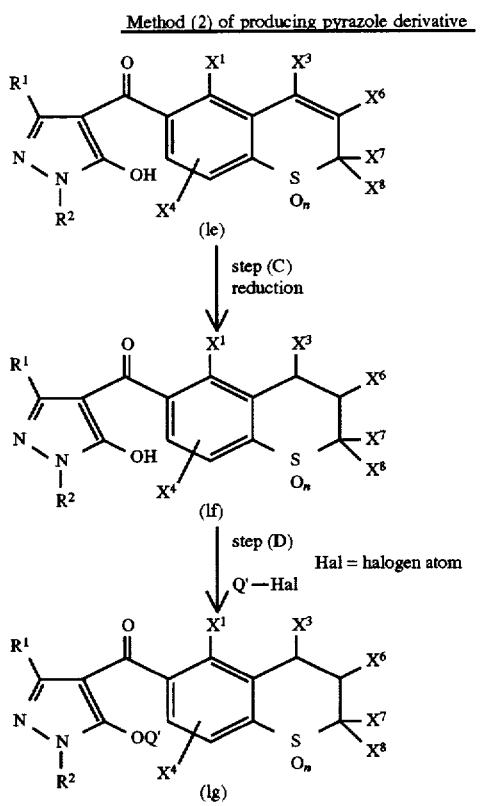

(Step 1)

This is a step in which a pyrazole derivative of the formula (Ie) is reduced to form a pyrazole derivative (If) of the present invention. The reduction is preferably carried out by a method using hydrogen having atmospheric pressure or elevated pressure in the presence of a catalyst such as palladium or platinum oxide. The amount of the catalyst is 5–20% by weight based on the pyrazole derivative of the formula (Ie). As a solvent, it is preferred to use an alcohol such as methanol or ethanol. The reaction temperature is from room temperature to about 80° C., while the reaction generally smoothly proceeds at room temperature. The reaction time is approximately 2 hours to 24 hours.

(Step 2)

The step 2 is a step in which a pyrazole derivative (Ig) is obtained by reacting the pyrazole derivative (If) with $Q^1$-Hal. This step 2 is basically the same as the step 2 in the method (1) of producing a pyrazole derivative, to which please refer for details.

The 5-hydroxypyrazole of the general formula (III) as a starting material for the production of the pyrazole derivative (I) of the present invention can be produced by one of the following methods depending upon its substituent. In the following reaction schemes, $R^1$ and $R^2$ are as defined in the general formula (I).

(1) Method disclosed in East Germany Patent 83145

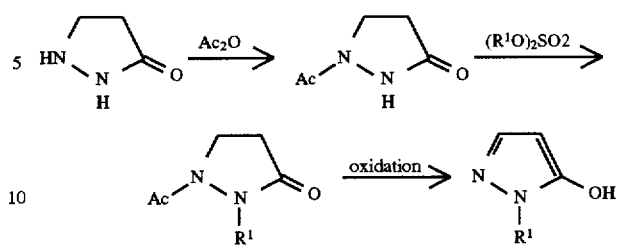

(2) Method disclosed in U. S. Patent 4,744,815

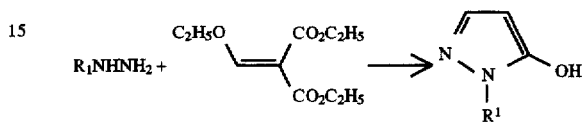

(3) Method disclosed in JP-A-3-44375

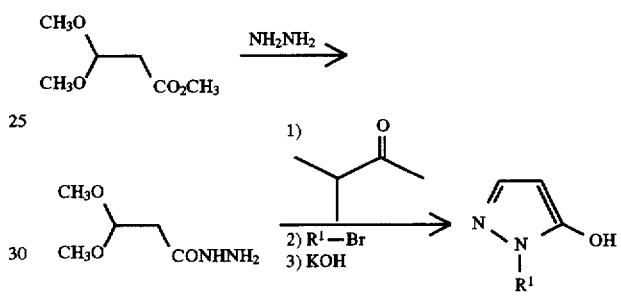

(4)

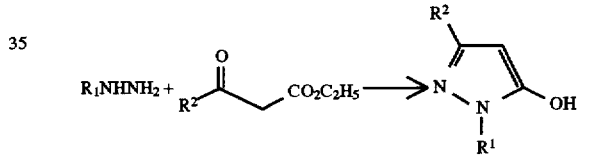

(5)

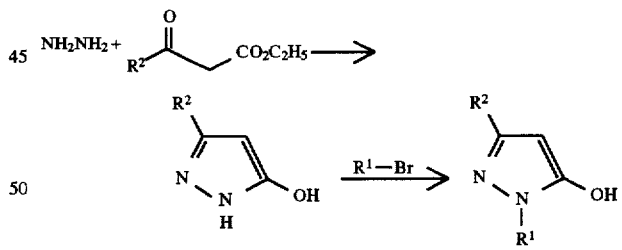

The above (1)–(3) show a method of producing 5-hydroxypyrazole of the general formula (III) in which $R^2$=hydrogen atom.

The above (4) and (5) show a method of producing 5-hydroxypyrazole of the general formula (III) in which $R^2=C_1-C_4$ alkyl group, $C_1-C_4$ haloalkyl group or $C_2-C_4$ alkoxyalkyl group.

EXAMPLES

The present invention will be explained further in detail with reference to Examples hereinafter, while the present invention shall not be limited to these Examples.

Intermediate Preparation Example 1

4,4,5,8-Tetramethylthiochroman-6-carboxylic acid-1,1-dioxide used in Preparation Example 1 to be described later was prepared in the following steps.

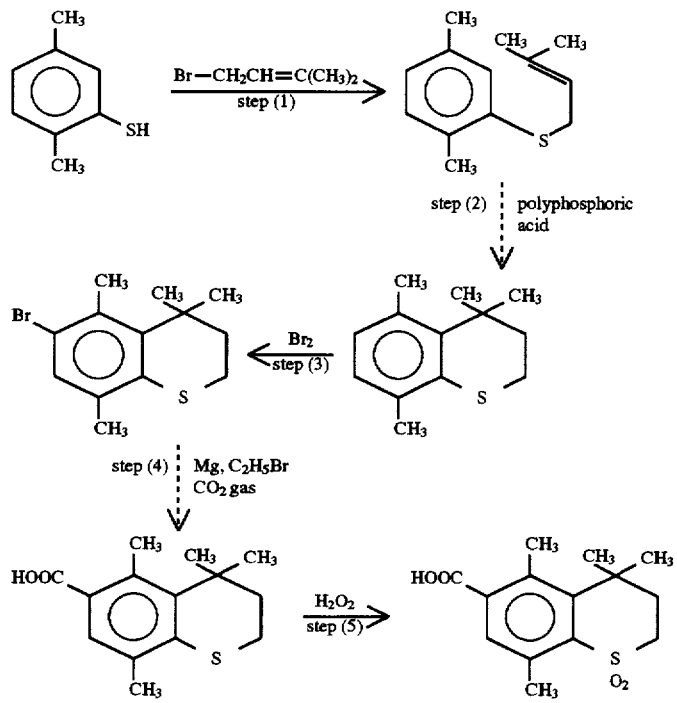

Step (1)

80 ml of acetone, 9.1 g (0.06 mol) of 1-bromo-3-methyl-2-butene and 8.0 g (0.058 mol) of anhydrous potassium carbonate were added to 8.0 g (0.058 mol) of 2,5-dimethylthiophenol, and the mixture was refluxed under heat for 1 hour. After the completion of the reaction, a formed salt was removed by filtration, and the acetone was distilled off under reduced pressure. Then, ethyl acetate was added to the residue, and the mixture was washed with a saturated sodium chloride aqueous solution. The mixture was dried over anhydrous sodium sulfate, and then the ethyl acetate was distilled off to give 12 g (yield 100%) of 2-methyl-4-(2,5-dimethylphenyl)thio-2-butene.

N.M.R. (ppm, solvent: deuterochloroform, internal standard: tetramethylsilane): 1.60(3H,s), 1.70(3H,s), 2.30(6H,s), 3.50(2H,d), 5.15–5.50(H,m), 6.80–7.10(3H,m)

Step (2)

7.0 Grams (0.034 mol) of 2-methyl-4-(2,5-dimethylphenyl)thio-2-butene was added to 51 g of polyphosphoric acid with stirring. The mixture was further stirred at room temperature for 30 minutes, and the reaction mixture was poured into ice water and extracted with n-hexane. An organic layer was washed with a saturated sodium chloride aqueous solution and then dried over anhydrous sodium sulfate. The n-hexane was distilled off under reduced pressure to give 6.7 g (yield 95%) of 4,4,5,8-tetramethylthiochroman.

N.M.R. (ppm, solvent: deuterochloroform, internal standard: tetramethylsilane): 1.40(6H,s), 1.95–2.15(2 H,m), 2.20(3 H,s), 2.50(3 H,s), 2.80–3.10(2 H,m), 6.80(2 H,dd)

Step (3)

100 ml of methylene chloride was added to 13.2 g (0.064 mol) of 4,4,5,8-tetramethylthiochroman, 10.2 g (0.064 mol) of bromine was dropwise added at room temperature, and then the mixture was allowed to react for 2 hours. After the completion of the reaction, 70 ml of a 2% sodium hydrogensulfite aqueous solution was added, excessive bromine was removed, and the reaction mixture was liquid-separated.

An organic layer was washed with a saturated sodium hydrogencarbonate aqueous solution and with a saturated sodium chloride aqueous solution, and dried over anhydrous sodium sulfate. The methylene chloride was distilled off under reduced pressure, and the resultant oily substance was purified by silica gel column chromatography to give 15.9 g (yield 87%) of 4,4,5,8-tetramethyl-6-bromothiochroman.

N.M.R. (ppm, solvent: deuterochloroform, internal standard: tetramethylsilane): 1.45(6 H,s), 1.90–2.10(2 H,m), 2.20(3H,s), 2.50(3H,s), 2.80–3.00(2H,m), 7.20(H,s)

Step (4)

2.9 Grams (0.12 mol) of magnesium was dispersed in 100 ml of THF (tetrahydrofuran), and 7.4 g (0.068 mol) of ethyl bromide was dropwise added. The mixture was allowed to react for 10 minutes, and then a solution of 9.7 g (0.034 mol) of 4,4,5,8-tetramethyl-6-bromothiochroman in THF was gradually added at room temperature. The reaction mixture was refluxed for 3 hours, and then cooled to 10° C., and carbon dioxide gas was bubbled for 1 hour. Unreacted magnesium was dissolved by adding 100 ml of 5% hydrochloric acid to the reaction mixture. THF was distilled off under reduced pressure, methylene chloride was added, and an aqueous layer was removed. An organic layer was extracted with a 5% potassium carbonate aqueous solution and adjusted to a pH of 1 by adding 5% hydrochloric acid. A formed solid was recovered by filtration, to give 7.4 g (yield 88%) of 4,4,5,8-tetramethylthiochroman-6-carboxylic acid.

N.M.R. (ppm, solvent: deuterochloroform, internal standard: tetramethylsilane): 1.50(6 H,s), 1.90–2.10(2 H,m), 2.25(3 H,s), 2.70(3 H,s), 2.90–3.10(2 H,m), 7.55(H,s)

I.R. (KBr tablet, cm$^{-1}$):3,450–2,550, 2,980, 2,930, 1,695
m.p.: 166.0°–167.1° C.

Step (5)

4 ml of acetic acid was added to 5 g (0.02 mol) of 4,4,5,8-tetramethylthiochroman-6-carboxylic acid, further, 6.9 g (0.06 mol) of a 30% hydrogen peroxide aqueous solution was added, and the mixture was heated at 80° C. for 2 hours. 50 ml of a 2% sodium hydrogensulfite aqueous solution was added to the reaction mixture, and a precipitated solid was recovered by filtration to give 5.1 g (yield 90%) of 4,4,5,8-tetramethylthiochroman-6-carboxylic acid-1,1-dioxide.

N.M.R. (ppm, solvent: deuterochloroform, internal standard: tetramethylsilane): 1.60(6 H,s), 2.25–2.50(2 H,m), 2.65(3 H,s), 2.75(3 H,s), 3.30–3.50(2 H,m), 7.55(H,s)

I.R. (KBr tablet, cm$^{-1}$): 3500-2,550, 3,000, 2,950, 1,630, 1,290, 1,130 m.p.: 208.8°–209.3° C.

Intermediate Preparation Example 2

4,4,5-Trimethylthiochroman-6-carboxylic acid-1,1-dioxide used in Preparation Example 2 to be described later was prepared in the following steps.

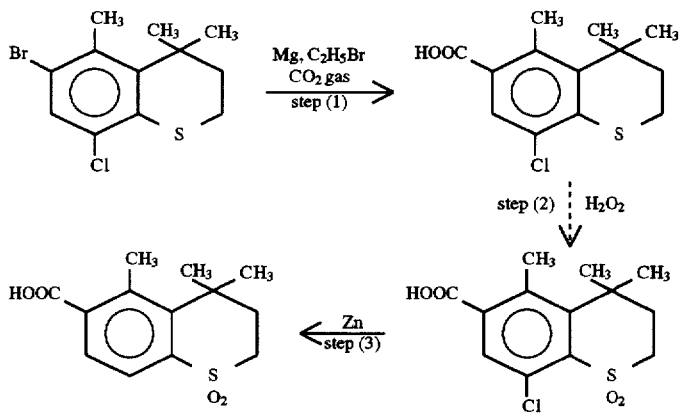

Step (1)

0.63 Gram (0.026 mol) of magnesium was dispersed in 30 ml of THF, and 1.89 g (0.0173 mol) of ethyl bromide was dropwise added. The mixture was allowed to react for 10 minutes, and then a solution of 1.76 g (0.0058 mol) of 4,4,5-trimethyl-6-bromo-8-chlorothiochroman in THF was gradually added at room temperature. The reaction mixture was refluxed for 7 hours, and then cooled to 10° C., and carbon dioxide gas was bubbled for 1 hour. Unreacted magnesium was dissolved by adding 30 ml of 5% hydrochloric acid to the reaction mixture. THF was distilled off under reduced pressure, ethyl acetate was added, and an aqueous layer was removed. An organic layer was extracted with a saturated sodium bicarbonate aqueous solution and adjusted to a pH of 1 by adding 5% hydrochloric acid, and a formed solid was recovered by filtration, to give 0.54 g (yield 40%) of 4,4,5-trimethyl-8-chlorothiochroman-6-carboxylic acid.

N.M.R. (ppm, solvent: deutero chloroform, internal standard: tetramethylsilane): 1.50(6 H,s), 1.90–2.10(2 H,m), 2.60(3 H,s), 2.85–3.10(2 H,m), 7.55(H,s)

I.R. (KBr tablet, cm$^{-1}$) :3,450-2,550, 2,980, 2,930, 1,695

Step (2)

10 ml of acetic acid was added to 0.82 g (3.0 mmol) of 4,4,5-trimethyl-8-chlorothiochroman-6-carboxylic acid, 0.82 g (7.5 mmol) of a 30% hydrogen peroxide aqueous solution was further added, and the mixture was heated at 80° C. for 3 hours. The reaction mixture was poured into 100 ml of ice water, and was extracted with ethyl acetate. An organic layer was washed with a saturated sodium chloride aqueous solution and dried over anhydrous sodium sulfate. The ethyl acetate was distilled off under reduced pressure to give 0.88 g (yield 96%) of 4,4,5-trimethyl-8-chlorothiochroman-6-carboxylic acid-1,1-dioxide.

N.M.R. (ppm, solvent: deuterochloroform, internal standard: tetramethylsilane): 1.60(6 H,s), 2.25–2.50(2 H,m), 2.65(3 H,s), 3.30–3.50(2 H,m), 7.60(H,s)

I.R. (KBr tablet, cm$^{-1}$): 3,500-2,550, 3,000, 2,950, 1,630, 1,290, 1,130

Step (3)

0.88 Gram (2.90 mmol) of 4,4,5-trimethyl-8-chlorothiochroman-6-carboxylic acid-1,1-dioxide was dissolved in ethanol having a water content of 60%, 0.55 g (8.70 mmol) of a zinc powder was added, and the mixture was refluxed under heat for 5 hours. After the completion of the reaction, 50 ml of water was added, the zinc powder was removed by filtration, and the remainder was extracted with ethyl acetate. The extract was washed with a saturated sodium chloride aqueous solution and dried over anhydrous sodium sulfate. The ethyl acetate was distilled off under reduced pressure to give 0.60 g (yield 78%) of 4,4,5-trimethylthiochroman-6-carboxylic acid-1,1-dioxide.

N.M.R. (ppm, solvent: deuterochloroform, internal standard: tetramethylsilane): 1.60(6 H,s), 2.30–2.50(2 H,m), 2.75(3 H,s), 3.30–3.50(2 H,m), 7.90(2 H,dd)

Intermediate Preparation Example 3

5,8-Dichloro-4,4-dimethylthiochroman-6-carboxylic acid-1,1-dioxide used in Preparation Example 3 to be described later was prepared in the following steps.

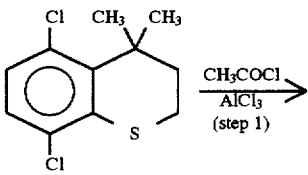

-continued

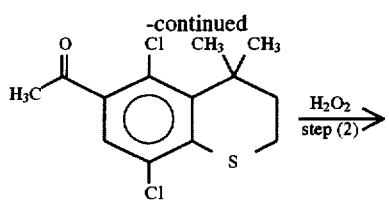

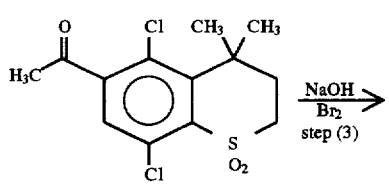

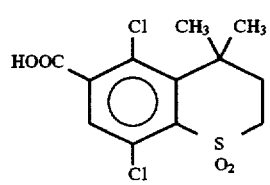

Step (1)

1.26 Grams (9.45 mmol) of anhydrous aluminum chloride was suspended in 10 ml of methylene chloride, and a solution of 0.74 g (9.45 mmol) of acetyl chloride in 5 ml of methylene chloride was dropwise added with cooling with ice. The mixture was stirred until the reaction mixture was homogeneous, then, a solution of 1.95 g (7.88 mmol) of 5,8-dichloro-4,4-dimethylthiochroman in 5 ml of methylene chloride was added, and the mixture was allowed to react at room temperature for 1 hour. After the completion of the reaction, the reaction mixture was poured into ice water and extracted with methylene chloride. An organic layer was washed with a saturated sodium chloride aqueous solution and dried over anhydrous sodium sulfate. The methylene chloride was distilled off under reduced pressure, and the resultant oily substance was purified by silica gel column chromatography to give 1.27 g (yield 56%) of 6-acetyl-5,8-dichloro-4,4-dimethylthiochroman.

N.M.R. (ppm, solvent: deuterochloroform, internal standard: tetramethylsilane): 1.60(6 H,s), 1.95–2.30(2 H,m), 2.55(3 H,s), 2.80–3.10(2 H,m), 7.15(H,s)

Step (2)

1 ml of acetic acid was added to 1.22 g (4.22 mmol) of 6-acetyl-5,8-dichloro-4,4-dimethylthiochroman, 1.43 g (12.66 mmol) of a 30% hydrogen peroxide aqueous solution was further added, and the mixture was heated at 80° C. for 2 hours. To the reaction mixture was added 10 ml of a 2% sodium hydrogensulfite, and a precipitated solid was recovered by filtration to give 0.96 g (yield 71%) of 6-acetyl-5,8-dichloro-4,4-dimethylthiochroman-1,1-dioxide.

N.M.R. (ppm, solvent: deuterochloroform, internal standard: tetramethylsilane): 1.65(6 H,s), 2.30–2.50(2 H,m), 2.55(3 H,s), 3.35–3.55(2 H,m), 7.30(H,s)

I.R. (KBr tablet, cm$^{-1}$): 3,200–2,700, 1,700, 1,300, 1,130 m.p.: 154.3°–155.1° C.

Step (3)

1.04 Grams (26.1 mmol) of sodium hydroxide was dissolved in 20 ml of water, and 0.5 ml (8.7 mol) of bromine was added. Further, 0.93 g (2.9 mmol) of 6-acetyl-5,8-dichloro-4,4-dimethylthiochroman-1,1-dioxide was added, and the mixture was stirred for 3 hours. Then the mixture was heated at 100° C. for 5 hours. After the completion of the reaction, ethyl acetate was added, the mixture was liquid-separated, and hydrochloric acid was added to an aqueous layer to adjust the aqueous layer to a pH of 1. The extraction of the aqueous layer was carried out by adding ethyl acetate, and an organic layer was dried over anhydrous sodium sulfate. The ethyl acetate was distilled off under reduced pressure to give 0.84 g (yield 90%) of 5,8-dichloro-4,4-dimethylthiochroman-6-carboxylic acid-1,1-dioxide.

N.M.R. (ppm, solvent: deuteroacetone, internal standard: tetramethylsilane): 1.70(6 H,s), 2.30–2.50(2 H,m), 3.40–3.60(2 H,m), 7.75(H,s)

I.R. (KBr tablet, cm–1): 3,500-2,500, 1,750, 1,300, 1,130

Intermediate Preparation Example 4

5-Chloro-4,4,8-trimethyl-thiochroman-6-carboxylic acid-1,1-dioxide used in Preparation Example 29 to be described later was prepared in the following steps.

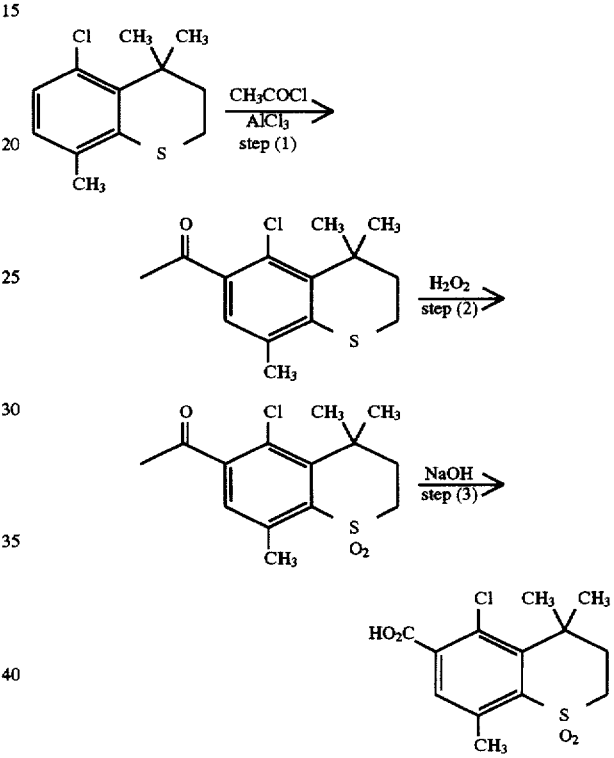

Step (1)

3.2 Grams (24 mmol) of anhydrous aluminum chloride was suspended in 20 ml of methylene chloride, and a solution of 1.9 g (24 mmol) of acetyl chloride in 10 ml of methylene chloride was dropwise added with cooling with ice. The mixture was stirred until the reaction mixture was homogeneous, and a solution of 4.5 g (20 mmol) of 5-chloro-4,4,8-trimethylthiochroman in 10 ml of methylene chloride was added. The mixture was allowed to react at room temperature for 1 hour. After the completion of the reaction, the reaction mixture was poured into ice water and extracted with methylene chloride. An organic layer was washed with a saturated sodium chloride aqueous solution and dried over anhydrous sodium sulfate. The methylene chloride was distilled off under reduced pressure, and the resultant oily substance was purified by silica gel column chromatography to give 3.0 g (yield 56%) of 6-acetyl-5-chloro-4,4,8-trimethylthiochroman.

Step (2)

5 ml of acetic acid was added to 3.0 g (11 mmol) of 6-acetyl-5-chloro-4,4,8-trimethylthiochroman, 3.7 g (33 mmol) of a 30% hydrogen peroxide aqueous solution was further added, and the mixture was heated at 80° C. for 2 hours. 20 ml of a 2% sodium hydrogensulfite was added to the reaction mixture, and a precipitated solid was recovered by filtration to give 2.8 g (yield 85%) of 6-acetyl-5-chloro-4,4,8-trimethylthiochroman-1,1-dioxide.

N.M.R. (ppm, solvent: deuterochloroform, internal standard: tetramethylsilane): 1.67(6 H,s), 2.30–2.50(2 H,m), 2.56(3 H,s), 2.76(3 H,s), 3.30–3.50(2 H,m), 7.05(H,s)

Step (3)

3.6 Grams (85 mmol) of sodium hydroxide was dissolved in 70 ml of water, and 1.5 ml (29 mmol) of bromine was added with cooling with ice. Further, 2.8 g (9.3 mmol) of 6-acetyl-5-chloro-4,4,8-trimethylthiochroman-1,1-dioxide was added, and the mixture was stirred for 3 hours and then heated at 100° C. for 5 hours. After the completion of the reaction, ethyl acetate was added, and the mixture was liquid-separated. An aqueous layer was adjusted to a pH of 1 by adding hydrochloric acid. The extraction of the aqueous layer was carried out by adding ethyl acetate, and an organic layer was dried over anhydrous sodium sulfate. The ethyl acetate was distilled off under reduced pressure to give 2.1 g (yield 75%) of 5-chloro-4,4,8-trimethylthiochroman-6-carboxylic acid-1,1-dioxide.

N.M.R. (ppm, solvent: deuteroacetone, internal standard: tetramethylsilane): 1.70(6 H,s), 2.30–2.50(2 H,m), 2.75(3 H,s), 3.40–3.60(2 H,m), 7.50(H,s)

Intermediate Preparation Example 5

3,3,4,7-Tetramethyl-2-hydrobenzo[b]thiophene-5-carboxylic acid-1,1-dioxide used as a starting material in Preparation Example 43 to be described later was prepared in the following steps.

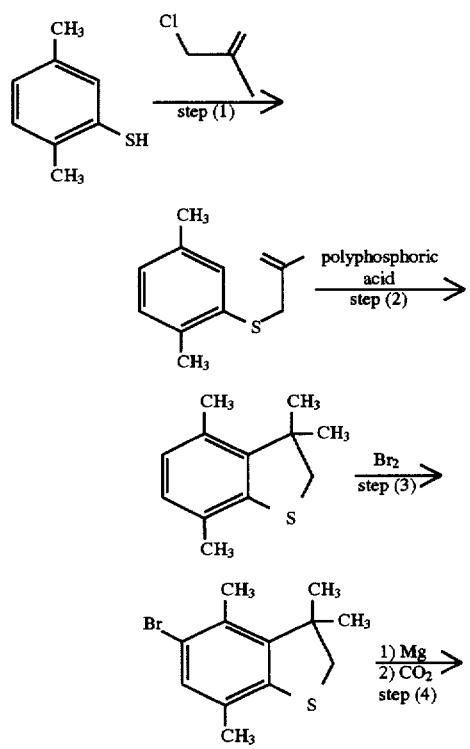

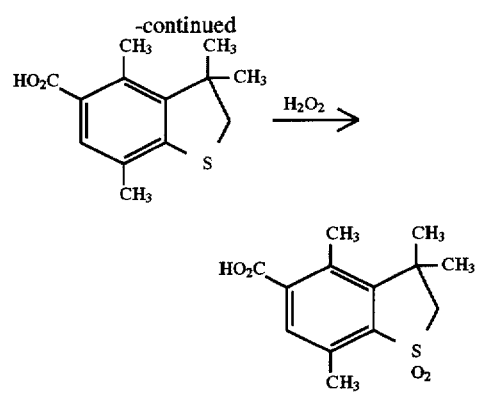

Step (1)

A 100-ml eggplant type flask was charged with 6.9 g (50 mmol) of 2,5-dimethylthiophenol, 5.5 g (60 mmol, 1.2 equivalents) of methallyl chloride which was a halogenated olefin, 6.9 g (50 mmol, 1 equivalent) of potassium carbonate and 30 ml of acetone, and the mixture was refluxed under heat for 1 hour. The reaction mixture was allowed to cool, insolubles were removed by filtration, and the acetone was distilled off. The resultant residue was re-dispersed in n-hexane and washed with a saturated sodium chloride aqueous solution. An organic layer was dried over anhydrous sodium sulfate, and then the solvent was distilled off to give 8.6 g (yield 89%) of 2-methyl-3-(2,5-dimethylphenylthio)-propane.

N.M.R. (ppm, solvent: deutero chloroform, internal standard: tetramethylsilane): 1.87(3 H,s), 2.28(3 H,s), 2.33(3 H,s), 3.49(2 H,s), 4.87(2 H,m), 6.8–7.3(3 H,m)

I.R. (KBr tablet, cm$^{-1}$): 3090, 2980, 1610

Step (2)

A 100-ml eggplant type flask was charged with 8.6 g (45 mmol) of the 2-methyl-3-(2,5-dimethylphenylthio)-1-propane obtained in the above step (1) and 50 g of polyphosphoric acid (containing 300 mmol (6.7 equivalents) of diphosphorus pentoxide ($P_2O_5$)) as a dehydration-condensation agent, and the mixture was allowed to react at 150° C. for 2 hours. After the completion of the reaction, the reaction mixture was poured into ice water and extracted with n-hexane. The resultant organic layer was washed with a saturated sodium chloride aqueous solution and dried over anhydrous sodium sulfate. The solvent was distilled off to give a crude product, and the crude product was purified by column chromatography (elution solvent: n-hexane) to give 1.6 g (yield 19%) of 3,3,4,7-tetramethyl-2-hydrobenzo[b]thiophene.

N.M.R. (ppm, solvent: deutero chloroform, internal standard: tetramethylsilane): 1.45(6 H,s), 2.21(3 H,s), 2.36(3 H,s), 3.08(2 H,s), 6.80(2 H,dd)

I.R. (KBr tablet, cm$^{-1}$): 2970, 1465, 800

Step (3)

A 100-ml eggplant type flask was charged with 1.6 g (8 mmol) of the 3,3,4,7-tetramethyl-2-hydrobenzo[b]thiophene obtained in the above step (2) and 30 ml of chloroform, and 0.55 ml (10.7 mmol, 1.34 equivalents) of bromine was dropwise added. The mixture was allowed to react at room temperature for 1 hour, and the reaction mixture was consecutively washed with a sodium hydrogensulfite and with a saturated sodium chloride aqueous solution and dried over anhydrous sodium sulfate. The solvent was distilled off to give 1.9 g (yield 85%) of 5-bromo-3,3,4,7-tetramethyl-2-hydrobenzo[b]thiophene.

N.M.R. (ppm, solvent: deutero chloroform, internal standard: tetramethylsilane): 1.48(6 H,s), 2.18(3 H,s), 2.41(3 H,s), 3.08(2 H,s), 7.20(H,s)

I.R. (KBr tablet, cm$^{-1}$): 2950, 1440, 1100

Step (4)

A 100-ml three-necked flask was charged with 30 ml of THF and 0.7 g (24 mmol, 3.4 equivalents) of magnesium, and 1.52 g (14 mmol, 2 equivalents) of ethyl bromide was dropwise added to activate the mixture. Then, a solution of 1.9 g (7.0 mmol) of the 5-bromo-3,3,4,7-tetramethyl-2-hydrobenzo[b]thiophene obtained in the above step (3) in 5 ml of THF was dropwise added, and the mixture was refluxed under heat for 4 hours. The reaction mixture was allowed to cool to room temperature, and carbon dioxide gas was bubbled for 2 hours. The reaction was terminated by adding 5% hydrochloric acid to the reaction mixture, and the reaction mixture was extracted with ethyl acetate. The resultant organic layer was extracted with a potassium carbonate aqueous solution, and the resultant aqueous layer was washed with ethyl acetate, then neutralized with 5% hydrochloric acid and extracted with ethyl acetate. The resultant organic layer was washed with a saturated sodium chloride aqueous solution and then dried over anhydrous sodium sulfate, and the solvent was distilled off to give 1.2 g (yield 70%) of 3,3,4,7-tetramethyl-2-hydrobenzo[b]thiophene-5-carboxylic acid.

N.M.R. (ppm, solvent: deutero chloroform, internal standard: tetramethylsilane): 1.51(6 H,s), 2.22(3 H,s), 2.58(3 H,s), 3.12(2 H,s), 7.62(H,s)

I.R. (KBr tablet, cm$^{-1}$): 3500, 3000, 1690

Step (5)

A 100-ml eggplant type flask was charged with 1.2 g (4.9 mmol) of the 3,3,4,7-tetramethyl-2-hydrobenzo[b]thiophene-5-carboxylic acid, 1.7 ml (15.0 mmol, 3.1 equivalents) of 30% H$_2$O$_2$ and 10 ml of acetic acid, and the mixture was allowed to react at 100° C. for 2 hours. The reaction mixture was poured into a sodium hydrogensulfite and extracted with ethyl acetate. The resultant organic layer was washed with a saturated sodium chloride aqueous solution and dried over anhydrous sodium sulfate, and the solvent was distilled off to give 1.0 g (yield 79%) of 3,3,4,7-tetramethyl-2-hydrobenzo[b]thiophene-5-carboxylic acid-1,1-dioxide.

N.M.R. (ppm, solvent: deutero chloroform, internal standard: tetramethylsilane): 1.69(6 H,s), 2.63(6 H,s), 3.38(2 H,s), 7.30(H,s), 7.72(H,s)

I.R. (KBr tablet, cm$^{-1}$): 3450, 1740

Intermediate Preparation Example 6

4,5,8-Trimethylthiochroman-6-carboxylic acid-1,1-dioxide used as a starting material in Preparation Example 44 to be described later was prepared in the following steps.

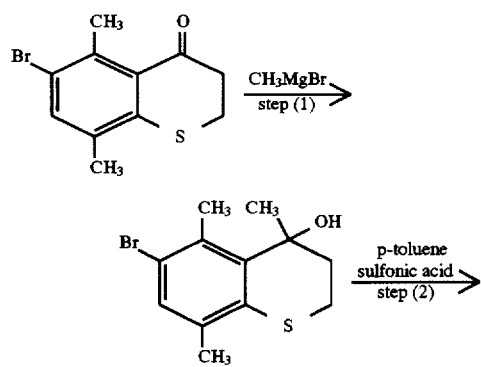

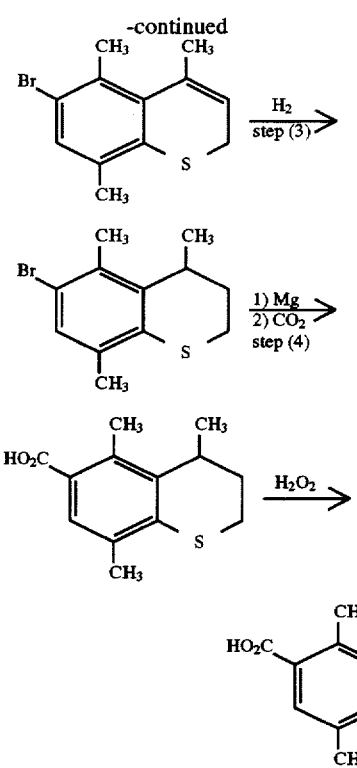

Step (1)

A 300-ml three-necked flask was charged with 55 ml (55 mmol, 3 equivalents) of a 1M solution of magnesium methyl bromide (MeMgBr) and 100 ml of tetrahydrofuran (THF), and the mixture was cooled with ice under nitrogen current. To this mixture was dropwise added a solution of 5.0 g (18.4 mmol) of 6-bromo-5,8-dimethylthiochroman-4-one in 15 ml of THF, and the mixture was stirred at room temperature for 3 hours and then refluxed for 2 hours. To the reaction mixture was added 5% HCl, and the mixture was extracted with ethyl acetate. The resultant organic layer was washed with a saturated sodium chloride aqueous solution and dried over anhydrous sodium sulfate, and the solvent was distilled off to give 5.2 g (yield 99%) of 6-bromo-4,5,8-trimethylthiochroman-4-ol.

N.M.R. (ppm, solvent: deutero chloroform, internal standard: tetramethylsilane): 1.60(3 H,s), 2.20(3 H,s), 2.26–2.36(2 H,m), 2.70(3 H,s), 2.80–3.10(2 H,m), 7.40(H,s)

Step (2)

A 200-ml flask equipped with a Dean Stark tube was charged with 5.4 g (18.8 mmol) of the 6-bromo-4,5,8-trimethylthiochroman-4-ol obtained in the above step (1), 100 ml of benzene and 10 mg (0.06 mmol, 0.0032 equivalent) of p-toluenesulfonic acid, and the mixture was refluxed under heat for 1 hour. After cooled, the reaction mixture was consecutively washed with a sodium hydrogencarbonate aqueous solution and with a saturated sodium chloride aqueous solution and dried over anhydrous sodium sulfate. The solvent was distilled off, and the resultant residue (crude product) was purified by silica gel column chromatography (developer solvent: hexane, ethyl acetate) to give 1.4 g (yield 27%) of 6-bromo-4,5,8-trimethyl-3,4-dehydrothiochroman.

N.M.R. (ppm, solvent: deutero chloroform, internal standard: tetramethylsilane): 2.29(3 H,s), 2.42(3 H,s), 2.99(2 H,dd), 6.02(H,t), 7.22(H,s)

Step (3)

A 100-ml portable reactor was charged with 1.32 g of the 6-bromo-4,5,8-trimethyl-3,4-dehydrothiochroman, 0.55 g of 5% Pd/C and 20 ml of chloroform, and the mixture was allowed to react under a hydrogen pressure of 5 kg/cm² G at room temperature for 6 hours. After the completion of the reaction, the catalyst was separated by filtration, and the solvent was distilled off to give 1.21 g (yield 91%) of 6-bromo-4,5,8-trimethylthiochroman.

N.M.R. (ppm, solvent: deutero chloroform, internal standard: tetramethylsilane): 1.15(3 H,d), 2.20(3 H,s), 2.38(3 H,s), 1.8–2.3(H,m), 2.9–3.1(2 H,m), 3.2–3.4(2 H,m), 7.20 (H,s)

Step (4)

A 50-ml three-necked flask was charged with 15 ml of THF and 0.43 g (18 mmol) of magnesium, and 0.97 g (9 mmol) of ethyl bromide was dropwise added to activate the mixture. Then, a solution of 1.21 g (4.5 mmol) of the 6-bromo-4,5,8-trimethylthiochroman in 3 ml of THF was dropwise added, and the mixture was refluxed under heat for 6 hours. The reaction mixture was allowed to cool to room temperature, and $CO_2$ gas was bubbled. The reaction was terminated by adding 5% hydrochloric acid, and the reaction mixture was extracted with ethyl acetate. An organic layer was extracted with a potassium carbonate aqueous solution, and an aqueous layer was washed with ethyl acetate and neutralized with 5% hydrochloric acid. The so-formed carboxylic acid was extracted with ethyl acetate, washed with a saturated sodium chloride aqueous solution and then dried over sodium sulfate. The solvent was distilled off to give 0.75 g (yield 71%) of 4,5,8-trimethylthiochroman-6-carboxylic acid.

N.M.R. (ppm, solvent: deutero chloroform, internal standard: tetramethylsilane): 1.14(3 H,d), 2.23(3 H,s), 1.75–2.35(2 H,m), 2.55(3 H,s), 2.9–3.1(2 H,m), 3.2–3.5 (2 H,m), 7.60(H,s)

Step (5)

A 30-ml eggplant type flask was charged with 0.75 g (3.2 mmol) of the 4,5,8-trimethylthiochroman-6-carboxylic acid, 1.1 g (9.5 mmol) of 30% hydrogen peroxide and 1 ml of acetic acid, and the mixture was allowed to react at 100° C. for 2 hours. The reaction mixture was poured into a sodium hydrogensulfite aqueous solution and extracted with ethyl acetate. The extract was washed with a saturated sodium chloride aqueous solution and dried over sodium sulfate, and the solvent was distilled off to give 0.76 g (yield 98%) of 4,5,8-trimethylthiochroman-6-carboxylic acid-1,1,dioxide.

N.M.R. (ppm, solvent: deutero chloroform, internal standard: tetramethylsilane): 1.35(3 H,d), 2.0–2.4(H,m), 2.57(3 H,s), 2.77(3 H,s), 3.3–3.8 (4 H,m), 7.67(H,s)

Intermediate Preparation Example 7

4-Ethyl-5,8-dimethylthiochroman-6-carboxylic acid-1,1, dioxide used as a starting material in Preparation Example 45 to be described later was prepared in the following steps.

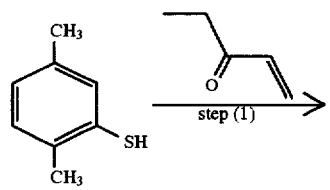

Step (1)

0.5 ml of triethylamine was added to a mixture containing 10.0 g (72.5 mmol) of 2,5-dimethylthiophenol, 7.32 g (87.0 mmol) of ethyl vinyl ketone and 30 ml of dichloroethane, and the mixture was stirred for 1 hour. The mixture was diluted with dichloromethane, washed with a saturated sodium hydrogencarbonate aqueous solution, dried over anhydrous sodium sulfate and filtered, and the solvent was removed under reduced pressure to give 16.1 g (yield 100%) of (2,5-dimethylphenyl)-3-oxopentylsulfide in the form of a colorless transparent oil.

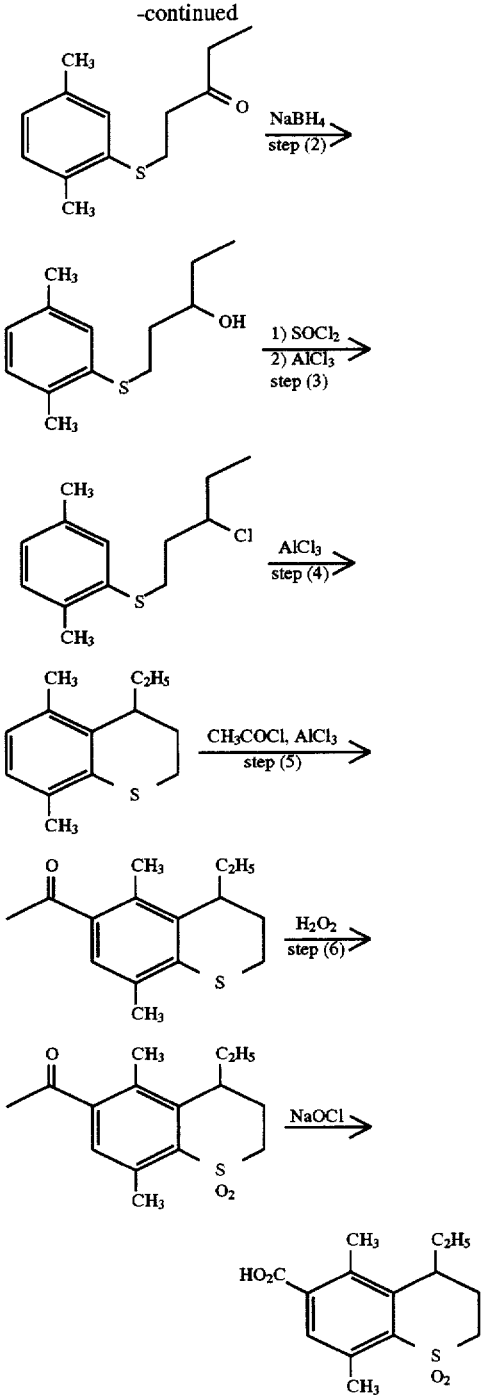

N.M.R. (ppm, solvent: deutero chloroform, internal standard: tetramethylsilane): 1.05(3 H,t,J=7 Hz), 2.31(6 H,s), 2.43(2 H,q,J=7 Hz), 2.6–2.9(2 H,m), 3.0–3.3 (2 H,m), 6.9–7.2(3H,m)

Step(2)

1.65 g (43.6 mmol) of sodium borohydride was gradually added to 16.1 g (72.6 mmol) of the (2,5-dimethylphenyl)-3-oxopentylsulfide and 64 ml of ethanol at 0° C., and the mixture was stirred at room temperature for 1 hour. The mixture was poured into ice and an aqueous solution containing 5% hydrochloric acid and extracted with dichloroethane. The extract was dried over anhydrous sodium sulfate and filtered, and the solvent was distilled off under reduced pressure to give 16.3 g of (2,5-dimethylphenyl)-3-hydroxypentylsulfide in the form of a colorless transparent oil.

N.M.R. (ppm, solvent: deutero chloroform, internal standard: tetramethylsilane): 0.59(3 H,t), 1.3–1.9(4 H,m), 2.31(6 H,s), 2.9–3.1(2 H,m), 3.6–3.9 (H,m), 6.8–7.2(3 H,m)

Step (3)

4.94 ml (67.8 mmol) of thionyl chloride was gradually dropwise added to a mixture containing 10.0 g (45.2 mmol) of the (2,5-dimethylphenyl)-3-hydroxypentylsulfide and 30 ml of dichloroethane, and the mixture was stirred at 60° C. for 2 hours. The reaction mixture was cooled to room temperature, and the solvent was distilled off under reduced pressure. Dichloromethane was added to the resultant residue, the mixture was washed with a saturated sodium hydrogencarbonate aqueous solution and dried over anhydrous sodium sulfate, and the solvent was distilled off under reduced pressure to give 10.9 g (yield 99%) of (2,5-dimethylphenyl)-3-chloropentylsulfide as a crude product. This compound was used for a subsequent reaction without purifying it any further.

N.M.R. (ppm, solvent: deutero chloroform, internal standard: tetramethylsilane): 1.03(3 H,t), 1.5–2.4 (4 H,m), 2.32(6 H,s), 2.8–3.2(2 H,m), 3.9–4.2 (H,m), 6.8–7.2(3 H,m)

Step (4)

A mixture of 9.40 g (38.7 mmol) of the (2,5-dimethylphenyl)-3-chloropentylsulfide with dichloromethane was gradually dropwise added to a suspension containing 5.18 g (38.7 mmol) of aluminum chloride and 20 ml of methylene chloride at 0° C., and the resultant mixture was stirred at 0° C. for 2 hours and further stirred at room temperature for 2 hours. The reaction mixture was poured into ice water and extracted with methylene chloride. The extract was dried over anhydrous sodium sulfate and filtered, and the solvent was distilled off under reduced pressure. The residue was purified by column chromatography (silica gel; hexane→hexane/ethyl acetate=20:1) to give 3.64 g (yield 47%) of 4-ethyl-5,8-dimethylthiochroman in the form of a brown oil.

N.M.R. (ppm, solvent: deutero chloroform, internal standard: tetramethylsilane): 0.9–1.1(3 H,m), 1.4–2.5 (10 H,m), 2.8–4.1(3 H,m), 6.8–7.2 (2 H,m)

Step (5)

A mixed solution containing 1.91 g (9.26 mmol) of the 4-ethyl-5,8-dimethylthiochroman and dichloromethane was dropwise added to a mixed solution containing 1.49 g (11.1 mmol) of aluminum chloride, 0.82 ml (11.6 mmol) of acetyl chloride and 6 ml of dichloromethane at 0° C. and the mixture was stirred for 1.5 hours. The reaction mixture was poured into ice and a solution containing 5% hydrochloric acid and extracted with dichloromethane. The extract was washed with a saturated sodium hydrogencarbonate, dried over anhydrous sodium sulfate and filtered, and the solvent was distilled off under reduced pressure to give 1.66 g (yield 72%) of 6-acetyl-4-ethyl-5,8-dimethylthiochroman.

N.M.R. (ppm, solvent: deutero chloroform, internal standard: tetramethylsilane): 0.99(3 H,t), 1.3–1.8(2 H,m), 2.21–2.6(2 H,m), 2.25(3 H,m), 2.38(3 H,s), 2.53(3 H,s), 2.8–3.8 (3 H,m), 7.21(H,s)

Step (6)

A mixed solution containing 1.66 g (6.68 mmol) of the 6-acetyl-4-ethyl-5,8-dimethylthiochroman, 2.28 g (20.1 mmol) of a 30% hydrogen peroxide aqueous solution and 2.0 ml of acetic acid was allowed to react at 80° C. for 2 hours. The reaction mixture was cooled to room temperature, a 2% sodium hydrogensulfite aqueous solution was added, and the mixture was extracted with ethyl acetate and washed with a saturated sodium hydrogencarbonate and then with a saturated sodium chloride aqueous solution. An organic layer was dried over anhydrous sodium sulfate and filtered, and then the solvent was distilled off under reduced pressure. The residue was purified by column chromatography (silica gel; hexane/ethyl acetate=2:1) to give 1.03 g (yield 55%) of 6-acetyl-4-ethyl-5,8-dimethylthiochroman-1,1-dioxide.

N.M.R. (ppm, solvent: deutero chloroform, internal standard: tetramethylsilane): 1.53(3 H,t,J=7 Hz), 1.42(2 H,m), 2.2–2.6 (2 H,m), 2.31(3 H,s), 2.53(3 H,s), 2.75(3 H,s), 2.9–3.8(3 H,s), 7.20(H,s)

Step (7)

13 ml of a sodium hypochlorite aqueous solution was dropwise added to a mixed solution containing 1.03 g (3.67 mmol) of the 6-acetyl-4-ethyl-5,8-dimethylthiochroman-1,1-dioxide and 4 ml of dioxane at 0° C., and the mixture was stirred at 0° C. for 1 hour. Further, the mixture was stirred at room temperature overnight. 5 ml of a 20% sodium sulfite aqueous solution was added to the mixture, and the mixture was washed with dichloromethane. An aqueous layer was acidified (pH 1) with concentrated hydrochloric acid, extracted with ethyl acetate, dried over anhydrous sodium sulfate and filtered, and the solvent was distilled off under reduced pressure to give 0.90 g (yield 87%) of 4-ethyl-5,8-dimethylthiochroman-1,1-dioxide-6-carboxylic acid.

N.M.R. (ppm, solvent: deutero acetone, internal standard: tetramethylsilane): 1.07(3 H,t), 1.5–1.8 (2 H,m), 2.3–2.7 (2 H,m), 2.49(3 H,s), 2.69(3 H,s), 3.0–3.9 (3 H,m), 7.55(H,s)

Intermediate Preparation Example 8

3,4,7-Trimethyl-2-hydrobenzo[b]thiophene-5-carboxylic acid-1,1-dioxide used as a starting material in Preparation Example 46 to be described later was prepared in the following steps.

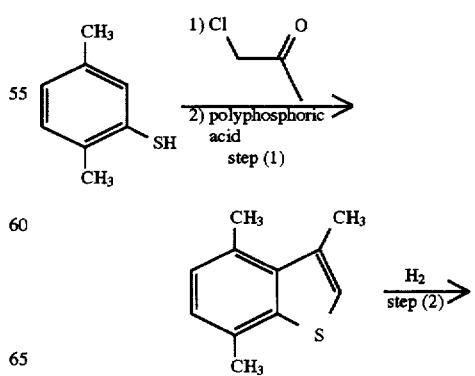

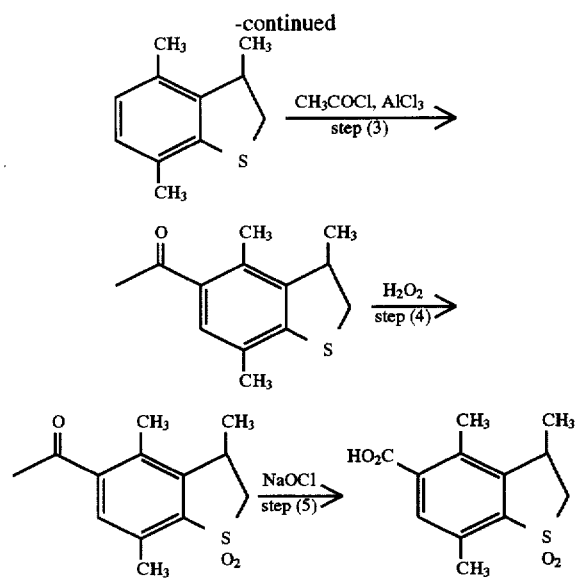

Step (1)

A 100-ml eggplant type flask was charged with 4.0 g (29 mmol) of 2,5-dimethylthiophenol as a substituted thiophenol, 3.2 g (35 mmol, 1.2 equivalents) of chloroacetone as an a-halo-carbonyl compound, 4.0 g (29 mmol, 1 equivalent) of anhydrous potassium carbonate and 30 ml of acetone, and the mixture was refluxed under heat for 2 hours. The reaction mixture was allowed to cool, then, insolubles were removed by filtration, and the acetone was distilled off. The resultant residue was re-dispersed in n-hexane and washed with a saturated sodium chloride aqueous solution. An organic layer was dried over anhydrous sodium sulfate, and then the solvent was distilled off. To the resultant residue was added 100 g of polyphosphoric acid as a dehydration-condensation agent, and the mixture was stirred at room temperature for 1 hour. The reaction mixture was poured into ice water, and a white crystal which precipitated was re-dispersed in n-hexane and washed with a saturated sodium chloride aqueous solution. The solvent was distilled off to give 4.5 g (yield 88%) of 3,4,7-trimethylthiophene.

N.M.R. (ppm, solvent: deutero chloroform, internal standard: tetramethylsilane): 2.48(3H,s), 2.62(3H,s), 2.72(3H,s), 2.98(3H,s)

Step (2)

A 50-ml eggplant type flask was charged with 1.0 g of the 3,4,7-trimethylbenzo[b]thiophene obtained in the above step (1), 30 ml of ethanol and 50 mg of platinum oxide, to carry out hydrogenation under atmospheric pressure. After the completion of the reaction, the ethanol was distilled off to give 0.94 g (yield 93%) of 3,4,7-trimethyl-2-hydrobenzo[b]thiophene.

N.M.R. (ppm, solvent: deutero chloroform, internal standard: tetramethylsilane): 1.24(3H,d), 2.21(3H,s), 2.26(3H, s), 2.7~3.1(H,m), 3.4–3.8(2H,m), 6.98(3H,s)

Step (3)

A 100-ml eggplant type flask was charged with 2.33 g (16.0 mmol, 1.2 equivalents) of aluminum chloride and 10 ml of dichloromethane, and the mixture was cooled with ice. To the mixture was dropwise added 1.15 ml (1.26 g, 17.5 mmol, 1.1 equivalents) of acetyl chloride, and the mixture was stirred under cooling with ice for 15 minutes. Then, a solution of 2.60 g (14.6 mmol) of 3,4,7-trimethyl-2-hydrobenzo[b]thiophene in 10 ml of dichloromethane was dropwise added.

The mixture was stirred with cooling with ice for 30 minutes, stirred at room temperature for 3 hours, and poured into ice water to terminate the reaction. An aqueous layer was extracted with dichloromethane, and an organic layer was washed with a saturated sodium chloride aqueous solution and then dried over anhydrous sodium sulfate. The solvent was distilled off to give 2.48 g (yield 77%) of 5-acetyl-3,4,7-trimethyl-2-hydrobenzo[b]thiophene.

N.M.R. (ppm, solvent: deutero chloroform, internal standard: tetramethylsilane): 1.24(3H,d), 2.25(3H,s), 2.43(3H, s), 2.54(3H,s), 2.95(H,d), 3.5~3.8(2H,m), 7.30(H,s)

Step (4)

A 30-ml eggplant type flask was charged with 2.48 g (11.3 mmol) of the 5-acetyl-3,4,7-trimethyl-2-hydrobenzo[b]thiophene, 3.8 ml of a 30% hydrogen peroxide aqueous solution and 3 ml of acetic acid, and the mixture was allowed to react at 100° C. for 2 hours. The reaction mixture was poured into a sodium sulfite aqueous solution and extracted with ethyl acetate. The extract was washed with a saturated sodium chloride aqueous solution and dried over sodium sulfate, and then the solvent was distilled off to give 2.67 g (yield 94%) of 5-acetyl-3,4,7-trimethyl-2-hydrobenzo[b]-thiophene-1,1-dioxide.

N.M.R. (ppm, solvent: deutero chloroform, internal standard: tetramethylsilane): 1.50(3H,d), 2.39(3H,s), 2.57(3H, s), 2.63(3H,s), 3.25(H,d), 3.5~3.75(2H,m), 7.35(H,s)

Step (5)

A 50-ml eggplant type flask was charged with 11.6 ml of 6.3 % hypochlorous acid and the content was cooled with ice. A solution of 2.67 g (10.6 mmol) of 5-acetyl-3,4,7-trimethyl-2-hydrobenzo[b]thiophene-1,1-dioxide in 10 ml of 1,4-dioxane was dropwise added. After the addition, the mixture was temperature-increased up to room temperature and then stirred for 3 hours. Then, a sodium sulfite aqueous solution was added, the reaction mixture was washed with methylene chloride twice, and then 10 ml of concentrated hydrochloric acid was added with cooling with ice. The mixture was extracted with ethyl acetate three times, and then dried over anhydrous sodium sulfate. The solvent was distilled off to give 2.38 g (yield 88 %) of 3,4,7-trimethyl-2-hydrobenzo[b]thiophene-5-carboxylic acid-1,1-dioxide.

N.M.R. (ppm, solvent: deutero chloroform, internal standard: tetramethylsilane): 1.50(3H,d), 2.58(3H,s), 2.65(3H, s), 3.28(H,d), 3.5~3.75(2H,m), 7.85(H,s)

Intermediate Preparation Example 9

5,8-Dimethyl-3,4-dehydrothiochroman-6-carboxylic acid used as a starting material in Preparation Example 47 to be described later was prepared in the following steps.

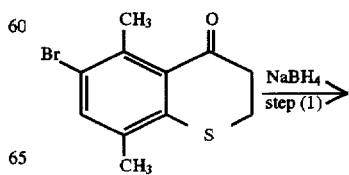

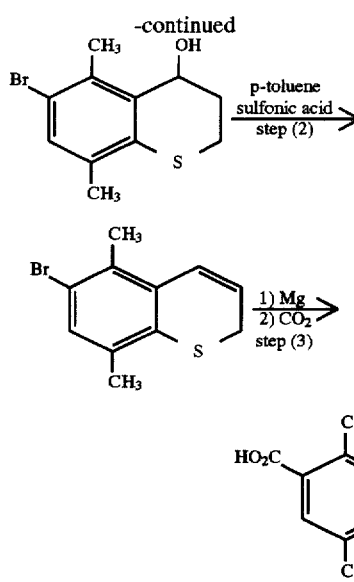

Step (1)

In a 100-ml eggplant type flask, 5.0 g (18.4 mmol) of 6-bromo-5,8-dimethylthiochroman-4-one as a halogenated thiochroman-4-one compound was dissolved in 30 ml of methanol, and 0.35 g (9.2 mmol, 0.5 equivalent) of sodium borohydride as a reducing agent was added at room temperature. The reaction mixture was stirred for 2 hours, then, diluted hydrochloric acid was added, and the mixture was extracted with ethyl acetate. An organic layer was washed with a saturated sodium chloride aqueous solution and dried over anhydrous sodium sulfate, and then solvent was distilled off to give 0.49 g (yield 95%) of 6-bromo-5,8-dimethylthiochroman-4-ol.

N.M.R. (ppm, solvent: deutero chloroform, internal standard: tetramethylsilane): 1.8~3.3(4H,m), 2.21(3H,s), 2.42 (3H,s), 5.06(H,t), 7.30(H,s)

Step (2)

A 200-ml flask equipped with a Dean Stark tube was charged with 4.0 g (16.6 mmol) of the 6-bromo-5,8-trimethylthiochroman-4-ol obtained in the above step (1), 100 ml of benzene and 10 mg (0.06 mmol, 0.0036 equivalent) of p-toluenesulfonic acid, and the mixture was refluxed under heat for 1 hour. After cooled, the reaction mixture was consecutively washed with a sodium hydrogencarbonate aqueous solution and with a saturated sodium chloride aqueous solution and dried over anhydrous sodium sulfate. The solvent was distilled off to give 2.6 g (yield 69%) of 6-bromo-5,8-dimethyl-3,4-dehydrothiochroman.

N.M.R. (ppm, solvent: deutero chloroform, internal standard: tetramethylsilane): 2.30(6H,s), 3.32(2H,dd), 5.9~6.2 (H,m), 6.6~7.0(2H,m)

Step (3)

A 200-ml three necked flask was charged with 50 ml of THF and 0.56 g (23 mmol, 1.2 equivalents) of magnesium, and the mixture was activated by adding 1 pieces of iodine and 5 drops of ethyl bromide. Then, a solution of 4.88 g (19 mmol) the 6-bromo-5,8-dimethyl-3,4-dehydrothiochroman obtained in the above step (2) in 5 ml of THF was dropwise added, and the mixture was refluxed under heat for 4 hours. The reaction mixture was allowed to cool to room temperature, and then carbon dioxide gas was bubbled for 2 hours. The reaction was terminated by dropwise adding 5% hydrochloric acid, and the reaction mixture was extracted with ethyl acetate. The resultant organic layer was extracted with a potassium carbonate aqueous solution, an aqueous layer was washed with ethyl acetate, neutralized by adding 5% hydrochloric acid and extracted with ethyl acetate. The resultant organic layer was washed with a saturated sodium chloride aqueous solution and dried over anhydrous sodium sulfate, and the solvent was distilled off to give 1.9 g (yield 46%) of 5,8-dimethyl-3,4-dehydrothiochroman-6-carboxylic acid.

N.M.R. (ppm, solvent: deutero chloroform, internal standard: tetramethylsilane): 2.32(3H,s), 2.60(3H,s), 3.33(2H, dd), 5.9~6.1(H,m), 6.81(H,d), 7.67(H,s) I.R. (KBr tablet, cm$^{-1}$): 3300~2600, 1680

Intermediate Preparation Example 10

5-Methyl-3,4-dehydrothiochroman-6-carboxylic acid-1, 1,dioxide used as a starting material in Preparation Example 48 to be described later was prepared in the following steps.

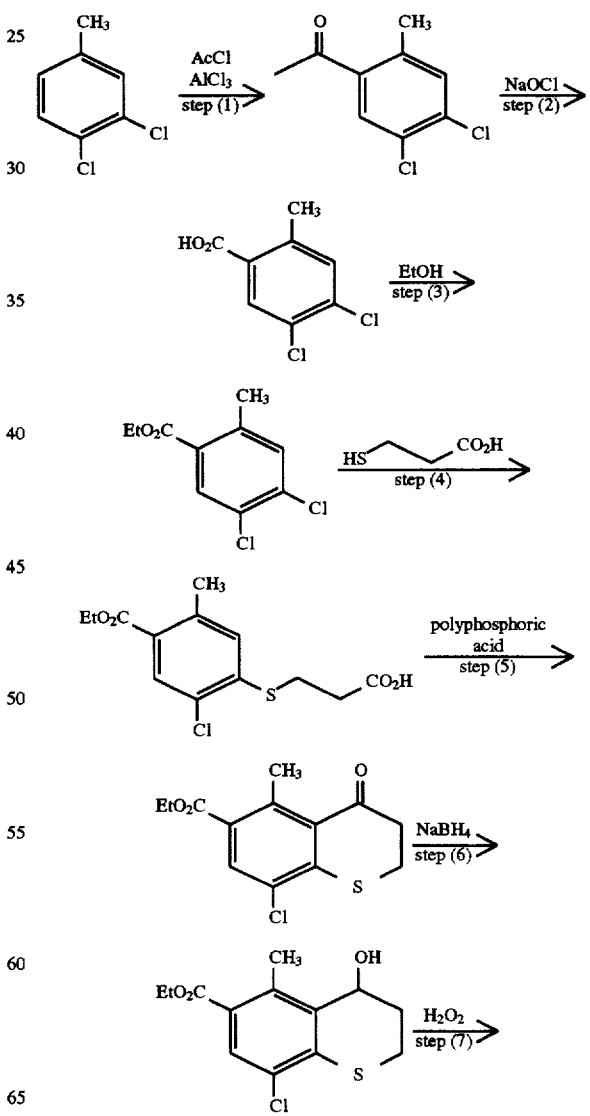

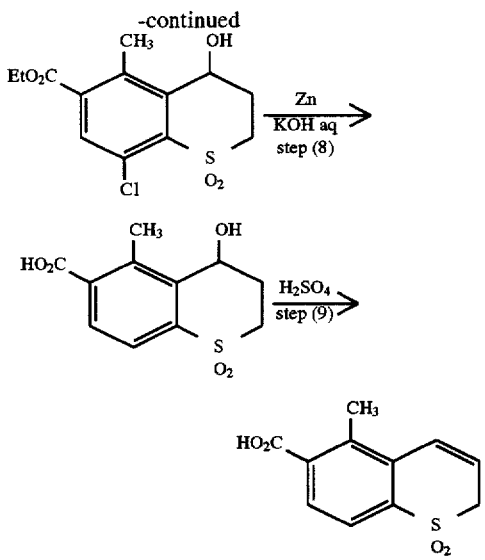

Step (1)

80 ml (100 g, 621 mmol) of 3,4-dichlorotoluene as a halogen-substituted benzene derivative was added to a solution of 100 g (750 mmol, 1.21 equivalents) of aluminum chloride as an acid catalyst in 250 ml of 1,2-dichloroethane, and then 55 ml (774 mmol, 1.25 equivalents) of acetyl chloride as an acetylating agent was dropwise added at room temperature. After the completion of the addition, the reaction mixture was stirred at room temperature for 10 minutes and then stirred at 70°~75° C. for 5 hours. After cooled, the reaction mixture was gradually added to 300 ml of ice water and separated to two layers. The resultant organic layer was concentrated. The resultant aqueous layer was extracted with ethyl acetate to obtain an organic layer, and the organic layer was added to the above-concentrated organic layer. The organic layer mixture was washed with 5% hydrochloric acid once, with a sodium carbonate aqueous solution twice and with a saturated sodium chloride aqueous solution once, and then dried over anhydrous sodium sulfate. The solvent was distilled off under reduced pressure to give 125.1 g (yield 86%) of 3,4-dichloro-6-methylacetophenone as a crude product.

N.M.R. (ppm, solvent: deutero acetone, internal standard: tetramethylsilane): 2.47(3H,s), 2.58(3H,s), 7.50(H,s), 7.97 (H,s)

Step (2)

1,350 ml (1.96 mol, 3 equivalents) of a 12.9% sodium hypochlorite as an oxidizing agent was diluted with 400 ml of water, and cooled to 8° C. with cooling with ice. To this mixture was dropwise added a solution of 132.3 g (652 mmol) of the 3,4-dichloro-6-methylacetophenone obtained in the above step (1) in 130 ml of dioxane at 10° C. or lower, and further, 130 ml of dioxane was added. Then, the ice bath was removed, and the mixture was stirred at room temperature. After the temperature inside the reaction system reached 15° C., the reaction mixture was again stirred with cooling with ice for 1 hour. Further, the ice bath was removed, and the reaction mixture was stirred at room temperature for 3.0 hours. Then, 50 ml of an aqueous solution containing 10.0 g (79 mmol) of sodium sulfite was added. The reaction mixture was washed with methylene chloride twice, and then 170 ml of concentrated hydrochloric acid was added with cooling with ice. The mixture was extracted with ethyl acetate 3 times, and then the resultant organic layer was dried over anhydrous sodium sulfate. The solvent was distilled off under reduced pressure to give 119.3 g (yield 83%) of 3,4-dichloro-6-methylbenzoic acid as a crude product.

N.M.R. (ppm, solvent: acetone d-6, internal standard: tetramethylsilane): 2.59(3H,s), 7.52(H,s), 8.04(H,s)

Step (3)

92.1 g (421 mmol) of the 3,4-dichloro-6-methylbenzoic acid obtained in the above step (2) was dissolved in 550 ml of ethanol as both an esterifying agent and a solvent, 20 ml of concentrated sulfuric acid as an acid catalyst was added, and the mixture was refluxed under heat for 7 hours. The ethanol was distilled off under reduced pressure, ice water was added, and the mixture was extracted with ethyl acetate twice. The resultant organic layer was consecutively washed with a sodium carbonate aqueous solution and with a saturated sodium chloride aqueous solution and dried over anhydrous sodium sulfate. The solvent was distilled off under reduced pressure to give 103.4 g (yield 97%) of ethyl 3,4-dichloro-6-methylbenzoate as a crude product.

N.M.R. (ppm, solvent: deutero acetone, internal standard: tetramethylsilane): 1.39(3H,t), 2.57(3H,s), 4.35(2H,s), 7.52 (H,s), 7.98(H,s)

Step (4)

23.4 ml (268 mmol, 1.1 equivalents) of 3-mercaptopropionic acid was added to 215 ml of a solution of 53.7 g (231 mmol) of the ethyl 3,4-dichloro-6-methylbenzoate obtained in the step (3) and 37.9 g (268 mmol, 1.1 equivalents) of potassium carbonate in N,N-dimethylformamide (DMF) at room temperature, and then the mixture was stirred under heat at 120°~125° C. for 2 hours and 20 minutes. The reaction mixture was cooled to about 50° C., ethyl acetate and water were added, and for removing the DMF and neutral components, the reaction mixture was washed with ethyl acetate four times and with hexane once. Concentrated hydrochloric acid was added to the resultant aqueous layer to precipitate a crystal, the mixture was allowed to stand for a while, and the crystal was recovered by filtration and washed with water three times. The so-obtained crystal was dissolved in ethyl acetate, the obtained organic layer was washed with a saturated sodium chloride aqueous solution and dried over anhydrous sodium sulfate. The solvent was distilled off under reduced pressure to give 50.4 g (yield 60%) of 3-(2-chloro-4-ethoxycarbonyl-5-methylphenylthio)propionic acid as a crude product.

N.M.R. (ppm, solvent: deutero acetone, internal standard: tetramethylsilane): 1.38(3H,t), 2.58(3H,s), 2.79(2H,t), 3.35 (2H,t), 7.33(H,s), 7.87(H,s)

Step (5)

167 g of polyphosphoric acid as an acid catalyst was heated to 80°~85° C., and 47.7 g (157 mmol) of the 3-(2-chloro-4-ethoxycarbonyl-5-methylphenylthio) propionic acid obtained in the above step (4) was added thereto over 5 minutes. Then, the mixture was stirred under heat for 1 hour and 20 minutes. The reaction mixture was allowed to cool to room temperature and then added slowly to a mixture containing 191 g (1.80 mol) of sodium carbonate and ice, and the mixture was stirred at room temperature until the sodium carbonate was nearly dissolved. The reaction mixture was extracted with ethyl acetate twice, and the resultant organic layer was washed with a sodium carbonate aqueous solution twice, with water twice and with a saturated sodium chloride aqueous solution one time, and dried over anhydrous sodium sulfate. The solvent was distilled off under reduced pressure to give 41.3 g (yield 85%) of 8-chloro-6-ethoxycarbonyl-5-methylthiochroman-4-one as a crude product.

N.M.R. (ppm, solvent: deutero acetone, internal standard: tetramethylsilane): 1.38(3H,t), 2.58(3H,s), 2.9~3.1(2H,m), 3.3~3.5(2H,m), 4.34(2H,q), 7.81(H,s)

Step (6)

88.4 g (311 mmol) of the 8-chloro-6-ethoxycarbonyl-5-methylthiochroman-4-one obtained in the above step (5) was dissolved in 200 ml of ethanol, and further dissolved in 200 ml of dichloromethane. This solution was cooled to 5°~10° C., and 5.9 g (155 mmol) of sodium borohydride was added. The reaction mixture was stirred at the above temperature for 30 minutes, and further stirred at room temperature for 3 hours. Then, the reaction mixture was poured into 400 ml of a 5% hydrochloric acid aqueous solution and extracted with 900 ml of dichloromethane, and then the resultant organic layer was washed with a saturated sodium chloride aqueous solution and dried over anhydrous sodium sulfate. The solvent was distilled off to give 86.8 g (yield 97%) of 8-chloro-6-ethoxycarbonyl-5-methylthiochroman-4-ol.

N.M.R. (ppm, solvent: deutero acetone, internal standard: tetramethylsilane): 1.35(3H,t), 1.6~3.7 (5H,m), 2.62(3H,s), 4.1~4.8(H,bs), 4.32(2H,q), 5.13(H,m), 7.71(H,s)

Step (7)

25.8 g (90.0 mmol) of the 8-chloro-6-ethoxycarbonyl-5-methylthiochroman-4-ol obtained in the above step (6) was dissolved in 70 ml of acetic acid, 46.0 ml (0.45 mol, 5.0 equivalents) of a 30% hydrogen peroxide aqueous solution was added, and the mixture was stirred under heat at 80° C. for 4 hours. The reaction mixture was allowed to cool, and the resultant solid was recovered by filtration, washed with 200 ml of water and dried under reduced pressure to give 21.9 g (yield 95%) of 8-chloro-6-ethoxycarbonyl-4-hydroxy-5-methylthiochroman-1,1-dioxide.

N.M.R. (ppm, solvent: deutero chloroform, internal standard: tetramethylsilane): 1.40(3H,t), 2.59(3H,s), 2.5~4.2 (4H,m), 4.40(2H,q), 5.09(H,bs), 7.67(H,s)

Step (8)

10.0 g (31.3 mmol) of the 8-chloro-6-ethoxycarbonyl-4-hydroxy-5-methylthiochroman-1,1-dioxide obtained in the above step (7) was dissolved in 30 ml of ethanol, and 50 ml of a 16% potassium hydroxide aqueous solution and 6.1 g (93.3 mmol, 3.0 equivalents) of a zinc powder were added. The mixture was stirred under heat at 50° C. for 3 hours. After the completion of the reaction, the zinc powder was filtered off. While the reaction mixture was cooled, a 2N hydrochloric acid aqueous solution was added until the mixture had a pH of 1. Then, the mixture was extracted with ethyl acetate twice. An organic layer was washed with a saturated sodium chloride aqueous solution and then dried over anhydrous sodium sulfate, and the solvent was distilled off to give 11.5 g (yield 100%) of 4-hydroxy-5-methylthiochroman-6-carboxylic acid-1,1-dioxide.

N.M.R. (ppm, solvent: deutero acetone, internal standard: tetramethylsilane): 2.5~2.8(2H,m), 2.69(3H,s), 3.1~4.1(2H, m), 5.22(H,t), 7.75(H,d), 7.94(H,d) m.p. 172°~173° C.

Step (9)

3.0 g (11.8 mmol) of the 4-hydroxy-5-methylthiochroman-6-carboxylic acid-1,1-dioxide obtained in the above step (8) was dissolved in 10 ml of toluene, 0.1 ml of concentrated sulfuric acid was added, and the mixture was stirred under heat at 70° C. for 5 hours. After the completion of the reaction, while the reaction mixture was cooled, a saturated sodium hydrogencarbonate aqueous solution was added until the mixture had a pH of 10. Then, impurities were extracted with ethyl acetate. Then while an aqueous layer was in ice bath, 5% hydrochloric acid was added to the aqueous layer until it had a pH of 1. The mixture was extracted with ethyl acetate twice. An organic layer was washed with a saturated sodium chloride aqueous solution and dried over anhydrous sodium sulfate, and the solvent was distilled off to give 2.5 g (yield 89%) of 5-methyl-3,4-dehydrothiochroman-6-carboxylic acid-1,1-dioxide.

N.M.R. (ppm, solvent: deutero acetone, internal standard: tetramethylsilane): 2.62(3H,s), 4.10(2H,m), 6.45(H,ddd), 7.20(H,d), 7.83(H,d), 7.95(H,d) mp.183°~186° C.

Preparation Examples of the novel pyrazole derivative for achieving the first object of the present invention will be explained hereinafter.

Preparation Example 1

7.4 Grams (0.026 mol) of the 4,4,5,8-tetramethylthiochroman-6-carboxylic acid-1,1-dioxide obtained in Intermediate Preparation Example 1, 3.4 g (0.03 mol) of 1-ethyl-5-hydroxypyrazole and 6.22 g (0.03 mol) of DCC (N,N'-dicyclohexylcarbodiimide) were added to 50 ml of tert-amyl alcohol all at once, and the mixture was stirred at room temperature for 30 minutes. Then, 1.8 g (0.013 mol) of anhydrous potassium carbonate was added. The reaction mixture was allowed to react at 80° C. for 8 hours, then, the reaction solvent was distilled off under reduced pressure, and the resultant residue was separated into two layers by dispersing it in a 5% potassium carbonate aqueous solution and ethyl acetate. Further, an aqueous layer was adjusted to a pH of 1 with 5% hydrochloric acid, and a formed solid was recovered by filtration to give 6.13 g (yield 62%) of 4,4,5,8-tetramethyl-6-(1-ethyl-5-hydroxypyrazol-4-yl)carbonylthiochroman-1,1-dioxide.

Preparation Examples 2–5

Compounds shown in the right column of Table 1 were obtained in the same manner as in Preparation Example 1 except that raw materials shown in the left column of Table 1 were used in place of the 4,4,5,8-tetramethylthiochroman-6-carboxylic acid-1,1-dioxide in Preparation Example 1.

Preparation Example 6

4,4,5,8-Tetramethyl-6-(1,3-dimethyl-5-hydroxypyrazol-4-yl)carbonylthiochroman-1,1-dioxide in an amount of 0.46 g (yield 70%) was obtained in the same manner as in Preparation Example 1 except that 1,3-dimethyl-5-hydroxypyrazole was used in place of the 1-ethyl-5-hydroxypyrazole in Preparation Example 1.

Table 1 shows the raw materials used in Preparation Examples 1 to 6 and the structural formulae and yields of the compounds obtained in Preparation Examples 1 to 6. Table 2 shows the physical properties of the compounds.

TABLE 1

| Pre. Ex. | Raw material | Comp. No. | Structural formula | Yield (%) |
|---|---|---|---|---|
| 1 | (structure) | 1 | (structure) | 62 |
| 2 | (structure) | 2 | (structure) | 46 |
| 3 | (structure) | 3 | (structure) | 48 |
| 4 | (structure) | 4 | (structure) | 64 |
| 5 | (structure) | 5 | (structure) | 72 |
| 6 | (structure) | 6 | (structure) | 70 |

Pre. Ex. = Preparation Example

TABLE 2

| Pre. Ex. | Compound No. | N.M.R. Internal standard: tetramethylsilane Solvent: deuterochloroform | I.R. (cm⁻¹) KBr tablet method | Melting point (°C.) |
|---|---|---|---|---|
| 1 | 1 | 1.45(3H, t)1.55(6H, s)2.30–2.50(2H, m) 2.50(3H, s)2.80(3H, s)3.40–3.60(2H, m) 4.10(2H, q)6.20(H, s))7.20(H, s) | 2550–3500, 2950, 3000, 1630, 1290, 1130 | 208.8– 209.3 |
| 2 | 2 | 1.38(3H, t)1.60(6H, s)2.38–2.55(2H, m) 2.70(3H, s)3.40–3.54(2H, m)4.00(2H, q) 7.30(H, s)7.45(H, d)7.80(H, d)* | 2550–3500, 2950, 3000, 1620, 1290, 1130 | glass- like substance |
| 3 | 3 | 1.48(3H, t)1.70(6H, s)2.20–2.42(2H, m) | 2500–3500, | 263.7– |

TABLE 2-continued

| Pre. Ex. | Compound No. | N.M.R. Internal standard: tetramethylsilane Solvent: deutero chloroform | I.R. (cm$^{-1}$) KBr tablet method | Melting point (°C.) |
|---|---|---|---|---|
| | | 3.40–3.60(2H, m)4.08(2H, q)7.25(H, s) 7.42(H, s) | 2950, 3000 1660, 1320, 1160 | 263.9 |
| 4 | 4 | 1.38(6H, s)1.46(3H, t)1.90–2.10(2H, m) 3.00–3.20(2H, m)4.10(2H, q)7.20(H, d) 7.60(H, dd)7.75(H, s)7.95(H, d) | not measured | glass-like substance |
| 5 | 5 | 1.40(3H, t)1.45(6H, s)2.35–2.50(2H, m) 3.45–3.60(2H, m)4.05(2H, q)7.68(H, s) 7.86–8.05(3H, m)** | not measured | glass-like substance |
| 6 | 6 | 1.55(6H, s)1.65(3H, s)2.30–2.50(2H, m) 2.45(3H, s)2.80(3H, s)3.30–3.50(2H, m) 3.65(3H, s)7.00(H, s) | 2570–3700. 2950, 1630, 1290, 1130 | glass-like substance |

*Solvent: deuteroacetone
**Solvent: deuteromethanol

Preparation Example 7

0.70 Grams (1.9 mmol) of the of the 4,4,5,8-tetramethyl-6-(1-ethyl-5-hydroxypyrazol-4-yl)carbonylthiochroman-1,1-dioxide obtained in Preparation Example 1 was dissolved in 8 ml of methylene chloride. Then, 0.51 g (3.8 mmol) of potassium carbonate was dissolved in 5 ml of water, and the resultant solution was added. Further, 0.43 g (3.8 mmol) of methanesulfonyl chloride and 0.05 g (0.2 mmol) of benzyltriethylammonium chloride were added. The mixture was allowed to react at room temperature for 2 hours, and then further refluxed under heat for 2 hours. The reaction mixture was allowed to cool, and then a methylene chloride layer was collected and dried over anhydrous sodium sulfate. The solvent was distilled off under reduced pressure, and the resultant oil was purified by silica gel column chromatography to give 0.41 g (yield 49%) of 4,4,5,8-tetramethyl-6-(1-ethyl-5-methanesulfonyloxypyrazol-4-yl)carbonylthiochroman-1,1-dioxide (Compound 7).

Preparation Examples 8–17

Compounds 8 to 17 shown in the right column of Table 3 were obtained in the same manner as in Preparation Example 7 except that reaction reagents shown in the left column of Table 3 were used in place of methanesulfonyl chloride used in Preparation Example 8.

Preparation Example 18

0.5 Grams (1.3 mmol) of the of the 4,4,5,8-tetramethyl-6-(1-ethyl-5-hydroxypyrazol-4-yl)carbonyl-thiochroman-1,1-dioxide obtained in Preparation Example 1 was dissolved in 10 ml of methylene chloride, and 0.27 g (2.6 mmol) of triethylamine and 0.21 g (2.6 mmol) of acetyl chloride were added. The mixture was allowed to react at room temperature for 8 hours. Water was added to the reaction mixture to separate a methylene chloride layer, and the methylene chloride layer was dried over anhydrous sodium sulfate. The solvent was distilled off under reduced pressure, and the resultant oil was purified by silica gel column chromatography to give 0.32 g (yield 58%) of 4,4,5,8-tetramethyl-6-(1-ethyl-5-acetoxypyrazol-4-yl)carbonylthiochroman-1,1-dioxide (Compound 18).

Preparation Examples 19–23

Compounds 19 to 23 shown in the right column of Table 3 were obtained in the same manner as in Preparation Example 18 except that reaction reagents shown in the left column of Table 3 were used in place of the acetyl chloride used in Preparation Example 18.

Preparation Example 24

0.5Grams (1.3 mmol) of the of the 4,4,5,8-tetramethyl-6-(1-ethyl-5-hydroxypyrazol-4-yl)carbonylthiochroman-1,1-dioxide obtained in Preparation Example 1 was dissolved in 10 ml of methyl ethyl ketone, and 0.14 g (1.4 mmol) of chloroacetone and 0.37 g (2.6 mmol) of potassium carbonate were added. The mixture was refluxed under heat for 4 hours. The solvent was distilled off under reduced pressure, ethyl acetate was added to the resultant residue, and the mixture was washed with a saturated sodium bicarbonate aqueous solution. An organic layer was dried over anhydrous sodium sulfate, and the solvent was distilled off under reduced pressure. The resultant oil was purified by silica gel column chromatography to give 0.42 g (yield 73%) of Compound 24.

Preparation Example 25

Compound 25 in an amount of 0.61 g (yield 92%) was obtained in the same manner as in Preparation Example 24 except that phenacyl bromide was used in place of the chloroacetone used in Preparation Example 24.

Table 3 shows the structural formulae and yields of Compounds obtained in Preparation Examples 7 to 25. Table 4 shows the physical properties of the Compounds.

TABLE 3

| Pre. Ex. | reaction reagent | Comp. No. | Structural formula | Yield (%) |
|---|---|---|---|---|
| 7 | ClSO$_2$CH$_3$ | 7 | (structure) | 49 |
| 8 | ClSO$_2$C$_2$H$_5$ | 8 | (structure) | 82 |
| 9 | ClSO$_2$-n-C$_3$H$_7$ | 9 | (structure) | 41 |
| 10 | ClSO$_2$-n-C$_4$H$_9$ | 10 | (structure) | 65 |
| 11 | ClSO$_2$-n-C$_8$H$_{17}$ | 11 | (structure) | 49 |
| 12 | ClSO$_2$-C$_6$H$_4$-CH$_3$ | 12 | (structure) | 60 |
| 13 | ClSO$_2$-C$_6$H$_4$-NO$_2$ | 13 | (structure) | 62 |

TABLE 3-continued

| Pre. Ex. | reaction reagent | Comp. No. | Structural formula | Yield (%) |
|---|---|---|---|---|
| 14 | ClSO₂—C₆H₄—OCH₃ | 14 | (structure) | 73 |
| 15 | ClSO₂—C₆H₄—Cl | 15 | (structure) | 77 |
| 16 | 2-CH₃-C₆H₄-SO₂Cl | 16 | (structure) | 72 |
| 17 | 2,4-Cl₂-C₆H₃-SO₂Cl | 17 | (structure) | 72 |
| 18 | ClC(O)CH₃ | 18 | (structure) | 58 |
| 19 | ClC(O)C₂H₅ | 19 | (structure) | 61 |

TABLE 3-continued

| Pre. Ex. | reaction reagent | Comp. No. | Structural formula | Yield (%) |
|---|---|---|---|---|
| 20 | ClC(O)-n-C$_4$H$_9$ | 20 | (structure) | 54 |
| 21 | ClC(O)-n-C$_6$H$_{13}$ | 21 | (structure) | 86 |
| 22 | ClC(O)-cyclohexyl | 22 | (structure) | 74 |
| 23 | 2,4-dichlorobenzoyl chloride | 23 | (structure) | 67 |
| 24 | ClCH$_2$C(O)CH$_3$ | 24 | (structure) | 73 |
| 25 | BrCH$_2$C(O)-phenyl | 25 | (structure) | 92 |

TABLE 4

| Pre. Ex. | Comp. No. | N.M.R Internal standard: tetramethylsilane Solvent: deutero chloroform | I.R. (cm$^{-1}$) KBr tablet method | Melting point (°C.) |
|---|---|---|---|---|
| 7 | 7 | 1.55(3H, t)1.60(6H, s)2.30–2.60(2H, m) 2.50(3H, s)2.80(3H, s)3.30–3.60(2H, m) 3.65(3H, s)4.25(2H, q)7.10(H, s) 7.40(H, s) | 2980, 1665, 1140, 1300, 1200, 1390 | 202.2– 203.4 |
| 8 | 8 | 1.50(3H, t)1.60(6H, s)1.70(3H, t) 2.30–2.60(2H, m)2.50(3H, s)2.80(3H, s) 3.30–3.60(2H, m)3.80(2H, q)4.20(2H, q) 7.10(H, s)7.40(H, s) | 2940, 3000, 1660, 1180, 1140, 1290, 1390 | 164.1– 165.7 |
| 9 | 9 | 1.20(3H, t)1.55(3H, t)1.60(6H, s) 2.00–2.50(4H, m)2.50(3H, s)2.80(3H, s) 3.30–3.60(2H, m)8.60–3.90(2H, m) 4.20(2H, q)7.10(H, s)7.40(H, s) | 2970, 3000, 1680, 1140, 1300, 1190, 1390 | glass- like substance |
| 10 | 10 | 1.05(3H, t)1.40–1.80(5H, m)1.55(6H, s) 1.90–2.20(2H, m)2.25–2.50(2H, m)2.50 (3H, s)2.80(3H, s)3.30–3.60(2H, m) 3.65–3.90(2H, m)4.20(2H, q)7.10(H, s) 7.40(H, s) | 2900, 2980, 1660, 1130, 1300, 1180, 1380 | 177.9– 179.1 |
| 11 | 11 | 0.80–1.00(3H, m)1.20–1.80(13H, m) 1.60(6H, s)1.90–2.20(2H, m)2.25–2.50 (2H, m)2.50(3H, s)2.80(3H, s)3.30–3.60 (2H, m)3.65–3.90(2H, m)4.20(2H, q) 7.10(H, s)7.40(H, s) | 2880, 2950, 1670, 1140, 1300, 1380, 1390 | glass- like substance |
| 12 | 12 | 1.50(3H, t)1.60(6H, s)2.20–2.60(2H, m) 2.40(3H, s)2.50(3H, s)2.77(3H, s) 3.30–3.60(2H, m)4.20(2H, q)6.90(H, s) 7.40(2H, d)7.48(H, s)7.90(2H, d) | 2950, 3000, 1670, 1130, 1300, 1180, 1380 | 164.9– 166.3 |
| 13 | 13 | 1.57(3H, t)1.60(6H, s)2.20–2.50(2H, m) 2.40(3H, s)2.80(3H, s)3.30–3.57(2H, m) 4.25(2H, q)6.95(H, s)7.40(H, s) 8.40(4H, dd) | 2950, 1665, 1130, 1290, 1200, 1380 | 172.3– 174.2 |
| 14 | 14 | 1.50(3H, t)1.60(6H, s)2.20–2.50(2H, m) 2.40(3H, s)2.78(3H, s)3.30–3.50(2H, m) 3.90(3H, s)4.20(2H, q)6.90(H, s)7.10 (2H, d)7.48(H, s)7.90(2H, d) | 2950, 3000, 1660, 1100, 1290, 1180, 1380 | 174.9– 176.7 |
| 15 | 15 | 1.50(3H, t)1.57(6H, s)2.25–2.60(2H, m) 2.40(3H, s)2.78(3H, s)3.30–3.60(2H, m) 4.20(2H, q)6.90(H, s)7.45(H, s)7.60 (2H, d)8.00(2H, d) | 2980, 3000, 1680, 1140, 1300, 1200, 1400 | 145.3– 147.8 |
| 16 | 16 | 1.50(3H, t)1.53(6H, s)2.20–2.60(2H, m) 2.30(3H, s)2.73(3H, s)2.88(3H, s) 3.30–3.60(2H, m)4.20(2H, q)6.80(H, s) 7.25(H, s)7.30–8.00(4H, m) | 2950, 3000, 1680, 1130, 1290, 1200, 1390 | 182.1– 184.5 |
| 17 | 17 | 1.55(3H, t)1.60(6H, s)2.20–2.60(2H, m) 2.30(3H, s)2.75(3H, m)3.28–3.50(2H, m) 4.25(2H, q)6.90(H, s)7.25(H, s) 7.48–7.78(2H, m)7.85–8.00(H, m) | 2950, 3000, 1670, 1130, 1290, 1190, 1400 | 181.8– 185.8 |
| 18 | 18 | 1.45(3H, t)1.55(6H, s)2.20–2.60(2H, m) 2.25(3H, s)2.45(3H, s)2.79(3H, s) 3.27–3.58(2H, m)4.00(2H, q)7.00(H, s) 7.60(H, s) | 2950, 2980, 1660, 1120, 1160, 1290 | 187.7– 191.4 |
| 19 | 19 | 1.22(3H, t)1.47(3H, t)1.60(6H, s) 2.20–2.70(4H, m)2.45(3H, s)2.80(3H, s) 3.30–3.55(2H, m)4.00(2H, q)7.05(H, s) 7.60(H, s) | 2950, 3000, 1660, 1110, 1300, 1200, 1410 | 178.0– 179.6 |
| 20 | 20 | 0.98(3H, t)1.20–2.00(7H, m)1.58(6H, s) 2.20–2.70(4H, m)2.45(3H, s)2.78(3H, s) 3.30–3.55(2H, m)4.00(2H, q)7.05(H, s) 7.57(H, s) | 2880, 2980, 1670, 1140, 1300 | glass- like substance |
| 21 | 21 | 0.90(3H, t)1.10–1.90(11H, m)1.55(6H, s) 2.20–2.70(4H, m)2.48(3H, m)2.75(3H, s) 3.30–3.57(2H, m)4.00(2H, q)7.03(H, s) 7.55(H, s) | 2880, 2950, 1660, 1120, 1800, 1190 | glass- like substance |
| 22 | 22 | 1.42(3H, t)1.20–2.20(11H, m)1.55(6H, s) 2.25–2.65(2H, m)2.42(3H, s)2.80(3H, s) 3.30–3.55(2H, m)3.98(2H, q)7.05(H, s) 7.60(H, s) | 2950, 1660, 1140, 1300, 1200 | glass- like substance |
| 23 | 23 | 1.55(3H, t)1.58(6H, s)2.15–2.50(2H, m) 2.42(3H, s)2.75(3H, s)3.20–3.50(2H, m) 4.10(2H, q)7.05(H, s)7.35–7.60(2H, m) 7.70(H, s)7.75–7.90(H, m) | 2950, 3000, 1650, 1130, 1290, 1230 | 165.2– 169.0 |
| 24 | 24 | 1.48(3H, t)1.60(6H, s)2.20(3H, s) 2.28–250(2H, m)2.40(3H, s)2.80(3H, s) 3.30–3.55(2H, m)4.20(2H, q)5.40(2H, s) | 2940, 2980, 1640, 1130, 1290, 1410 | glass- like substance |

TABLE 4-continued

| Pre. Ex. | Comp. No. | N.M.R Internal standard: tetra-methylsilane Solvent: deutero chloroform | I.R. (cm⁻¹) KBr tablet method | Melting point (°C.) |
|---|---|---|---|---|
| 25 | 25 | 7.00(H, s)7.15(H, s) 1.50(6H, s)1.60(3H, t)2.20–2.50(2H, m) 2.35(3H, s)2.75(3H, s)3.25–3.50(2H, m) 4.30(2H, q)6.20(2H, s)6.95(H, s) 7.15(H, s)7.35–8.10(5H, m) | 2950, 1650, 1130, 1290, 1190 | 177.5– 179.5 |

Preparation Example 26

4,4,5,8-Tetramethyl-6-(1-methyl-5-hydroxypyrazol-4-yl)carbonylthiochroman-1,1-dioxide (Compound 26) in an amount of 1.7 g (yield 78%) was obtained in the same manner as in Preparation Example 1 except that 1-methyl-5-hydroxy-pyrazole was used in place of the 1-ethyl-5-hydroxypyrazole used in Preparation Example 1.

Preparation Example 27

0.80 Gram (2.2 mmol) of the 4,4,5,8-tetramethyl-6-(1-methyl-5-hydroxypyrazol-4-yl)carbonylthiochroman-1,1-dioxide obtained in Preparation Example 26 was dissolved in 20 ml of methylene chloride. Then, 0.40 g (2.9 mmol) of potassium carbonate was dissolved in 10 ml of water, and the resultant solution was added. Further, 0.43 g (3.0 mmol) of n-propanesulfonyl chloride and 0.05 g (0.2 mmol) of benzyltriethylammonium chloride were added. The mixture was allowed to react at room temperature for 24 hours, and after the completion of the reaction, a methylene chloride layer was collected and dried over anhydrous sodium sulfate. Then, the solvent was distilled off under reduced pressure. The resultant oil was purified by silica gel column chromatography to give 0.60 g (yield 59%) of 4,4,5,8-tetramethyl-6-(1-methyl-5-n-propanesulfonyloxypyrazol-4-yl)carbonyl-thiochroman-1,1-dioxide (Compound 27).

Preparation Example 28

4,4,5,8-Tetramethyl-6-(1-methyl-5-p-toluenesulfonyloxypyrazol-4-yl)carbonylthiochroman-1,1-dioxide (Compound 28) in an amount of 0.68 g (yield 64%) was obtained in the same manner as in Preparation Example 27 except that p-toluenesulfonyl chloride was used in place of the n-propanesulfonyl chloride used in Preparation Example 27.

Preparation Example 29

5-Chloro-4,4,8-trimethyl-6-(1-methyl-5-hydroxypyrazol-4-yl)carbonylthiochroman-1,1-dioxide in an amount of 0.52 g (yield 50%) was obtained in the same manner as in Preparation Example 1 except that 5-chloro-4,4,8-trimethylthiochroman-6-carboxylic acid-1,1-dioxide was used in place of the 4,4,5,8-tetramethylthiochroman-6-carboxylic acid-1,1-dioxide used in Preparation Example 1.

Table 5 shows the structural formulae and yields of Compounds obtained in Preparation Examples 26 to 29. Table 6 shows the physical properties of the Compounds.

TABLE 5

| Pre. Ex. | reaction reagent | Comp. No. | Structural formula | Yield (%) |
|---|---|---|---|---|
| 26 | (structure) | 26 | (structure) | 78 |
| 27 | (structure) | 27 | (structure) | 59 |

TABLE 5-continued

| Pre. Ex. | reaction reagent | Comp. No. | Structural formula | Yield (%) |
|---|---|---|---|---|
| 28 | [structure: pyrazole with N-CH₃, OH, C(=O), aryl with CH₃ groups, C(CH₃)₂, SO₂] | 28 | [structure: same with O-SO₂-C₆H₄-CH₃ group] | 64 |
| 29 | [structure: HO₂C-aryl with Cl, CH₃, C(CH₃)₂, SO₂] | 29 | [structure: pyrazole N-C₂H₅, OH, C(=O), aryl Cl, CH₃, C(CH₃)₂, SO₂] | 50 |

TABLE 6

| Pre. Ex. | Comp. No. | N.M.R. Internal standard: tetramethylsilane Solvent: deutero chloroform | I.R. (cm$^{-1}$) KBr tablet method | Melting point (°C.) |
|---|---|---|---|---|
| 26 | 26 | 1.60(6H, s)2.25–2.45(2H, m)2.50(3H, s) 2.70(3H, s)3.35–3.50(2H, m)3.70(3H, s) 4.40(H, 7' ͏-͏')7.10(H, s)7.50(H, s) | not measured | glass-like substance |
| 27 | 27 | 1.20(3H, t)1.55(6H, s)1.90–2.40(4H, m) 2.43(3H, s)2.80(3H, s)3.35–3.50(2H, m) 3.60–3.80(2H, m)3.90(3H, s)7.05(H, s) 7.40(H, s) | 2940, 2970 1670 1165, 1280 1380 | 191.2– 194.3 |
| 28 | 28 | 1.53(6H, s)2.25–2.45(2H, m)2.40(3H, s) 2.48(3H, s)2.74(3H, s)3.35–3.50(2H, m) 3.82(3H, s)6.90(H, s)7.29(H, s) 7.65(4H, dd) | 2940, 2970 1640 1160, 1285 1365 | 187.7– 191.2 |
| 29 | 29 | 1.20(3H, t)1.70(6H, s)2.20–2.45(2H, m) 2.60(3H, s)3.30–3.60(2H, m)4.00(2H, q) 6.95(H, s)7.05(H, s)* | 2950, 3000 1620, 1320 1130 | glass-like substance |

*solvent: deutero acetone

Preparation Example 30

2.7 Grams (7.1 mmol) of the 4,4,5,8-tetramethyl-6-(1,3-dimethyl-5-hydroxypyrazol-4-yl)carbonylthiochroman-1,1-dioxide obtained in Preparation Example 6 was dissolved in 20 ml of methylene chloride, and a solution of 1.5 g of potassium carbonate in 20 ml of methylene chloride was added. Further, 0.76 g (10.5 mmol) of n-propanesulfonyl chloride was dissolved in 10 ml of methylene chloride, and the resultant solution was added. Then, 50 mg of benzyltriethylammonium chloride was added. The mixture was allowed to react at room temperature for 7 hours, and then a methylene chloride layer was separated. The methylene chloride layer was dried over sodium sulfate, and then the solvent was distilled off under reduced pressure. When the resultant oily substance was washed with an ethyl acetate/ n-hexane mixed solvent (1:2 (V/V)) to form a solid, and the mixture was filtered to give 1.26 g(yield 74%) of 4,4,5,8-tetramethyl-6-(1,3-dimethyl-5-n-propanesulfonyloxypyrazol-4-yl)carbonylthiochroman-1,1-dioxide (Compound No. 30).

Preparation Examples 31–33

Compounds 31, 32 and 33 shown in the right column of Table 7 were obtained substantially in the same manner as in Preparation Example 30 except that reaction reagents shown in the left column of Table 7 were used in place of the n-propanesulfonyl chloride used in Preparation Example 30.

Table 7 shows the reaction reagents used in Preparation Examples 30 to 33 and the structural formulae and yields of Compounds obtained in Preparation Examples 30 to 33. Table 8 shows the physical properties of the Compounds.

TABLE 7

| Pre. Ex. | reaction reagent | Comp. No. | Structural formula | Yield (%) |
|---|---|---|---|---|
| 30 | ClO$_2$S-CH$_2$CH$_2$CH$_3$ | 30 | (pyrazole-propylsulfonate linked to trimethyl-sulfonyl-tetrahydronaphthalenyl ketone) | 74 |
| 31 | ClO$_2$S-C$_6$H$_4$-CH$_3$ (p-tolyl) | 31 | (pyrazole-p-tolylsulfonate linked structure) | 77 |
| 32 | ClO$_2$S-CH$_3$ | 32 | (pyrazole-methylsulfonate linked structure) | 50 |
| 33 | ClO$_2$S-C$_6$H$_4$-CH$_3$ (o-tolyl) | 33 | (pyrazole-o-tolylsulfonate linked structure) | 57 |

TABLE 8

| Pre. Ex. | Comp. No. | N.M.R. Internal standard: tetramethylsilane Solvent: deuterochloroform | I R (cm$^{-1}$) |
|---|---|---|---|
| 30 | 30 | 1.14(3H, t)1.57(6H, s) 1.97(3H, s)1.8–2.1(2H, m) 2.25–2.5(2H, m)2.46(3H, s) 2.77(3H, s)3.25–3.5(4H, m) 3.81(3H, s)7.01(H, s) | 3000, 2960 1670 1380, 1300 1190, 1130 |
| 31 | 31 | 1.55(6H, s)2.16(3H, s) 2.25–2.45(2H, m)2.43(3H, s) 2.47(3H, s) 2.72(3H, s)3.36–3.5(2H, m) 3.66(3H, s) 6.90(H, s)7.50(4H, dd) | 2950 1650, 1400 1295 1185, 1140 |
| 32 | 32 | 1.57(6H, s)1.91(3H, s) 2.3–2.5(2H, m) 2.46(3H, s)2.78(3H, s) 3.3–3.5(2H, m)3.33(3H, s) 3.82(3H, s)7.01(H, s) | 2970 1660 1390, 1300 1200, 1140 |
| 33 | 33 | 1.52(6H, s)2.03(3H, s) 2.25–2.5(2H, m)2.40(3H, s) | 2950 1660 |

TABLE 8-continued

| Pre. Ex. | Comp. No. | N.M.R.<br>Internal standard: tertamethylsilane<br>Solvent: deutero chloroform | I R (cm$^{-1}$) |
|---|---|---|---|
| | | 2.68(3H, s)2.7(3H, s)<br>3.3–3.5(2H, m)3.63(3H, s)<br>6.81(H, s)7.35–7.78(4H, m) | 1380<br>1285<br>1190, 1140 |

Preparation Example 34

1.0 Gram (2.7 mmol) of the 4,4,5,8-tetramethyl-6-(1,3-dimethyl-5-hydroxypyrazol-4-yl)carbonylthiochroman-1,1-dioxide obtained in Preparation Example 6 was dissolved in 10 ml of 1,2-dichloroethane, and further, 0.27 g (3.5 mmol) of pyridine and 10 mg of dimethylaminopyridine were added. Then, 0.64 g (3.5 mmol) of 4-nitrobenzoyl chloride was dropwise added, and the mixture was allowed to react at room temperature for 3 hours. To the reaction mixture was added 50 ml of water and then an organic layer was separated. The organic layer was consecutively washed with 10% hydrochloric acid, with a saturated sodium bicarbonate aqueous solution and with a saturated sodium chloride aqueous solution, and the solvent was distilled off under reduced pressure. The resultant solid was washed with ethyl acetate and filtered to give 0.86 g (yield 62%) of 4,4,5,8-tetramethyl-6-(1,3-dimethyl-5-(4-nitrophenyl)sulfonyloxypyrazol-4-yl)carbonylthiochroman-1,1-dioxide (Compound No. 34) in the form of a white crystal.

Preparation Examples 35–39

Compounds 35, 36, 37, 38 and 39 shown in the right column of Table 9 were obtained substantially in the same manner as in Preparation Example 34 except that reaction reagents shown in the left column of Table 9 were used in place of the nitrobenzoyl chloride used in Preparation Example 34.

Table 9 shows the reaction reagents used in Preparation Examples 34 to 39 and the structural formulae and yields of Compounds obtained in Preparation Examples 34 to 39. Table 10 shows the physical properties of the Compounds.

Preparation Example 40

1.0 Gram (2.7 mmol) of the 4,4,5,8-tetramethyl-6-(1,3-dimethyl-5-hydroxypyrazol-4-yl)carbonylthiochroman-1,1-dioxide obtained in Preparation Example 6 was dissolved in 10 ml of tetrahydrofuran, and further, 0.27 g (3.5 mmol) of pyridine and 90 mg of potassium iodide were added. Then, 0.63 g (3.5 mmol) of ethyl 2-bromopropionate was added, and the mixture was refluxed under heat for 7 hours. The reaction mixture was cooled to room temperature, and the solvent was distilled off under reduced pressure. The resultant residue was extracted by adding ethyl acetate, and the extract was consecutively washed with 10% hydrochloric acid, with a saturated sodium bicarbonate aqueous solution and with a saturated sodium chloride aqueous solution, and the solvent was distilled off under reduced pressure to give 0.57 g (yield 45%) of 4,4,5,8-tetramethyl-6-(1,3-dimethyl-5-(1-ethoxycarbonyl)ethoxypyrazol-4-yl)carbonylthiochroman-1,1-dioxide (Compound No. 40).

Preparation Example 41

Compound 41 shown in the right column of Table 9 was obtained substantially in the same manner as in Preparation Example 40 except that a reaction reagent shown in the left column of Table 9 was used in place of the ethyl 2-bromopropionate used in Preparation Example 40.

Table 9 shows the reaction reagents used in Preparation Examples 40 and 41 and the structural formulae and yields of Compounds obtained in Preparation Examples 40 and 41. Table 10 shows the physical properties of the Compounds.

TABLE 9

| Pre. Ex. | reaction reagent | Comp. No. | Structural formula | Yield (%) |
|---|---|---|---|---|
| 34 | ClOC–C6H4–NO2 | 34 | [structure] | 62 |

TABLE 9-continued

| Pre. Ex. | reaction reagent | Comp. No. | Structural formula | Yield (%) |
|---|---|---|---|---|
| 35 | ClOC-(2,4-dichlorophenyl) | 35 | (structure) | 56 |
| 36 | ClOC-phenyl | 36 | (structure) | 81 |
| 37 | ClOC-cyclohexyl | 37 | (structure) | 86 |
| 38 | ethyl chloroformate | 38 | (structure) | 81 |
| 39 | dimethylcarbamoyl chloride | 39 | (structure) | 46 |

TABLE 9-continued

| Pre. Ex. | reaction reagent | Comp. No. | Structural formula | Yield (%) |
|---|---|---|---|---|
| 40 | CH₃-CHBr-CO₂Et | 40 | (structure) | 45 |
| 41 | Br-CH₂-CO₂Me | 41 | (structure) | 31 |

TABLE 10 (No. 1)

| Pre. EX. | Comp. No. | N. M. R. Internal standard: tetramethylsilane Solvent: deuterochloroform | I R (cm⁻¹) |
|---|---|---|---|
| 34 | 34 | 1.37 (6H, s) 2.05 ~ 2.2 (2H, m) 2.38 (3H, s) 2.44 (3H, s) 2.62 (3H, s) 3.07 ~ 3.2 (2H, m) 3.66 (3H, s) 6.95 (H, s) 8.12 (4H, dd) | 2930 1760, 1640 1525 1280, 1240 |
| 35 | 35 | 1.35 (6H, s) 2.04 ~ 2.24 (2H, m) 2.39(6H. s) 2.72 (3H, s) 3.16 ~ 3.29 (2H, m) 3.66 (3H, s) 6.99 (H, s) 7.36 ~ 7.53 (3H, m) | 3000, 2970 1780, 1660 1300, 1230 1235 |
| 36 | 36 | 1.55 (6H, s) 2.0 ~ 2.13 (2H, m) 2.34 (3H, s) 2.52 (3H, s) 2.71 (3H, s) 3.03 ~ 3.17 (2H, m) 3.61 (3H, s) 7.00 (H, s) 7.48 ~ 7.7 (5H, m) | 2950 1770, 1650 1290, 1240 |
| 37 | 37 | 1.16 ~ 1.88 (11H, m) 1.56 (6H, s) 2.31 (3H, s) 2.41 (3H, s) 2.75 (3H, s) 2.25 ~ 2.45 (2H, m) 3.33 ~ 3.47 (2H, m) 3.55 (3H, s). 6.94 (H, s) | 2970 1795, 1655 1300 1135 |
| 38 | 38 | 1.32 (3H, t) 1.57 (6H, s) 2.24 ~ 2.5 (2H, m) 2.27 (3H, s) 2.42 (3H, s) 2.75 (3H, s) 3.33 ~ 3.47 (2H, m) 3.64 (3H, s) 4.16 (4H, q) 6.94 (H, s) | 2970 1795, 1670 1295, 1255 1130 |
| 39 | 39 | 1.55 (6H, s) 2.25 ~ 2.45 (2H, m) 2.43 (6H, s) 2.61 (3H, s) 2.74 (3H, s) 2.83 (3H, s) 3.3 ~ 3.5 (2H, m) 3.58 (3H, s) 6.99 (H, s) | 2950 1755, 1640 1280, 1140 |
| 40 | 40 | 1.26 (3H, s) 1.55 (6H, s) 1.60 (3H, s) 1.67 (3H, s) 2.3 ~ 2.5 (2H, m) 2.42 (3H, s) 2.76 (3H, s) 3.33 ~ 3.5 (2H, m) 3.76 (3H, s) 4.19 (2H, q) 5.40 (H, q) 6.95 (H, s) | 2930 1740 1630, 1500 1285, 1120 |
| 41 | 41 | 1.56 (6H, s) 1.64 (3H, s) 1.70 (3H, s) 2.3 ~ 2.45 (2H, m) 2.37 (3H, s) 2.76 (3H, s) 3.34 ~ 3.48 (2H, m) 3.77 (3H, s) 3.78 (3H, s) 5.02 (2H, s) 6.96 (H, s) | 2970 1775, 1645 1295, 1220 1130 |

Preparation Example 42

1.0 Gram (2.7 mmol) of the 4,4,5,8-tetramethyl-6-(1,3-dimethyl-5-hydroxypyrazol-4-yl)carbonylthiochroman-1,1-dioxide obtained in Preparation Example 6 was dissolved in 10 ml of 1,2-dichloroethane, and further, 0.26 g (3.2 mmol) of pyridine, 0.57 g (3.2 mmol) of isonicotinic acid chloride hydrochloride and 10 mg of benzyltriethylammonium chloride were added. The mixture was allowed to react at room temperature for 3 hours. The extraction of the reaction mixture was carried out by adding ethyl acetate, and the extract was consecutively washed with 10% hydrochloric acid, with a saturated sodium bicarbonate aqueous solution and with a saturated sodium chloride aqueous solution. The solvent was removed by filtration under reduced pressure, and the resultant oily substance was washed with an ethyl acetate/n-hexane mixed solvent (1:1 (V/V)) to form a solid. The mixture was filtered to give 1.0 g (yield 80%) of 4,4,5,8-tetramethyl-6-(1,3-dimethyl-5-(pyridin-4-yl) carbonyloxypyrazol-4-yl) carbonylthiochroman-1,1-dioxide (Compound No. 42).

Table 11 shows the reaction reagent used in Preparation Example 42 and the structural formula and yield of the Compound obtained in Preparation Example 42. Table 12 shows the physical properties of the Compound.

TABLE 11

| Pre. Ex. | reaction reagent | Comp. No. | Structural formula | Yield (%) |
|---|---|---|---|---|
| 42 | ClOC–⟨pyridyl⟩ | 42 | (structure) | 80 |

TABLE 12

| Pre. Ex. | Comp. No. | N. M. R.<br>Internal standard: tetramethylsilane<br>Solvent: deuterochloroform | I R (cm⁻¹) |
|---|---|---|---|
| 42 | 42 | 1.28 (6H, s) 2.35 (3H, s)<br>2.04 ~ 2.19 (2H, m)<br>2.43 (3H, s) 2.73 (3H, s)<br>3.08 ~ 3.22 (2H, m) 3.63 (3H, s)<br>6.99 (H, s) 7.47 ~ 7.54 (2H, m)<br>8.84 ~ 8.91 (2H, m) | 2970<br>1780, 1665<br>1300, 1260<br>1135 |

Preparation Example 43

A 100-ml eggplant type flask was charged with 1.0 g (3.9 mmol) of the 3,3,4,7-tetramethyl-2-hydrobenzo[b]thiophene-5-carboxylic acid-1,1-dioxide obtained in Intermediate Preparation Example 5, 0.48 g (4.3 mmol, 1.1 equivalents) of 1-ethyl-5-hydroxypyrazole and 100 ml of t-amyl alcohol. 1.04 g (5.0 mmol, 1.3 equivalents) of N,N'-dicyclohexylcarbodiimide (DCC) was added as a dehydrating agent, and the mixture was allowed to react at room temperature for 4 hours. To the reaction mixture was added 0.53 g (3.9 mmol, 1 equivalent) of potassium carbonate as a base, and the mixture was allowed to react further at 100° C. for 2 hours. After the completion of the reaction, the solvent was distilled off, and the residue was liquid-separated by adding 50 ml of ethyl acetate and 50 ml of water. The resultant aqueous layer was neutralized with 5% hydrochloric acid and then extracted with ethyl acetate, and the resultant organic layer was washed with a saturated sodium chloride aqueous solution and dried over anhydrous sodium sulfate. The solvent was distilled off to give 0.8 g (yield 57%) of 3,3,4,7-tetramethyl-5-(1-ethyl-5-hydroxypyrazol-4-yl)carbonyl-2-hydrobenzo[b]thiophene-1,1-dioxide (Compound No. 43).

Preparation Example 44

A 50-ml eggplant type flask was charged with 0.76 g (2.8 mmol) of 4,5,8-trimethylthiochroman-6-carboxylic acid-1,1-dioxide, 0.35 g (2.1 mmol, 1.1 equivalents) of 1-ethyl-5-hydroxypyrazole and 5 ml of t-amyl alcohol, and a solution of 0.70 g (3.4 mmol, 1.2 equivalents) of N,N'-dicyclohexylcarbodiimide (DCC) in 5 ml of t-amyl alcohol was added at room temperature. The mixture was allowed to react at room temperature for 2 hours, then, 0.58 g (2.8 mmol, 1.5 equivalents) of potassium carbonate was added, and the mixture was allowed to react at 100° C. for 6 hours. The solvent was distilled off, the residue was distributed into 30 ml of water and 30 ml of ethyl acetate, and a DCC urea material as an insoluble material was separated by filtration. An organic layer was extracted with 10 ml of a 5% potassium carbonate aqueous solution twice. The aqueous layers were combined and acidified with concentrated hydrochloric acid and thereafter extracted with ethyl acetate. The extract was washed with a saturated sodium chloride aqueous solution and dried over sodium sulfate, and the solvent was distilled off to give 0.77 g of a crude product. The crude product was recrystallized from ethanol to give 0.52 g (yield 51%) of 4,5,8-trimethyl-6-(1-ethyl-5-hydroxypyrazol-4-yl)carbonylthiochroman-1,1-dioxide (Compound No. 44).

Preparation Example 45

0.9 g (3.2 mmol) of the 4-ethyl-5,8-dimethylthiochroman-6-carboxylic acid-1,1-dioxide obtained in Intermediate Preparation Example 7, 0.43 g (3.8 mmol) of 1-ethyl-5-hydroxypyrazole and 0.79 g (3.8 mmol) of DCC were added to 5 ml of tert-amyl alcohol, and the mixture was allowed to react at room temperature for 2.5 hours. Thereafter, 0.31 g (2.2 mmol) of potassium carbonate was added, and the mixture was allowed to react at 80° C. for 4 hours. The reaction mixture was cooled to room temperature, and the solvent was distilled off under reduced pressure. A 2% sodium carbonate aqueous solution was added to the residue to dissolve the residue therein, and insolubles were filtered off. The resultant aqueous solution was washed with ethyl acetate, and 12N hydrochloric acid was added so that the mixture had a pH of 1. The resultant oily substance was extracted with ethyl acetate. An ethyl acetate layer was separated and washed with a saturated sodium chloride aqueous solution, and the solvent was distilled off under reduced pressure to give 1.2 g (yield 100%) of 4-ethyl-5,8-dimethyl-6-(1-ethyl-5-hydroxypyrazol-4-yl)carbonylthiochroman-1,1-dioxide (Compound No. 45).

Preparation Example 46

A 50-ml eggplant type flask was charged with 2.38 g (9.4 mmol) of 3,4,7-trimethyl-2-hydrobenzo[b]thiophene-5-carboxylic acid-1,1-dioxide, 1.15 g (10.3 mmol, 1.1 equivalents) of 1-ethyl-5-hydroxypyrazole and 10 ml of t-amyl alcohol, and a solution of 2.31 g (12.2 mmol, 1.3 equivalents) of DCC in 5 ml of t-amyl alcohol was added at room temperature. The mixture was allowed to react at room temperature for 2 hours, then 1.68 g (12.2 mmol, 3 equivalents) of potassium carbonate was added, and the mixture was allowed to react at 100° C. for 6 hours. The solvent was distilled off, the residue was distributed into 50 ml of water and 50 ml of ethyl acetate, and a DCC urea material as an insoluble one was filtered off. An organic layer was extracted with 15 ml of a 5% potassium carbonate aqueous solution twice, an aqueous layer was added. The aqueous layers were collected and acidified with concentrated hydrochloric acid and thereafter extracted with ethyl acetate. The extract was washed with a saturated sodium cTahloride aqueous solution and dried over sodium sulfate, and the solvent was distilled off to give 2.34 g of a crude product. The crude product was recrystallized from ethanol to give 1.39 g (yield 42%) of 3,4,7-trimethyl-5-(1-ethyl-5-hydroxypyrazol-4-yl)carbonyl-2-hydrobenzo[b]thiophene-1,1-dioxide (Compound No. 46).

Table 13 shows the structural formula of the starting materials used in Preparation Examples 43–46 and Compounds obtained in these Preparation Examples together with their yields, and Table 14 shows physical properties of Compounds obtained in Preparation Examples 43–46.

TABLE 14

| Pre. EX. | comp. No. | N. M. R. Internal standard: tetramethylsilane Solvent: deutero chloroform | I R (CM$^{-1}$) |
|---|---|---|---|
| 43 | 43 | 1.46 (3H, t) 1.67 (6H, g) | 3000 |
|  |  | 2.45 (3H, s) 2.64 (3H, g) | 1660 |
|  |  | 3.37 (2H, s) 4.08 (2H, q) | 1305 |
|  |  | 4.40 (H, s) | 1100 |
|  |  | 7.24 (H, s) 7.32 (H, s) |  |
| 44 | 44 | 1.37 (3H, d) 1.46 (3H, t) | 2980, 2950 |
|  |  | 2.1 ~ 3.9 (5H, m) 2.35 (3H, g) | 1625 |
|  |  | 2.76 (3H, s) | 1300, 1280 |
|  |  | 4.08 (2H, q) | 1125 |
|  |  | 6.0 (H, s) |  |
|  |  | 7.19 (H, g) 7.32 (H, g) |  |
| 45 | 45 | 1.06 (3H, t) 1.46 (3H, t) |  |
|  |  | 1.6 ~ 1.9 (2H, m) 2.32 (3H, s) | not |
|  |  | 2.35 ~ 2.65 (2H, m) | measured |
|  |  | 2.76 (3H, s) 2.9 ~ 3.8 (3H, m) |  |

TABLE 13

| Pre. Ex. | starting material | Comp. No. | Structural formula | Yield (%) |
|---|---|---|---|---|
| 43 | [structure] | 43 | [structure] | 57 |
| 44 | [structure] | 44 | [structure] | 51 |
| 45 | [structure] | 45 | [structure] | 100 |
| 46 | [structure] | 46 | [structure] | 42 |

TABLE 14-continued

| Pre. EX. | comp. No. | N. M. R. Internal standard: tetramethylsilane Solvent: deutero chloroform | I R (CM⁻¹) |
|---|---|---|---|
| 46 | 46 | 4.07 (2H, q) 4.94 (H, s) 7.19 (H, s) 7.32 (H, s) 1.47 (6H, T) 1.49 (3H, d) 2.36 (3H, s) 2.65 (3H, s) 3.1 ~ 3.9 (3H, M) 4.09 (2H, q) 6.39 (H, s) 7.29 (H, s) 7.35 (H, s) | 2980 1640 1295, 1175 1120 |

Preparation Example 47

Step (1)

A 100-ml eggplant type flask was charged with 0.96 g (4.4 mmol) of the 5,8-dimethyl-3,4-dehydrothiochroman-6-carboxylic acid obtained in Intermediate Preparation Example 5, 0.54 g (4.8 mmol, 1.1 equivalents) of 1-ethyl-5-hydroxypyrazole and 10 ml of dichloromethane, and 1.08 g (5.2 mmol, 1.2 equivalents) of DCC as a dehydrating agent was added. The mixture was allowed to react at room temperature for 2 hours. A DCC urea material was filtered off, and the filtrate was concentrated and then purified by silica gel column chromatography (developer solvent: ethyl acetate:n-hexane, 1:1 mixture). To 0.81 g (2.6 mmol) of the ester intermediate obtained by the above purification were added 0.53 g (3.9mmol, 1.5 equivalents) of potassium carbonate as a base and 2.0 ml of 1,4-dioxane, and the mixture was allowed to react further at 120° C. for 2 hours. After the completion of the reaction, the solvent was distilled off, and the residue was liquid-separated by adding 50 ml of ethyl acetate and 50 ml of water. The resultant aqueous layer was neutralized with 5% hydrochloric acid and then extracted with ethyl acetate. The resultant organic layer was washed with a saturated sodium chloride aqueous solution and dried over anhydrous sodium sulfate, and the solvent was distilled off to give 0.63 g (yield 57%) of 5,8-dimethyl-6-(1-ethyl-5-hydroxypyrazol-4-yl)carbonyl-3,4-dehydrothiochroman (Compound No. 47-1).

Step (2)

A 30-ml eggplant type flask was charged with 75 mg (0.24 mmol) of the 5,8-dimethyl-6-(1-ethyl-5-hydroxypyrazol-4-yl)carbonyl-3,4-dehydrothiochroman obtained in the above step (1), 7 mg of platinum oxide and 3 ml of ethanol, and the mixture was subjected to hydrogenation at room temperature under atmospheric pressure. After the reaction was carried out for 8 hours, the platinum oxide was filtered off, and the ethanol was distilled off to give 67 mg (yield 88%) of 5,8-dimethyl-6-(1-ethyl-5-hydroxypyrazol-4-yl)carbonylthiochroman (Compound No. 47-2). The yield through the steps (1) and (2) was 50%.

Preparation Example 48

5-Methyl-6-(1-ethyl-5-hydroxypyrazol-4-yl)carbonylthiochroman-1,1-dioxide (Compound No. 48) was obtained essentially in the same manner as in Preparation Example 47 except that 5-methyl-3,4-dehydrothiochroman-6-carboxylic acid-1,1-dioxide obtained in Intermediate Preparation Example 10 was used in place of the 5,8-dimethyl-3,4-dehydrothiochroman-6-carboxylic acid in Preparation Example 47.

Table 15 shows the structural formula of the starting materials used in Preparation Examples 47–48 and Compounds obtained in these Preparation Examples together with their yields, and Table 16 shows physical properties of Compounds obtained in Preparation Examples 47–48.

TABLE 15

| Pre. Ex. | starting material | Comp. No. | Structural formula | Yield (%) |
|---|---|---|---|---|
| 47 step 1 | [structure: HO₂C-dimethyl-dehydrothiochroman] | 47-1 | [structure] | 57 |
| 47 step 2 | [structure] | 47-2 | [structure] | 88 |
| 48 | [structure: HO₂C-methyl-dehydrothiochroman-1,1-dioxide] | 48 | [structure] | 62 |

TABLE 16

| Pre. Ex. | Comp No. | N.M.R. Internal standard:tetra-methylsilane Solvent : deutero chloroform | I R (cm⁻¹) |
|---|---|---|---|
| 47 | 47-1 | 1.45 (3H, t) 2.32 (3H, s) 2.37 (3H, s) 3.38 (2H, d) | not measured |
| Step 1 | | 4.07 (2H, q) 5.9 ~ 6.3 (1H, m) 6.79 (1H,d) 7.13(1H,s) 7.45 (1H, s) | |
| 47 step 2 | 47-2 | 1.43 (3H, t) 2.0 ~ 2.6 (8H, m) 2.7 ~ 3.1 (2H, m) 4.07 (2H, q) 7.11 (H, s) 7.45 (H, s) | not measured |
| 48 | 48 | 1.43 (3H, t) 2. 20(3H. s) 2.35 ~ 2.7 (3H, m) 2.8 ~ 3.0 (2H, m) 3.25 ~ 3.45 (2H, M) 4.0 (2H, q) 7.36 (H, d) 7.55 (H, s) 7.89 (H, d) | not measured |

Preparation Example 49

A 100-ml eggplant type flask was charged with 0.4 g (1.1 mmol) of the 3,3,4,7-tetramethyl-5-(1-ethyl-5-hydroxypyrazol-4-yl)carbonyl-2-hydrobenzo[b]thiophene-1,1-dioxide (Compound No. 43) obtained in Preparation Example 43, 10 ml of dichloromethane, 10 ml of water and 0.2 g (1.4 mmol) of potassium carbonate, and 0.19 g (1.3 mmol, 1.2 equivalents) of n-propanesulfonyl chloride was dropwise added at room temperature. 50 mg of benzyltriethylammonium chloride (BTEAC) was added, and the mixture was allowed to react at the above temperature for 2 hours. Then, the reaction mixture was liquid-separated. The resultant aqueous layer was extracted with dichloromethane, and the resultant organic layer was washed with a saturated sodium chloride aqueous solution and then dried over anhydrous sodium sulfate. The solvent was distilled off to give 0.45 g (yield 87%) of 3,3,4,7-tetramethyl-5-(1-ethyl-5-n-propanesulfonyloxypyrazol-4-yl)carbonyl-2-hydrobenzo[b]thiophene-1,1-dioxide (Compound No. 49).

Preparation Example 50

A 100-ml eggplant type flask was charged with 0.4 g (1.1 mmol) of 3,3,4,7-tetramethyl-5-(1-ethyl-5-hydroxypyrazol-4-yl)carbonyl-2-hydrobenzo[b]thiophene-1,1-dioxide obtained in said Preparation Example 43, 10 ml of dichloromethane, 10 ml of water and 0.2 g (1.4 mmol, 1.3 equivalents) of potassium carbonate, and 0.25 g (1.3 mmol, 1.2 equivalents) of p-toluenesulfonyl chloride was dropwise added at room temperature. 50 mg of benzyltriethylammonium chloride (BTEAC) was added, and the mixture was allowed to react at the above temperature for 2 hours and then liquid-separated. The resultant aqueous layer was extracted with dichloromethane, and the resultant organic layer was washed with a saturated sodium chloride aqueous solution and dried over anhydrous sodium sulfate. The solvent was distilled off to give 0.52 g (yield 91%) of 3,3,4,7-tetramethyl-5-(1-ethyl-5-p-toluenesulfonyloxypyrazol-4-yl)carbonyl-2-hydrobenzo[b]thiophene-5-carboxylic acid-1,1-dioxide (Compound No. 50).

Preparation Example 51

A 30-ml eggplant type flask was charged with 0.25 g (0.69 mmol) of 4,5,8-trimethyl-6-(1-ethyl-5-hydroxypyrazol-4-yl) carbonylthiochroman-1,1-dioxide, 5 ml of dichloromethane, 5 ml of water and 0.09 g (0.69 mmol, 1 equivalent) of potassium carbonate, and 0.11 g (0.76 mmol, 1.1 equivalents) of n-propanesulfonyl chloride was dropwise added with stirring at room temperature. 5 mg of benzyltriethylammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.35 g of a crude product, which was recrystalized from ethanol to give 0.31 g (yield 95%) of 4,5,8-trimethyl-6-(1-ethyl-5-n-propanesulfonyloxypyrazol-4-yl) carbonylthiochroman-1,1-dioxide (Compound No. 51).

Preparation Example 52

A 30-ml eggplant type flask was charged with 0.18 g (0.50 mmol) of 4,5,8-trimethyl-6-(1-ethyl-5-hydroxypyrazol-4-yl) carbonylthiochroman-1,1-dioxide, 5 ml of dichloromethane, 5 ml of water and 0.07 g (0.50 mmol, 1 equivalent) of potassium carbonate, and a solution of 0.10 g (0.55 mmol, 1.1 equivalents) of p-toluenesulfonyl chloride in 1 ml of dichloromethane was dropwise added with stirring at room temperature. 5 mg of benzyltriethylammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.30 g of a crude product, which was then recrystalized from ethanol to give 0.20 g (yield 77%) of 4,5,8-trimethyl-6-(1-ethyl-5-p-toluenesulfonyloxypyrazol-4-yl)carbonylthiochroman-1,1-dioxide (Compound No. 52).

Preparation Example 53

A 30-ml eggplant type flask was charged with 0.30 g (0.86 mmol) of 3,4,7-trimethyl-5-(1-ethyl-5-hydroxypyrazol-4-yl) carbonyl-2-hydrobenzo[b]thiophene-1,1-dioxide, 5 ml of dichloromethane, 5 ml of water and 0.12 g (0.69 mmol, 0.8 equivalent) of potassium carbonate, and 0.16 g (0.95 mmol, 1.1 equivalents) of n-propanesulfonyl chloride was dropwise added with stirring at room temperature. 5 mg of benzyltriethylammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.40 g of a crude product, and the crude product was recrystallized from ethanol to give 0.31 g (yield 79%) of 3,4,7-trimethyl-5-(1-ethyl-5-n-propanesulfonyloxypyrazol-4-yl)-2-hydrobenzo[b]thiophenecarbonyl-1,1-dioxide (Compound No. 53).

Preparation Example 54

A 30-ml eggplant type flask was charged with 0.25 g (0.72 mmol) of 3,4,7-trimethyl-5-(1-ethyl-5-hydroxypyrazol-4-yl)carbonyl-2-hydrobenzo[b]thiophene-1,1-dioxide, 5 ml of dichloromethane, 5 ml of water and 0.10 g (0.72 mmol, 1 equivalent) of potassium carbonate, and a solution of 0.15 g (0.72 mmol, 1.1 equivalents) of p-toluenesulfonyl chloride in 1 ml of dichloromethane was dropwise added with stirring at room temperature. 5 mg of benzyltriethylammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.34 g of a crude product, and the crude product was recrystallized from ethanol to give 0.29 g (yield 80%) of 3,4,7-trimethyl-5-(1-ethyl-p-toluenesulfonyloxy-pyrazol-4-yl)carbonyl-2-hydrobenzo[b]thiophene-1,1-dioxide (Compound No. 54).

Preparation Example 55

A 30-ml eggplant type flask was charged with 0.30 g (0.86 mmol) of 3,4,7-trimethyl-5-(1-ethyl-5-hydroxypyrazol-4-yl)carbonyl-2-hydrobenzo[b]thiophene-1,1-dioxide, 5 ml of dichloromethane, 5 ml of water and 0.12 g (0.69 mmol, 0.8 equivalent) of potassium carbonate, and 0.12 g (0.95 mmol, 1.1 equivalents) of ethanesulfonyl chloride was dropwise added with stirring at room temperature. 5 mg of benzyltriethyl-ammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.35 g of a crude product, and the crude product was recrystallized from ethanol to give 0.24 g (yield 63%) of 3,4,7-trimethyl-5-(1-ethyl-5-ethanesulfonyloxypyrazol-4-yl)-2-hydrobenzo[b]thiophenecarbonyl-1,1-dioxide (Compound No. 55).

Preparation Example 56

A 30-ml eggplant type flask was charged with 0.30 g (0.86 mmol) of 3,4,7-trimethyl-5-(1-ethyl-5-hydroxypyrazol-4-yl)carbonyl-2-hydrobenzo[b]thiophene-1,1-dioxide, 5 ml of dichloromethane and 0.09 g (1.1 mmol, 1.3 equivalents) of pyridine. While the mixture was stirred with cooling with ice, 0.10 g (0.95 mmol, 1.1 equivalents) of isobutyric acid chloride was dropwise added. The mixture was stirred under cooling with ice for 30 minutes and then allowed to react at room temperature for 2 hours. The reaction was terminated by adding 5 ml of water, and then an aqueous layer was extracted with dichloromethane. An organic layer was washed with 5% hydrochloric acid, with a 5% potassium carbonate aqueous solution and then with a saturated sodium chloride aqueous solution and dried over sodium sulfate. The solvent was distilled off to give 0.28 g of a crude product, and the crude product was recrystallized from ethanol to give 0.27 g (yield 75%) of 3,4,7-trimethyl-5-(1-ethyl-5-isopropylcarbonyl-oxypyrazol-4-yl)-2-hydrobenzo[b]-thiophenecarbonyl-1,1-dioxide (Compound No. 56).

Preparation Example 57

A 30-ml eggplant type flask was charged with 0.24 g (0.69 mmol) of 3,4,7-trimethyl-5-(1-ethyl-5-hydroxypyrazol-4-yl)carbonyl-2-hydrobenzo[b]thiophene-1,1-dioxide, 5 ml of dichloromethane and 0.07 g (0.89 mmol, 1.3 equivalents) of pyridine. While the mixture was stirred with cooling with ice, 0.11 g (0.76 mmol, 1.1 equivalents) of cyclohexanecarboxylic acid chloride was dropwise added. The mixture was stirred under cooling with ice for 30 minutes and then allowed to react at room temperature for 2 hours. The reaction was terminated by adding 5 ml of water, and then an aqueous layer was extracted with dichloromethane. An organic layer was washed with 5% hydrochloric acid, with a 5% potassium carbonate aqueous solution and then with a saturated sodium chloride aqueous solution and dried over sodium sulfate. The solvent was distilled off to give 0.35 g of a crude product, and the crude product was recrystallized from ethanol to give 0.32 g (yield 100%) of 3,4,7-trimethyl-5-(1-ethyl-5-carbonyloxypyrazol-4-yl)-2-hydrobenzo[b]thiophenecarbonyl-1,1-dioxide (Compound No. 57).

Preparation Example 58

A 30-ml eggplant type flask was charged with 0.30 g (0.86 mmol) of 5-methyl-6-(1-ethyl-5-hydroxypyrazol-4-yl)carbonylthiochroman-1,1-dioxide, 25 ml of dichloromethane, 5 ml of water and 0.14 g (0.86 mmol, 1 equivalent) of potassium carbonate. While the mixture was stirred at room temperature, 0.14 g (0.95 mmol, 1.1 equivalents) of n-propanesulfonyl chloride was dropwise added. 5 mg of benzyltriethylammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.2 g of a crude product, and the crude product was recrystallized from ethanol to give 0.18 g (yield 48%) of 5-methyl-6-(1-ethyl-5-n-propanesulfonyloxy-pyrazole-4-yl)carbonylthiochroman-1,1-dioxide (Compound No. 58).

Preparation Example 59

5 ml of dichloromethane, 5 ml of water and 0.10 g (0.72 mmol, 1 equivalent) of potassium carbonate were added to 0.26 g (0.75 mmol) of 5-methyl-6-(1-ethyl-5-hydroxypyrazol-4-yl)carbonylthiochroman-1,1-dioxide in a 30-ml eggplant type flask. While the mixture was stirred at room temperature, a solution of 0.16 g (0.82 mmol, 1.1 equivalents) of p-toluenesulfonyl chloride in 1 ml of dichloromethane was dropwise added at room temperature. 5 mg of benzyltriethyl-ammonium chloride (BTEAC) was added, and the mixture was allowed to react at the above temperature for 2 hours and then liquid-separated. An aqueous layer was extracted with dichloromethane. An organic layer was washed with a saturated sodium chloride aqueous solution and dried over sodium sulfate. The solvent was distilled off to give 0.24 g of a crude product, and the crude product was recrystallized from ethanol to give 0.14 g (yield 92%) of 5-methyl-6-(1-ethyl-p-toluenesulfonyl-oxypyrazol-4-yl)carbonylthiochroman-1,1-dioxide (Compound No. 59).

Preparation Example 60

5-Methyl-6-(1-ethyl-5-cyclohexylcarbonyl-oxypyrazol-4-yl)carbonylthiochroman-1,1-dioxide (Compound No. 60) was obtained essentially in the same manner as in Preparation Example 57 except that the 5-methyl-6-(1-ethyl-5-hydroxypyrazol-4-yl)carbonylthiochroman-1,1-dioxide obtained in Preparation Example 48 was used in place of the 3,4,7-trimethyl-5-(1-ethyl-5-hydroxypyrazol-4-yl)carbonyl-2-hydrobenzo[b]-thiophene-1,1-dioxide in Preparation Example 57.

Tables 17~19 show the structural formulae of reaction reagents used in Preparation Examples 49~60 and Compounds obtained in these Preparation Examples together with their yields, and Tables 20~23 show physical properties of Compounds obtained in Preparation Examples 49~60.

TABLE 17

| Pre. Ex. | reaction reagent | Comp. No. | Structural formula | Yield (%) |
|---|---|---|---|---|
| 49 | ClO$_2$S-CH$_2$CH$_2$CH$_3$ | 49 | (structure) | 87 |
| 50 | ClO$_2$S-C$_6$H$_4$-CH$_3$ | 50 | (structure) | 91 |
| 51 | ClO$_2$S-CH$_2$CH$_2$CH$_3$ | 51 | (structure) | 95 |
| 52 | ClO$_2$S-C$_6$H$_4$-CH$_3$ | 52 | (structure) | 77 |

TABLE 18

| Pre. Ex. | reaction reagent | Comp. No. | Structural formula | Yield (%) |
|---|---|---|---|---|
| 53 | ClO$_2$S-CH$_2$CH$_2$CH$_3$ | 53 | (structure) | 79 |

TABLE 18-continued

| Pre. Ex. | reaction reagent | Comp. No. | Structural formula | Yield (%) |
|---|---|---|---|---|
| 54 | ClO₂S–C₆H₄–CH₃ | 54 | (structure) | 80 |
| 55 | ClO₂S–CH₂CH₃ | 55 | (structure) | 63 |
| 56 | ClOC–CH(CH₃)₂ | 56 | (structure) | 75 |
| 57 | ClOC–C₆H₁₁ | 57 | (structure) | 100 |

TABLE 19

| Pre. Ex. | reaction reagent | Comp. No. | Structural formula | Yield (%) |
|---|---|---|---|---|
| 58 | ClO₂S–CH₂CH₂CH₃ | 58 | (structure) | 48 |

TABLE 19-continued

| Pre. Ex. | reaction reagent | Comp. No. | Structural formula | Yield (%) |
|---|---|---|---|---|
| 59 | ClO₂S–C₆H₄–CH₃ | 59 | [structure] | 92 |
| 60 | ClOC–cyclohexyl | 60 | [structure] | 54 |

TABLE 20

| Pre. EX. | Comp. No. | N.M.R. Internal standard:tetramethylsilane Solvent: deutero chloroform | I R (cm⁻¹) |
|---|---|---|---|
| 49 | 49 | 1.19 (3H, t) 1.52 (3H, t) 1.65 (3H, s) 1.9 ~ 2.3 (2H, m) 2.39 (3H, s) 2.63 (3H, s) 3.37 (2H, s) 3.6 ~ 3.8 (2H, m) 4.29 (2H, q) 7.16 (H, s) 7.44 (H, s) | 2966 1660 1300 1120 |
| 50 | 50 | 1.59 (3H, t) 1.65 (6H, s) 2.38 (3H, s) 2.48 (3H, s) 2.57 (3H, s) 3.36 (2H, s) 4.16 (2H, q) 7.20 (H, s) 7.65 (4H, dd) | 3000 1670 1305 1140 |

TABLE 21

| Pre. EX. | Comp. No. | N.M.R. Internal standard:tetramethylsilane Solvent: deutero chloroform | I R (cm⁻¹) |
|---|---|---|---|
| 51 | 51 | 1.18 (3H, t) 1.36 (3H, d) 1.52 (3H, t) 1.9 ~ 3.9 (7H, m) 2.29 (3H, s) 2.75 (3H, s) 3.6 ~ 3.9 (2H, m) 4.22 (2H, q) 7.11 (H, s) 7.44 (H, s) | 2930, 2970 1650 1375, 1295 1165, 1120 |
| 52 | 52 | 1.34 (3H, d) 1.50 (3H, t) 2.1 ~ 3.9 (5H, m) 2.26 (3H, s) 2.47 (3H, s) 2.72 (3H, s) 4.18 (2H, q) 6.96 (H, s) 7.37 (H, s) 7.67 (4H, dd) | 2960 1670 1385, 1310 1130 |
| 53 | 53 | 1.18 (3H, t) 1.44 ~ 1.6 (6H, m) 1.9 ~ 2.24 (2H, m) 2.29 (3H, s) 2.63 (3H, s) 3.2 ~ 3.8 (5H, m) 4.22 (2H, q) 7.20 (H, s) 7.45 (H, s) | 3000 1670 1400, 1310 1185, 1135 |
| 54 | 54 | 1.41 ~ 1.63 (6H, m) 2.28 (3H, s) 2.47 (3H, s) 2.57 (3H, s) 3.2 ~ 3.8 (3H, m) 4.15 (2H, q) 7.06 (H, s) 7.37 (H, s) 7.67 (4H, dd) | 2990 1660 1370, 1300 1275, 1200 1120 |

TABLE 22

| Pre. EX. | Comp No. | N.M.R. Internal standard: tetramethylsilane Solvent: deutero chloroform | I R (cm⁻¹) |
|---|---|---|---|
| 55 | 55 | 1.44 1.73 (6H, m) 2.29 (3H, s) 2.63 (3H, s) 3.2 ~ 3.89 (5H, m) 4.23 (2H, q) 7.20 (H, s) 7.45 (H, s) | 3000 1675 1390, 1310 1185, 1140 |
| 56 | 56 | 1.28 ~ 1.52 (12H, m) 2.27 (3H, s) 2.61 (3H, s) 2.65 ~ 2.96 (H, m) 3.18 ~ 3.78 (3H, m) 4.02 (2H, q) 7.17 (H, s) 7.54 (H, s) | 2990 1790 1660, 1300 |
| 57 | 57 | 1.43 (3H, t) 1.47 (3H, d) 2.26 (3H, s) 2.61 (3H, s) 1.2 ~ 2.5 (11H, m) 3.2 ~ 3.8 (3H, m) 4.00 (2H, q) 7.16 (H, s) 7.58 (H, s) | 2950 1780, 1660 1300 |
| 58 | 58 | 1.18 (3H, t) 1.52 (3H, t) 2.25 (3H, s) 2.0 ~ 2.65 (4H, m) 2.8 ~ 3.05 (2H, m) 3.3 ~ 3.8 (4H, m) 4.22 (2H, q) | not measured |

TABLE 22-continued

| Pre. EX. | Comp No. | N. M. R.<br>Internal standard: tetra-methylsilane<br>Solvent: deutero chloroform | I R (cm$^{-1}$) |
|---|---|---|---|
| | | 7.40 (H, d) 7.44 (H, s)<br>7.90 (H, d) | |

TABLE 23

| Pre. Ex. | Comp. No. | N. M. R.<br>Internal standard: tetra-methylsilane<br>Solvent: deutero chloroform | I R (cm$^{-1}$) |
|---|---|---|---|
| 59 | 59 | 1.50 (3H, t)<br>2.20 (3H, s) 2.45 (3H, s)<br>2.3 ~ 2.7 (2H, m)<br>2.85 ~ 3.0 (2H, m)<br>3.3 ~ 3.5 (2H, m) 4.15 (2H, q)<br>7.2 ~ 7.55 (4H, m) 7.85 (2H, d) | not measured |
| 60 | 60 | 1.43 (3H, t) 2.21 (3H, s)<br>1.16 ~ 2.1 (10H, m)<br>2.33 ~ 2.69 (3H, m)<br>2.84 ~ 2.98 (2H, m)<br>3.28 ~ 3.42 (2H, m) 4.00 (2H, q)<br>7.36 (H, d) 7.55(H, s)<br>7.89 (H, d) | not measured |

Examples of the herbicide which achieves the second object of the present invention will be described hereinafter.

Herbicide Examples (1) Preparation of Herbicide

97 Parts by weight of talc (trade name: Zeaklite) as a carrier, 1.5 parts by weight of alkylarylsulfonic acid (trade name: Neoplex, supplied by Kao-Atlas K.K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier and 10 parts by weight of each of Compounds obtained in the above Preparation Examples were uniformly pulverized and mixed to obtain herbicides. Further, for Herbicide Comparative Examples, comparative herbicides were prepared by uniformly pulverizing and mixing 90 parts by weight of the above carrier and 10 parts by weight of each of the following Compounds x, y, A, B and C.

Compound (x): Pyrazolate, commercially available herbicide

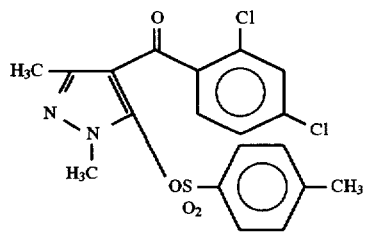

Compound (y): Compound disclosed in JP-A-63-122672

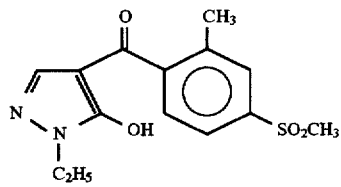

Compound (A): Compound No. 35 disclosed in JP-A-2-173

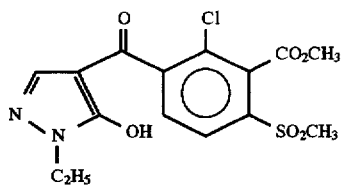

Compound (B): Compound No. 66 disclosed in International Laid-open Patent Publication No. WO93/18031

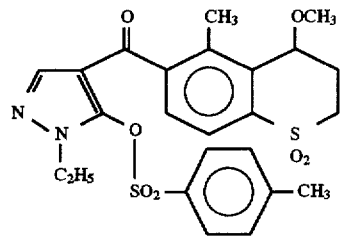

Compound (C): Compound No. b-3 disclosed in Japanese Patent Application No. 4-185526

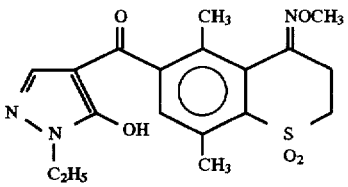

(2) Biological Test (Foliar Treatment Test, Herbicide Examples 1 and 2 and Herbicide Comparative Examples 1 and 2)

Seeds of weeds such as large crabgrass, barnyard grass, green foxtail, cocklebur, velvetleaf and slender amaranth and seeds of corn, wheat and barley were sown in 1/5,000-are Wagner pots filled with upland soil, and covered with upland soil. The seeds were grown in a greenhouse, and at the stage of 1~2 leaves of these plants, a predetermined amount of the herbicide prepared in the above (1) was suspended in water and uniformly sprayed onto leaf and stalk portions at a rate of 200 liter/10 are. Thereafter, the plants were grown in the greenhouse, and on 20th day after the treatment, the herbicide was evaluated for herbicidal efficacy. Table 24 shows the results.

The herbicidal efficacy and phytotoxcity to crops were shown on the basis of the following ratings.

The ratio of remaining plant weight to non-treated was determined on the basis of the ratio of remaining plant weight to non-treated=(remaining plant weight in treated plot/remaining plant weight in non-treated plot)×100. This is also applicable to biological tests hereinafter.

| (Ratings) | |
| --- | --- |
| Herbicidal efficacy | Ratio of remaining plant weight to non-treated (%) |
| 0 | 81–100 |
| 1 | 61–80 |
| 2 | 41–60 |
| 3 | 21–40 |
| 4 | 1–20 |
| 5 | 0 |
| Phytotoxicity to crops | Ratio of remaining plant weight to non-treated (%) |
| − | 100 |
| ± | 95–99 |
| + | 90–94 |
| ++ | 80–89 |
| +++ | 0–79 | upland soil. Then, a predetermined amount of the herbicide prepared in the above (1) was suspended in water and uniformly sprayed onto the soil surface. Thereafter, the plants were grown in the greenhouse, and on 20th day after the treatment, the herbicide was evaluated for herbicidal efficacy. Table 25 shows the results.

The herbicidal efficacy and the phytotoxicity to crops are shown on the basis of the ratings described in (2) Foliar treatment test.

TABLE 24

| No. | Comp'd used | Dosage ($g^{a.i.}$/ are) | Herbicidal Efficacy | | | | | | Phytotoxicity | | |
| --- | --- | --- | --- | --- | --- | --- | --- | --- | --- | --- | --- |
| | | | large crabgrass | barnyard grass | green foxtail | cocklebur | velvet-leaf | slender amaranth | corn | wheat | barley |
| Herbicide Example 1 | 1 | 10 | 5 | 5 | 5 | 5 | 5 | 5 | — | — | — |
| Herbicide Example 1 | 1 | 3 | 5 | 5 | 5 | 5 | 5 | 5 | — | — | — |
| Herbicide Example 2 | 2 | 10 | 5 | 5 | 5 | 5 | 5 | 5 | — | — | — |
| Herbicide Example 2 | 2 | 3 | 5 | 4 | 3 | 5 | 4 | 3 | — | — | — |
| Herbicide Comp. Exam. 1 | x | 10 | 0 | 0 | 0 | 0 | 0 | 1 | — | — | — |
| Herbicide Comp. Exam. 2 | y | 3 | 0 | 0 | 0 | 3 | 3 | 2 | — | — | — |

(3) Biological Test (Upland Soil Treatment Test, Herbicide Examples 3 and 4 and Herbicide Comparative Examples 3 and 4)

Seeds of weeds such as large crabgrass, barnyardgrass, green foxtail, cocklebur, velvetleaf and slender amaranth and seeds of corn, wheat and barley were sown in 1/5,000-are Wagner pots filled with upland soil, and covered with

| No. | Comp'd used | Dosage ($g^{a.i.}$/ are) | Herbicidal Efficacy | | | | | | Phytotoxicity | | |
| --- | --- | --- | --- | --- | --- | --- | --- | --- | --- | --- | --- |
| | | | large crabgrass | barnyard grass | green foxtail | cocklebur | velvet-leaf | slender amaranth | corn | wheat | barley |
| Herbicide Example 3 | 1 | 10 | 5 | 5 | 5 | 5 | 5 | 5 | — | — | — |
| Herbicide Example 3 | 1 | 3 | 5 | 5 | 5 | 5 | 5 | 5 | — | — | — |
| Herbicide Example 4 | 2 | 10 | 5 | 5 | 5 | 5 | 5 | 5 | — | — | — |
| Herbicide Example 4 | 2 | 3 | 5 | 5 | 5 | 5 | 5 | 5 | — | — | — |
| Herbicide Comp. Exam. 3 | x | 10 | 0 | 0 | 0 | 0 | 0 | 0 | — | — | — |
| Herbicide Comp. Exam. 4 | y | 3 | 3 | 2 | 2 | 0 | 0 | 0 | — | — | — |

(4) Biological Test (Submergence Soil Treatment Test, Herbicide Examples 5~9 and Comparative Examples 5~8 and Reference Examples 1 and 2)

1/15,500-are porcelain pots were filled with paddy field soil, and seeds of barnyard grass and umbrella plant were sown in a surface layer of the soil, and paddy rice at the 2-leaf stage was transplanted. Then, the weeds were treated by uniformly spraying a diluted solution of a predetermined amount of the herbicide prepared in the above (1) onto the water surface at the time of germination of the weeds, and then the pots were allowed to stand in a greenhouse while water was properly sprayed. Twenty days after the treatment with the herbicide solution, the herbicidal efficacy and phytotoxicity to paddy rice were inspected, and Table 26 shows the results. The dosage of each herbicide is shown as an amount of the active ingredient per 10 ares. Further, air-dried weights were measured, and the herbicidal efficacy and the phytotoxicity to the paddy rice were shown as follows.

| (Ratings) | |
|---|---|
| Herbicidal efficacy | Ratio of remaining plant weight to non-treated (%) |
| 0 | 81–100 |
| 1 | 61–80 |
| 2 | 41–60 |
| 3 | 21–40 |
| 4 | 1–20 |
| 5 | 0 |
| Phytotoxicity to paddy rice | Ratio of remaining plant weight to non-treated (%) |
| 0 | 100 |
| 1 | 95–99 |
| 2 | 90–94 |
| 3 | 80–89 |
| 4 | 0–79 |

TABLE 26

| No. | Comp'd used | Dosage ($g^{a.i.}$/ 10 are) | Herbicidal Efficacy | | Phytotoxicity to paddy rice |
|---|---|---|---|---|---|
| | | | barn-yard grass | um-brella plant | |
| Herbicide Example 5 | 10 | 1 | 5 | 5 | 0 |
| Herbicide Example 6 | 11 | 1 | 5 | 5 | 0 |
| Herbicide Example 7 | 14 | 1 | 5 | 3 | 0 |
| Herbicide Example 8 | 16 | 3 | 5 | 5 | 0 |
| Herbicide Example 9 | // | 1 | 5 | 2 | 0 |
| Comparative Example 5 | Comp'd A | 3 | 4 | 4 | 4 |
| Comparative Example 6 | // | 1 | 1 | 0 | 0 |
| Comparative Example 7 | Comp'd B | 3 | 5 | 5 | 4 |
| Comparative Example 8 | // | 1 | 2 | 3 | 0 |
| Reference Exam. 1 | Comp'd C | 10 | 4 | 5 | 5 |
| Reference Exam. 2 | // | 3 | 0 | 3 | 2 | a.i. = active ingredient (5) Biological Test (Upland Soil Treatment Test, Herbicide Examples 10~26 and Comparative Example 9)

Seeds of weeds such as large crabgrass, barnyard grass, green foxtail, cocklebur, velvetleaf and slender amaranth and seeds of corn, wheat and barley were sown in 1/5,000-are Wagner pots filled with upland soil, and covered with upland soil. Then, a predetermined amount of the herbicide prepared in the above (1) was suspended in water and uniformly sprayed onto the soil surface. Thereafter, the plants were grown in the greenhouse, and on 20th day after the treatment, the herbicide was evaluated for herbicidal efficacy. Table 27 shows the results.

The dosage of each herbicide is indicated as an amount of the active ingredient per hectare. Further, air-dried weight were measured, and herbicidal efficacy and the phytotoxicity to corn are shown on the basis of the ratings described below.

| (Ratings) | |
|---|---|
| Herbicidal efficacy | Ratio of remaining plant weight to non-treated (%) |
| 0 | 81–100 |
| 1 | 61–80 |
| 2 | 41–60 |
| 3 | 21–40 |
| 4 | 1–20 |
| 5 | 0 |
| Phytotoxicity to corn | Ratio of remaining plant weight to non-treated (%) |
| 0 | 100 |
| 1 | 95–99 |
| 2 | 90–94 |
| 3 | 80–89 |
| 4 | 0–79 |

TABLE 27

| No. | Comp'd used | Dosage (g a.i./ hectare) | Herbicidal efficacy large crabgrass | barnyard grass | green foxtail | cockle- bur | velvet- leaf | slender amaranth | Phyto- toxicity to corn |
|---|---|---|---|---|---|---|---|---|---|
| Herbicide Example 10 | 1 | 100 | 5 | 5 | 5 | 5 | 5 | 5 | 0 |
| Herbicide Example 11 | 2 | 100 | 5 | 5 | 5 | 5 | 5 | 5 | 0 |
| Herbicide Example 12 | 7 | 100 | 5 | 5 | 4 | 5 | 5 | 5 | 0 |
| Herbicide Example 13 | 8 | 100 | 5 | 4 | 4 | 5 | 5 | — | 0 |
| Herbicide Example 14 | 9 | 100 | 5 | 5 | 5 | 5 | 5 | 5 | 0 |
| Herbicide Example 15 | 10 | 100 | 5 | 5 | 2 | 3 | 5 | 5 | 0 |
| Herbicide Example 16 | 11 | 100 | 5 | 3 | 2 | 3 | 5 | 1 | 0 |
| Herbicide Example 17 | 12 | 100 | 5 | 5 | 1 | — | 5 | 5 | 0 |
| Herbicide Example 18 | 13 | 100 | 5 | 3 | 2 | 5 | 5 | 2 | 0 |
| Herbicide Example 19 | 14 | 100 | 5 | 5 | 2 | 5 | 5 | 5 | 0 |
| Herbicide Example 20 | 16 | 100 | 5 | 5 | 5 | 5 | 5 | 5 | 0 |
| Herbicide Example 21 | 18 | 100 | 5 | 5 | 4 | 5 | 5 | 5 | 0 |
| Herbicide Example 22 | 19 | 100 | 5 | 5 | 2 | 5 | 5 | 5 | 0 |
| Herbicide Example 23 | 20 | 100 | 5 | 3 | 2 | 5 | 5 | — | 0 |
| Herbicide Example 24 | 21 | 100 | 5 | 5 | 4 | 5 | 5 | 5 | 0 |
| Herbicide Example 25 | 24 | 100 | 5 | 5 | 2 | 5 | 5 | 5 | 0 |
| Herbicide Example 26 | 25 | 100 | 5 | 2 | 2 | 5 | 5 | 5 | 0 |
| Comparative Example 9 | Comp'd A | 100 | 1 | 2 | 4 | 1 | 5 | 3 | 0 | a.i. = active ingredient (6) Biological Test (Upland Soil Treatment Test, Herbicide Examples 27–42 and Comparative Example 10).

Seeds of weeds such as large crabgrass, barnyard grass, green fox-tail, cocklebur, velvetleaf and slender amaranth and seeds of corn, wheat and barley were sown in 1/5,000-are Wagner pots filled with upland soil, and covered with upland soil. Then, a predetermined amount of the herbicide prepared in the above (1) was suspended in water and uniformly sprayed onto the soil surface. Thereafter, the plants were grown in the greenhouse, and on 20th day after the treatment, the herbicide was evaluated for herbicidal efficacy. Table 28 shows the results.

The dosage of each herbicide is indicated as an amount of the active ingredient per hectare. Further, air-dried weight were measured and the herbicidal efficacy and the phytotoxicity to corn are shown on the basis of the ratings described below.

| (Ratings) | |
|---|---|
| Herbicidal efficacy | Ratio of remaining plant weight to non-treated (%) |
| 0 | 81–100 |
| 1 | 61–80 |
| 2 | 41–60 |
| 3 | 21–40 |
| 4 | 1–20 |
| 5 | 0 |
| Phytotoxicity to corn | Ratio of remaining plant weight to non-treated (%) |
| 0 | 100 |
| 1 | 95–99 |
| 2 | 90–94 |
| 3 | 80–89 |
| 4 | 0–79 |

TABLE 28

| Herbicide Exam. No. | Comp'd used | Dosage (g/ hectare) | Herbicidal efficacy (A) | (B) | (C) | (D) | (E) | (F) | Phytotoxicity to corn |
|---|---|---|---|---|---|---|---|---|---|
| 27 | 29 | 100 | 5 | 4 | 4 | 5 | 5 | 5 | 0 |
| 28 | 30 | 100 | 5 | 4 | 3 | 1 | 5 | 5 | 0 |
| 29 | 31 | 100 | 5 | 4 | 3 | 1 | 4 | 5 | 0 |
| 30 | 44 | 100 | 5 | 5 | 5 | 5 | 5 | 5 | 0 |
| 31 | 46 | 100 | 5 | 5 | 2 | 2 | 1 | 1 | 0 |
| 32 | 48 | 100 | 5 | 5 | 1 | 1 | 5 | 5 | 0 |

TABLE 28-continued

| Herbicide Exam. No. | Comp'd used | Dosage (g/ hectare) | Herbicidal efficacy | | | | | | Phyto-toxicity to corn |
|---|---|---|---|---|---|---|---|---|---|
| | | | (A) | (B) | (C) | (D) | (E) | (F) | |
| 33 | 49 | 100 | 5 | 5 | 5 | 5 | 5 | 5 | 0 |
| 34 | 50 | 100 | 4 | 5 | 5 | 5 | 5 | 4 | 0 |
| 35 | 51 | 100 | 5 | 5 | 5 | 5 | 5 | 5 | 0 |
| 36 | 52 | 100 | 5 | 5 | 5 | 5 | 5 | 5 | 0 |
| 37 | 53 | 100 | 5 | 5 | 4 | 2 | 5 | 1 | 0 |
| 38 | 54 | 100 | 5 | 5 | 4 | 1 | 5 | 1 | 0 |
| 39 | 56 | 100 | 5 | 5 | 4 | 5 | 5 | 5 | 0 |
| 40 | 57 | 100 | 5 | 5 | 4 | 5 | 5 | 5 | 0 |
| 41 | 59 | 100 | 5 | 5 | 4 | 0 | 5 | 5 | 0 |
| 42 | 60 | 100 | 5 | 3 | 3 | 1 | 5 | 5 | 0 |
| Comp. Exam. 10 | Conp'd A | 100 | 1 | 2 | 4 | 1 | 5 | 3 | 0 |

(A): large crabgrass
(B): barnyard grass
(C): green foxtail
(D): cocklebur
(E): velvetleaf
(F): slender amaranth (7) Biological Test (Foliar Treatment Test, Herbicide Examples 43–47 and Comparative Examples 11 and 12).

Seeds of weeds such as large crabgrass, barnyardgrass, green foxtail, cocklebur, velvetleaf and slender amaranth and seeds of corn, wheat and barley were sown in 1/5,000-are Wagner pots filled with upland soil, and covered with upland soil. The seeds were grown in a greenhouse, and at the stage of 1~2 leaves of these plants, a predetermined amount of the herbicide prepared in the above (1) was suspended in water and uniformly sprayed onto leaf and stalk portions at a rate of 200 liter/10 ares. Thereafter, the plants were grown in the greenhouse, and on 20th day after the spraying treatment, the herbicide was evaluated for herbicidal efficacy. Table 29 shows the results.

The herbicidal efficacy and phytotoxcity to crops were shown on the basis of the following ratings.

The ratio of remaining plant weight to non-treated was determined on the basis of the ratio of remaining plant weight to non-treated=(remaining plant weight in treated plot/remaining plant weight in non-treated plot)×100. This is also applicable to biological tests hereinafter.

(Ratings)

| Herbicidal efficacy | Ratio of remaining plant weight to non-treated (%) |
|---|---|
| 0 | 81–100 |
| 1 | 61–80 |
| 2 | 41–60 |
| 3 | 21–40 |
| 4 | 1–20 |
| 5 | 0 |

| Phytotoxicity to corn | Ratio of remaining plant weight to non-treated (%) |
|---|---|
| − | 100 |
| ± | 95–99 |
| + | 90–94 |
| ++ | 80–89 |
| +++ | 0–79 |

TABLE 29

| Herbicide Exam. No. | Comp'd No. | Dosage (g$^{a.i.}$/ hectare) | Herbicidal Efficacy | | | | | | Phytotoxicity | | |
|---|---|---|---|---|---|---|---|---|---|---|---|
| | | | large crabgrass | barnyard grass | green foxtail | cockle- bur | velvet- leaf | slender amaranth | corn | wheat | barley |
| 43 | 43 | 300 | 5 | 5 | 5 | 5 | 5 | 5 | — | — | — |
| 44 | 49 | 300 | 5 | 5 | 5 | 5 | 5 | 5 | — | — | — |
| 45 | 50 | 300 | 5 | 5 | 5 | 5 | 5 | 5 | — | — | — |
| 46 | 47-1 | 300 | 0 | 0 | 0 | 5 | 4 | 0 | — | — | — |
| 47 | 47-2 | 300 | 5 | 2 | 5 | 5 | 5 | 5 | — | — | — |
| Comp. Exam. 11 | x | 1000 | 0 | 0 | 0 | 0 | 0 | 0 | — | — | — |
| Comp. Exam. 12 | y | 300 | 0 | 0 | 0 | 3 | 3 | 2 | — | — | — |

$^{a.i.}$ = active ingredient (8) Biological Test (Upland Soil Treatment Test, Herbicide Examples 48–52 and Herbicide Comparative Examples 13 and 14)

Seeds of weeds such as large crabgrass, barnyard grass, green foxtail, cocklebur, velvetleaf and slender amaranth and seeds of corn, wheat and barley were sown in 1/5,000-are Wagner pots filled with upland soil, and covered with land soil. Then, a predetermined amount of the herbicide prepared in the above (1) was suspended in water and uniformly sprayed onto the soil surface. Thereafter, the plants were grown in the greenhouse, and on 20th day after the spraying treatment, the herbicide was evaluated for herbicidal efficacy. Table 30 shows the results.

The herbicidal efficacy and the phytotoxicity to crops are shown on the basis of the ratings described in (2) Foliar treatment test.

TABLE 30

| Herbicide Exam. No. | Comp'd No. | Dosage (g$^{a.i.}$/ hectare) | Herbicidal Efficacy | | | | | | Phytotoxicity | | |
|---|---|---|---|---|---|---|---|---|---|---|---|
| | | | large crabgrass | barnyard grass | green foxtail | cockle-bur | velvet-leaf | slender amaranth | corn | wheat | barley |
| 48 | 43 | 300 | 5 | 5 | 5 | 5 | 5 | 5 | — | — | — |
| 49 | 49 | 300 | 5 | 5 | 5 | 5 | 5 | 5 | — | — | — |
| 50 | 50 | 300 | 5 | 5 | 5 | 5 | 5 | 5 | — | — | — |
| 51 | 47-1 | 300 | 0 | 0 | 0 | 0 | 0 | 5 | — | — | — |
| 52 | 47-2 | 300 | 1 | 5 | 4 | 0 | 5 | 5 | — | — | — |
| Comp. Exam. 13 | x | 1000 | 0 | 0 | 0 | 0 | 0 | 1 | — | — | — |
| Comp. Exam. 14 | y | 300 | 3 | 3 | 2 | 0 | 0 | 0 | — | — | — |

$^{a.i.}$ = active ingredient

As explained in detail above, there are provided novel pyrazole derivatives which can selectively control gramineous weeds and broad-leaved weeds together by any one of Foliar treatment and soil treatment at a low dosage without causing phytotoxicity on useful crops such as rice, corn, wheat, barley, and the like, herbicides containing the above novel pyrazole derivatives as active ingredients, and intermediate compounds suitable for the production of the above novel pyrazole derivatives.

What is claimed is:

1. An aromatic carboxylic acid bicyclic sulfur compound of the formula (II),

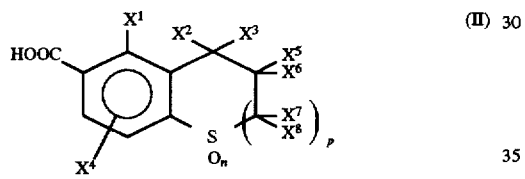

wherein:

$X^1$ is one member selected from the group consisting of a $C_1$ to $C_4$ alkyl group, a halogen atom, a $C_1$ to $C_4$ haloalkyl group, a $C_2$ to $C_4$ alkoxyalkyl group, a $C_1$ to $C_4$ alkoxy group and a $C_1$ to $C_4$ haloalkoxy group;

each of $X^2$ and $X^3$ is independently one member selected from the group consisting of a hydrogen atom, a $C_1$ to $C_4$ alkyl group and a $C_1$ to $C_4$ haloalkyl group;

$X^4$ is one member selected from the group consisting of a hydrogen atom, a halogen atom, a $C_1$ to $C_4$ alkyl group, a $C_1$ to $C_4$ haloalkyl group and a $C_1$ to $C_4$ alkoxy group;

each of $X^5$, $X^6$, $X^7$ and $X^8$ is independently a hydrogen atom or a $C_1$ to $C_4$ group;

p is 1; and n is an integer of 0, 1 or 2, or a salt thereof.

2. The compound of claim 1, wherein $X^1$ is selected from the group consisting of methyl, ethyl, chlorine, methoxy, ethoxy, propoxy, butoxy, —$OCF_3$, —$OC_2F_5$, —$OC_2H_4F$, —$OC_2H_4Cl$, —$OCHF_2$, —$OCH_2F$, —$OCCl_3$, —$OC_2H_3Cl_2$ and —$OC_2H_3F_2$.

3. The compound of claim 2, wherein $X^2$ and $X^3$ are each independently selected from the group consisting of hydrogen, methyl, ethyl, —$CF_3$, —$C_2F_5$, —$C_2H_4F$, —$CH_2Cl$, —$CHF_2$, —$CCl_3$, —$C_2H_3$, $Cl_2$ and —$C_2H_3F_2$.

4. The compound of claim 3, wherein $X^4$ is selected from the group consisting of hydrogen, chlorine, methyl, —$CF_3$, —$C_2H_5$, —$C_2H_4F$, —$CH_2Cl$, —$CHF_2$, —$CCl_3$, —$C_2H_3Cl$, —$C_2H_3F_2$, methoxy, ethoxy, propoxy and butoxy.

5. The compound of claim 4, wherein each of $X^5$, $X^6$, $X^7$ and $X^8$ is selected from the group consisting of hydrogen and methyl.

6. The compound of claim 1, which is of the formula

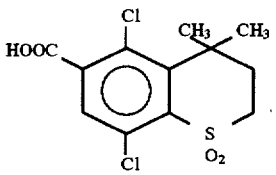

7. The compound of claim 1, which is of the formula

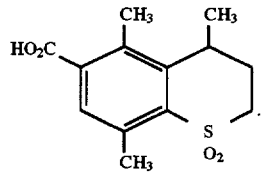

8. The compound of claim 1, which is of the formula

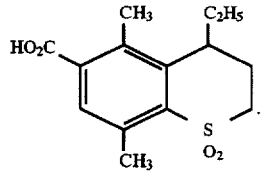

9. The compound of claim 1, which is of the formula

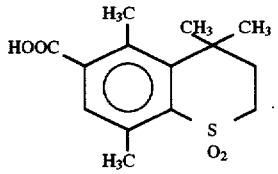

10. The compound of claim 1, which is of the formula

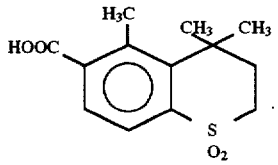

* * * * *

UNITED STATES PATENT AND TRADEMARK OFFICE
CERTIFICATE OF CORRECTION

PATENT NO. : 5,767,289
DATED : June 16, 1998
INVENTOR(S) : Kazufumi Nakamura et al.

It is certified that error appears in the above-identified patent and that said Letters Patent is hereby corrected as shown below:

Column 115,
Line 50, between "$C_1$ to $C_4$" and "group" insert -- alkyl --.

Signed and Sealed this

Seventh Day of January, 2003

JAMES E. ROGAN
*Director of the United States Patent and Trademark Office*